US011969500B2

(12) United States Patent
Naga et al.

(10) Patent No.: US 11,969,500 B2
(45) Date of Patent: *Apr. 30, 2024

(54) IMPLANTABLE DEPOTS FOR THE CONTROLLED RELEASE OF THERAPEUTIC AGENTS

(71) Applicant: Foundry Therapeutics, Inc., Menlo Park, CA (US)

(72) Inventors: Karun D. Naga, Los Altos, CA (US); Hanson S. Gifford, III, Woodside, CA (US); Stephen W. Boyd, San Francisco, CA (US); Patrick H. Ruane, El Dorado Hills, CA (US); Jackie Joe Hancock, Berkeley, CA (US); Michael Feldstein, San Francisco, CA (US); Koon Kiat Teu, Singapore (SG); Honglei Wang, Singapore (SG); Jingnan Luo, Singapore (SG); Daniel Boon Lim Seet, Singapore (SG)

(73) Assignee: Foundry Therapeutics, Inc., Menlo Park, CA (US)

( * ) Notice: Subject to any disclaimer, the term of this patent is extended or adjusted under 35 U.S.C. 154(b) by 135 days.

This patent is subject to a terminal disclaimer.

(21) Appl. No.: 17/454,320

(22) Filed: Nov. 10, 2021

(65) Prior Publication Data

US 2022/0117885 A1 Apr. 21, 2022

Related U.S. Application Data

(63) Continuation of application No. 17/248,949, filed on Feb. 15, 2021, now Pat. No. 11,224,570, which is a continuation of application No. 16/840,215, filed on Apr. 3, 2020, now Pat. No. 11,202,754, which is a continuation of application No. PCT/US2018/054777, filed on Oct. 6, 2018.

(60) Provisional application No. 62/723,478, filed on Aug. 28, 2018, provisional application No. 62/670,721, filed on May 12, 2018, provisional application No. 62/640,571, filed on Mar. 8, 2018, provisional application No. 62/569,349, filed on Oct. 6, 2017.

(51) Int. Cl.
*A61K 9/70* (2006.01)
*A61K 9/00* (2006.01)
*A61K 31/445* (2006.01)
*A61K 47/34* (2017.01)

(52) U.S. Cl.
CPC .......... *A61K 9/0024* (2013.01); *A61K 31/445* (2013.01); *A61K 47/34* (2013.01)

(58) Field of Classification Search
CPC .... A61K 9/0024; A61K 31/445; A61K 47/34; A61K 9/7007; A61L 2300/402; A61L 2300/602; A61L 27/54; A61L 27/58; A61P 23/02; A61P 25/04; A61P 29/00
See application file for complete search history.

(56) References Cited

U.S. PATENT DOCUMENTS

| | | |
|---|---|---|
| 4,601,893 A | 7/1986 | Cardinal |
| 4,666,704 A | 5/1987 | Shalati et al. |
| 4,919,939 A | 4/1990 | Baker |
| 5,227,165 A | 7/1993 | Domb et al. |
| 5,451,408 A | 9/1995 | Mezei et al. |
| 5,458,582 A | 10/1995 | Nakao |
| 5,540,912 A | 7/1996 | Roorda et al. |
| 5,618,563 A | 4/1997 | Berde et al. |
| 5,700,485 A | 12/1997 | Berde et al. |
| 5,747,060 A | 5/1998 | Sackler et al. |
| 5,807,306 A | 9/1998 | Shapland et al. |
| 5,919,473 A | 7/1999 | Elkhoury |
| 5,931,809 A | 8/1999 | Gruber et al. |
| 5,942,241 A | 8/1999 | Chasin et al. |
| 6,046,187 A | 4/2000 | Berde et al. |
| 6,149,937 A | 11/2000 | Camu et al. |
| 6,214,387 B1 | 4/2001 | Berde et al. |
| 6,248,345 B1 | 6/2001 | Goldenheim et al. |
| 6,326,020 B1 | 12/2001 | Kohane et al. |
| 6,451,335 B1 | 9/2002 | Goldenheim et al. |
| 6,699,908 B2 | 3/2004 | Sackler et al. |

(Continued)

FOREIGN PATENT DOCUMENTS

| | | |
|---|---|---|
| AU | 2012201226 B2 | 8/2014 |
| AU | 2013200515 B2 | 1/2016 |

(Continued)

OTHER PUBLICATIONS

Lee, et al., "Gemcitabine-releasing polymeric films for covered self-expandable metallic stent in treatment of gastrointestinal cancer", International Journal of Pharmaceutics, vol. 427, 2012, pp. 276-283.
International Search Report and Written Opinion mailed May 23, 2019; International Application No. PCT/US2019/012795; 15 pages.
International Search Report and Written Opinion mailed Nov. 14, 2019; International Application No. PCT/US2019/048437; 15 pages.
International Search Report and Written Opinion mailed Nov. 20, 2019; International Application No. PCT/US2019/048386; 13 pages.
Ball, et al., "Electrospun Solid Dispersions of Maraviroc for Rapid Intravaginal Preexposure Prophylaxis of HIV", Antimicrobial Agents and Chemotherapy, vol. 58, No. 8, Aug. 2014, pp. 4855-4865.

(Continued)

*Primary Examiner* — Jessica Worsham
(74) *Attorney, Agent, or Firm* — Fortem IP LLP

(57) ABSTRACT

The present technology relates to depots for the treatment of postoperative pain via sustained, controlled release of a therapeutic agent. In some embodiments, the depot may comprise a therapeutic region comprising an analgesic, and a control region comprising a bioresorbable polymer and a releasing agent mixed with the polymer. The releasing agent may be configured to dissolve when the depot is placed in vivo to form diffusion openings in the control region. The depot may be configured to be implanted at a treatment site in vivo and, while implanted, release the therapeutic agent at the treatment site for no less than 3 days.

31 Claims, 33 Drawing Sheets

(56) References Cited

U.S. PATENT DOCUMENTS

| | | |
|---|---|---|
| 6,913,760 B2 | 7/2005 | Carr et al. |
| 7,074,426 B2 | 7/2006 | Kochinke |
| 7,220,433 B2 | 5/2007 | Cui et al. |
| 7,723,291 B2 | 5/2010 | Beals et al. |
| 7,727,954 B2 | 6/2010 | McKay |
| 7,741,273 B2 | 6/2010 | McKay |
| 7,824,703 B2 | 11/2010 | Scifert et al. |
| 7,947,301 B2 | 5/2011 | Bischoff et al. |
| 7,993,390 B2 | 8/2011 | Miller et al. |
| 8,067,026 B2 | 11/2011 | Ranade et al. |
| 8,080,059 B2 | 12/2011 | Fell |
| 8,153,149 B2 | 4/2012 | Verity |
| 8,202,531 B2 | 6/2012 | McKay |
| 8,221,358 B2 | 7/2012 | McKay |
| 8,231,891 B2 | 7/2012 | King |
| 8,246,571 B2 | 8/2012 | Simonton et al. |
| 8,257,393 B2 | 9/2012 | Cichocki |
| 8,357,388 B2 | 1/2013 | McKay |
| 8,420,600 B2 | 4/2013 | Burch et al. |
| 8,430,852 B2 | 4/2013 | Bischoff et al. |
| 8,470,360 B2 | 6/2013 | McKay |
| 8,523,569 B2 | 9/2013 | Neshat |
| 8,524,267 B2 | 9/2013 | Zanella et al. |
| 8,575,092 B2 | 11/2013 | Domb |
| 8,591,531 B2 | 11/2013 | Buevich et al. |
| 8,603,528 B2 | 12/2013 | Kronenthal |
| 8,623,396 B2 | 1/2014 | Gray et al. |
| 8,629,172 B2 | 1/2014 | McKay et al. |
| 8,632,839 B2 | 1/2014 | Stopek et al. |
| 8,652,504 B2 | 2/2014 | Li et al. |
| 8,652,525 B2 | 2/2014 | Moses et al. |
| 8,663,192 B2 | 3/2014 | Hester et al. |
| 8,697,117 B2 | 4/2014 | Zilberman |
| 8,703,119 B2 | 4/2014 | Yankelson et al. |
| 8,708,966 B2 | 4/2014 | Allen et al. |
| 8,715,223 B2 | 5/2014 | McKay |
| 8,728,493 B2 | 5/2014 | Burton et al. |
| 8,728,509 B2 | 5/2014 | McKay |
| 8,750,983 B2 | 6/2014 | Bonutti |
| 8,758,798 B2 | 6/2014 | Stopek et al. |
| 8,795,713 B2 | 8/2014 | Makower et al. |
| 8,809,530 B1 | 8/2014 | Wu et al. |
| 8,822,492 B2 | 9/2014 | Schachter |
| 8,846,068 B2 | 9/2014 | Wohabrebbi et al. |
| 8,865,205 B2 | 10/2014 | Shalaby |
| 8,877,226 B2 | 11/2014 | Zanella et al. |
| 8,889,173 B2 | 11/2014 | Zanella et al. |
| 8,900,620 B2 | 12/2014 | Fulmer et al. |
| 8,911,765 B2 | 12/2014 | Moses et al. |
| 8,920,867 B2 | 12/2014 | Stopek et al. |
| 8,951,552 B2 | 2/2015 | Shalaby et al. |
| 8,956,642 B2 | 2/2015 | Hobot et al. |
| 8,968,767 B2 | 3/2015 | McKay |
| 8,969,397 B2 | 3/2015 | Burright et al. |
| 8,980,317 B2 | 3/2015 | King |
| 8,999,368 B2 | 4/2015 | McDonald et al. |
| 9,005,634 B2 | 4/2015 | McDonald et al. |
| 9,011,965 B2 | 4/2015 | Gan et al. |
| 9,023,114 B2 | 5/2015 | Buevich et al. |
| 9,125,814 B2 | 9/2015 | He et al. |
| 9,125,917 B2 | 9/2015 | McKay et al. |
| 9,132,087 B2 | 9/2015 | Lichter et al. |
| 9,132,194 B2 | 9/2015 | McKay |
| 9,155,707 B2 | 10/2015 | Ying et al. |
| 9,161,903 B2 | 10/2015 | Drapeau et al. |
| 9,173,732 B2 | 11/2015 | Langer et al. |
| 9,198,758 B2 | 12/2015 | McKay |
| 9,205,052 B2 | 12/2015 | Kim et al. |
| 9,211,285 B2 | 12/2015 | McKay et al. |
| 9,265,733 B2 | 2/2016 | McKay |
| 9,283,283 B2 | 3/2016 | Giammona et al. |
| 9,289,409 B2 | 3/2016 | Zanella et al. |
| 9,295,462 B2 | 3/2016 | Choy et al. |
| 9,302,903 B2 | 4/2016 | Park et al. |
| 9,320,708 B2 | 4/2016 | Scifert et al. |
| 9,351,924 B2 | 5/2016 | Cho et al. |
| 9,352,137 B2 | 5/2016 | Simonton et al. |
| 9,358,223 B2 | 6/2016 | King |
| 9,375,420 B2 | 6/2016 | King |
| 9,402,918 B2 | 8/2016 | Koyakutty et al. |
| 9,402,973 B2 | 8/2016 | Phillips et al. |
| 9,457,176 B2 | 10/2016 | Lee et al. |
| 9,504,749 B2 | 11/2016 | McKay |
| 9,522,113 B2 | 12/2016 | Spada et al. |
| 9,549,920 B2 | 1/2017 | Wohabrebbi et al. |
| 9,566,241 B2 | 2/2017 | Ravis et al. |
| 9,597,132 B2 | 3/2017 | Houff |
| 9,610,194 B2 | 4/2017 | De Juan et al. |
| 9,610,243 B2 | 4/2017 | Clay et al. |
| 9,623,222 B2 | 4/2017 | McKay |
| 9,629,818 B2 | 4/2017 | Nadkarni et al. |
| 9,655,994 B2 | 5/2017 | McKay |
| 9,668,974 B2 | 6/2017 | Amselem et al. |
| 9,669,117 B2 | 6/2017 | Campbell et al. |
| 9,694,079 B2 | 7/2017 | Ottoboni et al. |
| 9,700,567 B2 | 7/2017 | Zanella et al. |
| 9,724,300 B2 | 8/2017 | Yamashita et al. |
| 9,764,066 B2 | 9/2017 | Sim et al. |
| 9,821,091 B2 | 11/2017 | Hossainy et al. |
| 9,833,548 B2 | 12/2017 | McKay et al. |
| 9,861,590 B2 | 1/2018 | Stopek et al. |
| 9,987,233 B2 | 6/2018 | Helliwell et al. |
| 11,202,754 B2 | 12/2021 | Naga et al. |
| 11,224,570 B2 | 1/2022 | Naga et al. |
| 2001/0044651 A1 | 11/2001 | Steinke et al. |
| 2001/0055607 A1 | 12/2001 | Levin |
| 2002/0106410 A1 | 8/2002 | Masters |
| 2003/0022876 A1 | 1/2003 | Ashton et al. |
| 2003/0036803 A1 | 2/2003 | McGhan |
| 2003/0118649 A1 | 6/2003 | Gao et al. |
| 2003/0152637 A1 | 8/2003 | Chasin et al. |
| 2003/0157162 A1 | 8/2003 | Krugner-Higby et al. |
| 2003/0190341 A1 | 10/2003 | Shalaby et al. |
| 2003/0215496 A1 | 11/2003 | Patel et al. |
| 2004/0109893 A1 | 6/2004 | Chen et al. |
| 2004/0249441 A1 | 12/2004 | Miller et al. |
| 2005/0019404 A1 | 1/2005 | Sung et al. |
| 2005/0048115 A1 | 3/2005 | Mangena et al. |
| 2005/0152957 A1 | 7/2005 | Cleary et al. |
| 2005/0158382 A1 | 7/2005 | Cruz et al. |
| 2005/0206048 A1 | 9/2005 | Ryu et al. |
| 2005/0266077 A1 | 12/2005 | Royer |
| 2006/0034887 A1 | 2/2006 | Pelissier |
| 2006/0079558 A1 | 4/2006 | Aberg et al. |
| 2006/0079559 A1 | 4/2006 | Aberg et al. |
| 2006/0269475 A1 | 11/2006 | Ryu et al. |
| 2007/0071790 A1 | 3/2007 | Ameer et al. |
| 2007/0134292 A1 | 6/2007 | Suokas et al. |
| 2007/0173787 A1 | 7/2007 | Huang et al. |
| 2007/0178138 A1 | 8/2007 | Pal et al. |
| 2007/0258939 A1 | 11/2007 | Lewis et al. |
| 2008/0089923 A1 | 4/2008 | Burkstrand et al. |
| 2008/0095849 A1 | 4/2008 | Wu et al. |
| 2008/0132922 A1 | 6/2008 | Buevich et al. |
| 2008/0154241 A1 | 6/2008 | Burkstrand et al. |
| 2008/0228193 A1 | 9/2008 | Matityahu |
| 2008/0241212 A1 | 10/2008 | Moses et al. |
| 2008/0311191 A1 | 12/2008 | Nangia et al. |
| 2009/0076595 A1 | 3/2009 | Lindquist et al. |
| 2009/0087380 A1 | 4/2009 | Fasching et al. |
| 2009/0123508 A1 | 5/2009 | Cheng et al. |
| 2009/0142400 A1 | 6/2009 | Hiles et al. |
| 2009/0155326 A1 | 6/2009 | Mack et al. |
| 2009/0177229 A1 | 7/2009 | Gulotta et al. |
| 2009/0182425 A1 | 7/2009 | Duda et al. |
| 2009/0198197 A1 | 8/2009 | Bischoff et al. |
| 2009/0263321 A1 | 10/2009 | McDonald et al. |
| 2009/0263441 A1 | 10/2009 | McKay |
| 2009/0263443 A1 | 10/2009 | King |
| 2009/0263451 A1 | 10/2009 | King |
| 2009/0264472 A1 | 10/2009 | Wohabrebbi et al. |
| 2009/0264477 A1 | 10/2009 | Zanella et al. |
| 2009/0264489 A1 | 10/2009 | Hildebrand et al. |
| 2009/0325879 A1 | 12/2009 | Norton et al. |

(56) References Cited

U.S. PATENT DOCUMENTS

| | | |
|---|---|---|
| 2010/0023126 A1* | 1/2010 | Grotz ............... A61F 2/30721 623/14.12 |
| 2010/0055437 A1 | 3/2010 | Fink et al. |
| 2010/0158970 A1 | 6/2010 | Tipton et al. |
| 2010/0168808 A1 | 7/2010 | Citron |
| 2010/0198278 A1 | 8/2010 | Cobian et al. |
| 2010/0203100 A1 | 8/2010 | Cobian et al. |
| 2010/0203102 A1 | 8/2010 | Wohabrebbi |
| 2010/0249783 A1 | 9/2010 | Trieu |
| 2011/0027331 A1 | 2/2011 | Hobot |
| 2011/0060309 A1 | 3/2011 | Lee et al. |
| 2011/0081422 A1 | 4/2011 | Masinde et al. |
| 2011/0082545 A1 | 4/2011 | Freund |
| 2011/0129801 A1 | 6/2011 | Barman |
| 2011/0137243 A1 | 6/2011 | Hossainy et al. |
| 2011/0152839 A1 | 6/2011 | Cima et al. |
| 2011/0184037 A1 | 7/2011 | Haddock et al. |
| 2011/0206752 A1 | 8/2011 | Carreno et al. |
| 2011/0224245 A1 | 9/2011 | Schachter |
| 2011/0281882 A1 | 11/2011 | Zhang et al. |
| 2012/0009240 A1 | 1/2012 | Stopek et al. |
| 2012/0097194 A1 | 4/2012 | McDaniel et al. |
| 2012/0100192 A1 | 4/2012 | Penhasi et al. |
| 2012/0114740 A1 | 5/2012 | Garcia et al. |
| 2012/0165795 A1 | 6/2012 | Seiler et al. |
| 2012/0239001 A1 | 9/2012 | Barry et al. |
| 2012/0263761 A1 | 10/2012 | McDonald et al. |
| 2012/0316199 A1 | 12/2012 | Ward et al. |
| 2013/0018321 A1 | 1/2013 | McKay |
| 2013/0071463 A1 | 3/2013 | Palasis et al. |
| 2013/0136811 A1 | 5/2013 | Schachter |
| 2013/0158652 A1 | 6/2013 | Palasis et al. |
| 2013/0164347 A1 | 6/2013 | Gensini et al. |
| 2013/0261594 A1 | 10/2013 | Stopek et al. |
| 2013/0280272 A1 | 10/2013 | Trogden et al. |
| 2014/0052183 A1 | 2/2014 | Freese |
| 2014/0065202 A1 | 3/2014 | To |
| 2014/0072608 A1 | 3/2014 | Logothetidis et al. |
| 2014/0086971 A1 | 3/2014 | Hall et al. |
| 2014/0088347 A1 | 3/2014 | Frigstad et al. |
| 2014/0105956 A1 | 4/2014 | Banerjee et al. |
| 2014/0107159 A1 | 4/2014 | Ebersole et al. |
| 2014/0170204 A1 | 6/2014 | Desai et al. |
| 2014/0193466 A1 | 7/2014 | Lawrence et al. |
| 2014/0193504 A1 | 7/2014 | Wooley et al. |
| 2014/0214175 A1 | 7/2014 | Barron et al. |
| 2014/0255464 A1 | 9/2014 | Hakimimehr et al. |
| 2014/0271770 A1 | 9/2014 | Clay et al. |
| 2014/0287053 A1 | 9/2014 | Helliwell et al. |
| 2015/0018969 A1 | 1/2015 | Fulmer et al. |
| 2015/0024031 A1 | 1/2015 | Rabinow et al. |
| 2015/0024116 A1 | 1/2015 | Matson et al. |
| 2015/0038415 A1 | 2/2015 | Zupancich |
| 2015/0039097 A1 | 2/2015 | Biris |
| 2015/0150988 A1 | 6/2015 | Shalaby et al. |
| 2015/0246001 A1 | 9/2015 | Zupancich et al. |
| 2015/0272877 A1 | 10/2015 | Shi et al. |
| 2015/0290170 A1 | 10/2015 | Liu et al. |
| 2015/0342964 A1 | 12/2015 | Gray et al. |
| 2016/0038632 A1 | 2/2016 | Shah et al. |
| 2016/0089335 A1 | 3/2016 | Ohri et al. |
| 2016/0136094 A1 | 5/2016 | Criscione et al. |
| 2016/0144040 A1 | 5/2016 | Cheng |
| 2016/0144067 A1 | 5/2016 | Armbruster et al. |
| 2016/0184340 A1 | 6/2016 | Kritikou |
| 2016/0287367 A1 | 10/2016 | Rontal |
| 2016/0331853 A1 | 11/2016 | Taub |
| 2016/0339152 A1 | 11/2016 | Bonutti et al. |
| 2016/0354309 A1 | 12/2016 | Heitzmann et al. |
| 2017/0014337 A1 | 1/2017 | Walsh |
| 2017/0079929 A1 | 3/2017 | Davey |
| 2017/0128632 A1 | 5/2017 | Mcjames |
| 2017/0182168 A1 | 6/2017 | Ottoboni et al. |
| 2017/0196499 A1 | 7/2017 | Hunter |
| 2017/0196508 A1 | 7/2017 | Hunter |
| 2017/0216597 A1 | 8/2017 | Hou et al. |
| 2017/0239183 A1 | 8/2017 | Reynolds et al. |
| 2017/0246117 A1 | 8/2017 | Helliwell et al. |
| 2017/0281778 A1 | 10/2017 | Ottoboni et al. |
| 2018/0092855 A1 | 4/2018 | Kim et al. |
| 2019/0351108 A1 | 11/2019 | Wang et al. |
| 2020/0009293 A1 | 1/2020 | Teu et al. |
| 2020/0246255 A1 | 8/2020 | Naga et al. |
| 2020/0368398 A1 | 11/2020 | Naga et al. |
| 2021/0186868 A1 | 6/2021 | Naga et al. |
| 2021/0308338 A1 | 10/2021 | Ruane et al. |
| 2021/0361827 A1 | 11/2021 | Teu et al. |
| 2022/0072207 A1 | 3/2022 | Wang et al. |
| 2022/0183963 A1 | 6/2022 | Kim et al. |
| 2022/0183964 A1 | 6/2022 | Naga et al. |
| 2023/0136789 A1 | 5/2023 | Ruane et al. |

FOREIGN PATENT DOCUMENTS

| | | |
|---|---|---|
| CN | 1344156 A | 4/2002 |
| CN | 1655738 A | 8/2005 |
| CN | 1762331 A | 4/2006 |
| CN | 102000366 A | 4/2011 |
| CN | 102341133 A | 2/2012 |
| CN | 103405748 A | 11/2013 |
| CN | 103703079 A | 4/2014 |
| CN | 104474595 A | 4/2015 |
| CN | 104474595 B | 1/2017 |
| CN | 106344521 A | 1/2017 |
| EP | 0311065 B1 | 2/1994 |
| EP | 1868662 B1 | 5/2010 |
| EP | 2197419 A2 | 6/2010 |
| EP | 2209469 A2 | 7/2010 |
| EP | 2229171 A2 | 9/2010 |
| EP | 2262481 A2 | 12/2010 |
| EP | 2285363 A2 | 2/2011 |
| EP | 2288352 A2 | 3/2011 |
| EP | 2288353 A2 | 3/2011 |
| EP | 2368522 A1 | 9/2011 |
| EP | 2444074 A2 | 4/2012 |
| EP | 2444075 A2 | 4/2012 |
| EP | 2696851 A1 | 2/2014 |
| EP | 2719717 A1 | 4/2014 |
| EP | 3000463 A1 | 3/2016 |
| EP | 3085359 A1 | 10/2016 |
| EP | 2195073 B1 | 3/2017 |
| EP | 2444073 B1 | 5/2017 |
| EP | 2911647 B1 | 3/2018 |
| GB | 201505527 | 5/2015 |
| JP | 102119866 A | 5/1990 |
| JP | 2006512312 A | 4/2006 |
| JP | 2009511196 A | 3/2009 |
| JP | 2012017329 A | 1/2012 |
| JP | 2015522649 A | 8/2015 |
| JP | 2016528949 A | 9/2016 |
| JP | 2018511410 A | 4/2018 |
| JP | 6824188 B2 | 1/2021 |
| WO | 9509613 A1 | 4/1995 |
| WO | 9858653 A1 | 12/1998 |
| WO | 9936071 A1 | 7/1999 |
| WO | 2006099409 A3 | 3/2007 |
| WO | 2007047420 A2 | 4/2007 |
| WO | 2008061355 A1 | 5/2008 |
| WO | 2008127411 A1 | 10/2008 |
| WO | 2008131089 A2 | 10/2008 |
| WO | 2008136856 A2 | 11/2008 |
| WO | 2009069151 A2 | 6/2009 |
| WO | 2009113972 A2 | 9/2009 |
| WO | 2009129432 A2 | 10/2009 |
| WO | 2009129433 A2 | 10/2009 |
| WO | 2009129439 A2 | 10/2009 |
| WO | 2009129453 A2 | 10/2009 |
| WO | 2009129456 A2 | 10/2009 |
| WO | 2009129460 A2 | 10/2009 |
| WO | 2009129464 A2 | 10/2009 |
| WO | 2009129491 A2 | 10/2009 |
| WO | 2009129494 A2 | 10/2009 |
| WO | 2009129509 A2 | 10/2009 |
| WO | 2009129519 A2 | 10/2009 |

(56) References Cited

FOREIGN PATENT DOCUMENTS

| | | | |
|---|---|---|---|
| WO | 2009129527 | A2 | 10/2009 |
| WO | 2009129531 | A2 | 10/2009 |
| WO | 2010016832 | A1 | 2/2010 |
| WO | 2010075298 | A2 | 7/2010 |
| WO | 2010088697 | A2 | 8/2010 |
| WO | 2011098578 | A2 | 8/2011 |
| WO | 2011139594 | A2 | 11/2011 |
| WO | 2012064963 | A1 | 5/2012 |
| WO | 2012142318 | A1 | 10/2012 |
| WO | 2013013123 | A1 | 1/2013 |
| WO | 2013040325 | A1 | 3/2013 |
| WO | 2014016428 | A1 | 1/2014 |
| WO | 2014059558 | A1 | 4/2014 |
| WO | 2014064140 | A1 | 5/2014 |
| WO | 2014066653 | A1 | 5/2014 |
| WO | 2014137454 | A1 | 9/2014 |
| WO | 2014172572 | A1 | 10/2014 |
| WO | 2014204708 | A1 | 12/2014 |
| WO | 2015015278 | A1 | 2/2015 |
| WO | 2015135907 | A1 | 9/2015 |
| WO | 2016123352 | A1 | 8/2016 |
| WO | 2016159885 | A1 | 10/2016 |
| WO | 2017019829 | A1 | 2/2017 |
| WO | 2017034363 | A1 | 3/2017 |
| WO | 2017075232 | A1 | 5/2017 |
| WO | 2017146819 | A1 | 8/2017 |
| WO | 2018009637 | A1 | 1/2018 |
| WO | 2018063096 | A1 | 4/2018 |
| WO | 2018067882 | A1 | 4/2018 |
| WO | 2018172494 | A1 | 9/2018 |
| WO | 2018227293 | A1 | 12/2018 |
| WO | 2019071243 | A1 | 4/2019 |
| WO | 2019136490 | A1 | 7/2019 |
| WO | 2019221853 | A8 | 11/2019 |
| WO | 2020046973 | A1 | 3/2020 |
| WO | 2020047013 | A1 | 3/2020 |
| WO | 2020210764 | A1 | 10/2020 |
| WO | 2020210770 | A2 | 10/2020 |
| WO | 2021178930 | A1 | 9/2021 |
| WO | 2023056422 | A1 | 4/2023 |

OTHER PUBLICATIONS

Bassi, et al., "Polymeric films as a promising carrier for bioadhesive drug delivery: Development, characterization and optimization", Saudi Pharmaceutical Journal, vol. 25, 2017, pp. 32-43.

Chun, et al., "Gastrointestinal and Biliary Stents", Journal of Gastroenterology and Hepatology Foundation and Blackwell Publishing Asia Pty Ltd, vol. 25, 2010, pp. 234-243.

Curley, et al., "Prolonged Regional Nerve Blockade Injectable Biodegradable Bupivacaine/Polyester Microspheres", Anesthesiology, vol. 84, 1996, pp. 1401-1410.

Drager, et al., "Prolonged Intercostal Nerve Blockade in Sheep Using Controlled-release of Bupivacaine and Dexamethasome from Polymer Microspheres", Anesthesiology, vol. 89, No. 4, Oct. 1998, pp. 969-979.

Epstein-Barash, et al., "Prolonged duration local anesthesia with minimal toxicity", PNAS, vol. 106, No. 17, Apr. 28, 2009, pp. 7125-7130.

Farid, et al., "Promote Recurrent Aphthous Ulcer Healing with Low Dose Predisolone Bilayer Mucoadhesive Buccal Film", Current Drug Delivery, vol. 14, No. 1, Jan. 9, 2017, pp. 123-125.

Fites, "Controlled Drug Release through Polymeric Films", Journal of Pharmaceutical Sciences, vol. 59, No. 5, May 1970, pp. 610-613.

Friess, Wolfgang, "Review Article: Collagen—biomaterial for drug delivery", European Journal of Pharmaceutics and Biopharmaceutics, vol. 45, 1998, pp. 113-136.

Goindi, et al., "Development of Novel Ionic Liquid-Based Microemulsion Formulation for Dermal Delivery of 5-Fluorouracil", AAPS PharmSciTech 2014 15(4):810-821 (Year: 2014).

Guo, et al., "A type of esophageal stent coating composed of one 5-fluorouracil-containing EVA layer and one drug-free protective layer: In vitro release, permeation and mechanical properties" Journal of Controlled Release 2007 118:318-324 (Year: 2007).

Hong, Y., et al., "Generating Elastic, Biodegradable Polyurethane/Poly(lactide-co-glycolide) Fibrous Sheets with Controlled Antibiotic Release via Two-Stream Electrospinning", Biomacromolecules, 2008, 1200-1207.

Irfan, et al., "Orally disintegrating films: A modern expansion in drug delivery system", Saudi Pharmaceutical Journal, vol. 24, 2016, pp. 537-546.

Ito, et al., "Three-Layered Microcapsules as a Long-Term Sustained Release Injection Preparation", International Journal of Pharmaceuticals, vol. 384, No. 1-2, Jan. 1, 2010, pp. 53-59.

European Search Report dated Apr. 30, 2020; European Patent Application No. 17856916.6; 10 pages.

International Search Report and Written Opinion dated Oct. 30, 2017; International Application No. PCT/SG2017/050481; 10 pages.

International Search Report and Written Opinion mailed Feb. 19, 2019; International Application No. PCT/US2018/054777; 15 pages.

International Search Report and Written Opinion mailed Feb. 21, 2019; International Application No. PCT/US2018/054779; 17 pages.

International Search Report and Written Opinion mailed Jul. 24, 2019; International Application No. PCT/US2019/027104; 14 pages.

International Search Report and Written Opinion mailed Jul. 3, 2020; International Application No. PCT/US2020/027852; 14 pages.

International Search Report and Written Opinion mailed Jun. 15, 2016, International Application No. PCT/SG/2016/050158, 17 pages.

International Search Report and Written Opinion mailed Jun. 17, 2020; International Application No. PCT/US2020/027861; 11 pages.

International Search Report and Written Opinion mailed Jun. 21, 2021; International Application No. PCT/US2021/21256; 14 pages.

International Search Report and Written Opinion mailed May 10, 2019; International Application No. PCT/US2018/054780; 13 pages.

Jain, et al., "Injectable formulations of ply(lactic acid) and its copolymers in clinical use", Advanced Drug Delivery Reviews, vol. 107, Jul. 14, 2016, pp. 213-227.

Jethara, et al., "Sustained Release Drug Delivery Systems: a Patent Overview", Aperito Journal of Drug Designing and Pharmacology, 2014: 1:1, 15 Pages.

Jin, et al., "A PTX/nitinol stent combination with temperature-responsive phase-change 1-hexadecanol for magnetocaloric drug delivery: Magnetocaloric drug release and esophagus tissue penetration", Biomaterials, 153; Oct. 27, 2017, pp. 49-58.

Kanagale, et al., "Formulation and Optimization of Porous Osmotic Pump-based Controlled Release System and Oxybutynin", AAPA PharmSciTech 2007, vol. 8, No. 3, Article 53, 7 Pages.

Karki, et al., "Thin films as an emerging platform for drug delivery", Asian Journal of Pharmaceutical Sciences, vol. 11, No. 5, 2016, pp. 559-574.

Kau, et al., "Sustained Release of Lidocaine from Solvent-Free Biodegradable Poly [(d,I)-Lactide-co-Glycolide] (PLGA): In Vitro and In Vivo Study", Materials, vol. 7, 2014, pp. 6660-6676.

Knecht, et al., "Mechanical testing of fixation techniques for scaffold-based tissue-engineered grafts", Journal of Biomedical Materials Research Part B: Applied Biomaterials; vol. 83, No. 1, Feb. 22, 2007, pp. 50-57.

Kolek, Matthew J., et al., "Use of an Antibacterial Envelope is Associated with Reduced Cardiac Implantable Electronic Device Infections in High-Risk Patients", Pacing and Clinical Electrophysiology, vol. 36, Mar. 2013, 354-361.

Lee, et al., "Results of a model analysis of the cost-effectiveness of liraglutide versus exenatide added to metformin, glimepiride, or both for the treatment of type 2 diabetes in the United States", Clinical Therapeutics, vol. 32, No. 10, 2010, 12 Pages.

Lei, et al., "5-Fluorouracil-loaded multilayered films for drug controlled releasing stent application: Drug release, microstructure, and ex vivo permeation behaviors", Journal of Controlled Release, vol. 146; 2010-05-23; pp. 45-53.

Liu, et al., "Evaluation of two polymeric blends (EVA/PLA and EVA/PEG) as coating film materials for paclitaxel-eluting stent application", J Mater Sci: Mater Med, vol. 22, 2011, pp. 327-337.

Liu, et al., "Less harmful acidic degradation of poly(lactic-co-glycolic acid) bone tissue engineering scaffolds through titania

(56) References Cited

OTHER PUBLICATIONS nanoparticle addition", International Journal of Nanomedicine; vol. 1, No. 4, Jan. 1, 2006, pp. 541-545.

Liu, et al., "Paclitaxel or 5-fluorouracil/esophageal stent combinations as a novel approach for the treatment of esophageal cancer", Biomaterials, vol. 53, Jun. 1, 2015, pp. 592-599.

McAlvin, et al., "Local Toxicity from Local Anesthetic Polymeric Microparticles", Anesth Analg., vol. 116, No. 4, Apr. 2013, pp. 794-803.

NIHR HSC, et al., "AIGISRx® Antibacterial Envelope for Preventing Infection in Implanted Cardiac Devices", Birmingham: NIHR Horizon Scanning Centre (NIHR HSC), Horizon Scanning Review 2012, 1 Page.

Ohri, "Inhibition by Local Bupivacaine-Releasing Microspheres of Acute Postoperative Pain from Hairy Skin Incision", URL: www.anesthesia-analgesia.org, vol. 117, No. 3, Sep. 2013, 14 Pages.

Padera, et al., "Local myotoxicity from sustained release of bupivacaine from microparticles", Anesthesiology 2008, vol. 108, No. 5, May 2008, pp. 921-928.

Pek, et al., "Sustained Release of Bupivacaine for Post-Surgical Pain Relief Using Core-Shell Microspheres", Journal of Materials Chemistry B, 2014, 9 Pages.

Rong, et al., "PLC films incorporated with paclitaxel/5-flourouracil: Effects of formulation and spacial architecture on drug release", International Journal of Pharmeutics, vol. 427, 2012, pp. 242-251.

Roy, et al., "Effects of plasticizers and surfactants on the film forming properties of hydroxypropyl methylcellulose for the coating of diclofenac sodium tablets", Saudi Pharmaceutical Journal, vol. 17, 2009, pp. 233-241.

Santamaria, "Drug Delivery Systems for Prolonged Duration Local Anesthesia", Materials Today, vol. 20, No. 1, Jan./Feb. 2017., 22 Pages.

Seo, et al., "Polyurethane membrane with porous surface for controlled drug release in drug eluting stent", Biomaterials Research, vol. 18:15, 2014, 5 Pages.

Shaikh, "Engineering Stent Based Delivery System for Esophageal Cancer Using Docetaxel", Molecular Pharmaceutics, vol. 12, No. 7, Jul. 6, 2015, pp. 2305-2317.

Shipton, Edward A., "New Formulations of Local Anaesthetics—Part I", Anesthesiology Research and Practice, 2012, 12 Pages.

Sokolsky-Papkov, et al., "Long-Acting Poly (DL: Lactic Acid-Castor Oil) 3:7-Bupivacaine Formulation: Effect of Hydrophobic Additives", Pharmaceutical Research, Jun. 2011, 10 Pages.

Tallury, et al., "Effects of solubilizing surfactants and loading of antiviral, antimicrobial, and antifungal drugs on their release rates from ethylene vinyl acetate copolymer", Dental Materials 2007 23:977-982 (Year: 2007).

Tanabe, et al., "Controlled Indomethacin Release from Mucoadhesive Film: In Vitro and Clinical Evaluations", Yakugaku Zasshi Journal of the Pharmaceutical Society of Japan, vol. 128, No. 11, Nov. 1, 2008, pp. 1673-1679.

Tarakji, et al., "Cardiac implantable electronic device infections: Presentation, management, and patient outcomes", Heart Rhythm, vol. 7, No. 8, Aug. 2010, 6 Pages.

Voigt, et al., "Continued rise in rates of cardiovascular implantable electronic device infections in the United States; temporal trends and causative insights", PACE, vol. 33, Apr. 2010, 6 Pages.

Weiniger, C. F., "Extended release formulations for local anaesthetic agents", Anaesthesia 2012, vol. 67, No. 8, pp. 906-916.

Yamamura, et al., "Pain Relief of Oral Ulcer by Dibucaine-film", Elsevier Science Publishers, Amsterdam, NL, vol. 83, 1999, pp. 625-626.

Yan, et al., "Towards nanoporous polymer thin film-based drug delivery systems", Thin Solid Films, vol. 517, 2009, pp. 1794-1798.

Yuan, et al., "Fabrication of a Delaying Biodegradable Magnesium Alloy-Based Esophageal Stent via Coating Elastic Polymer", Materials 2016 9(384):1-11 (Year: 2016).

Zorzetto, et al., "From micro-to nanostructured implantable device for local anesthetic delivery", International Journal of Nanomedicine, Jun. 8, 2016, pp. 2695-2709.

\* cited by examiner

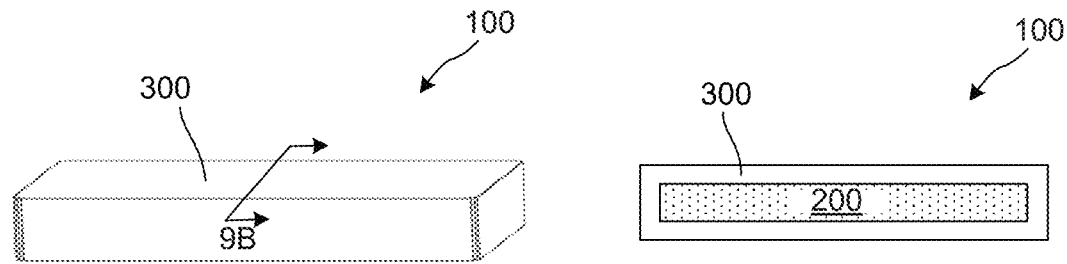
FIG. 9A  FIG. 9B
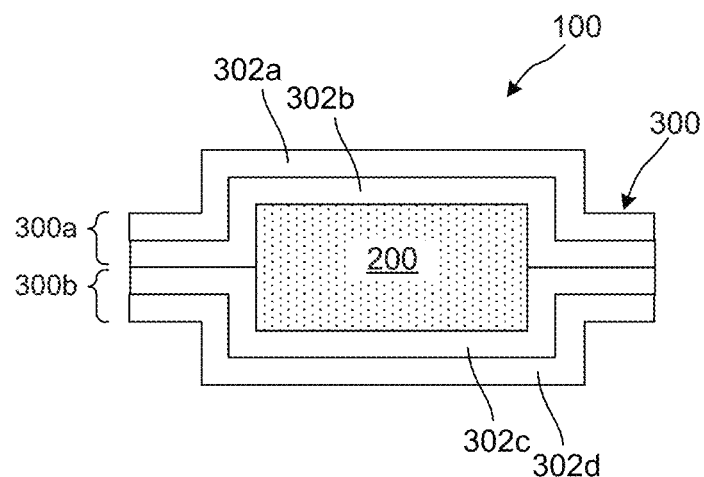
FIG. 10
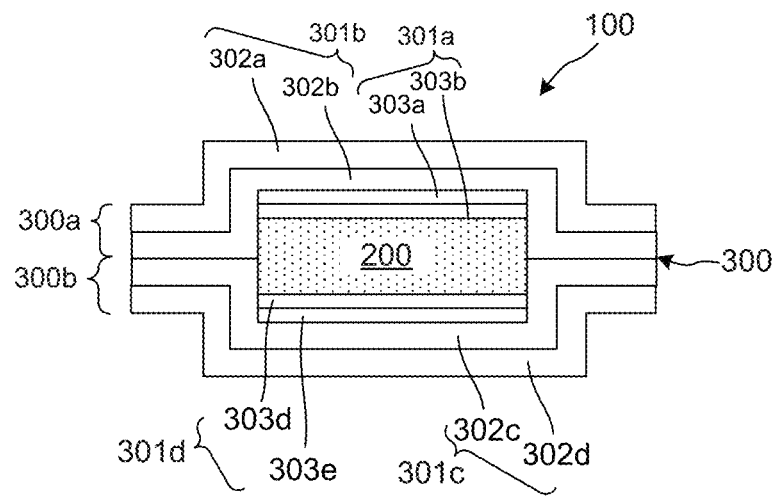
FIG. 11

| | Surgical Procedure | Nerve target(s) | Anatomical Access/ Placement |
|---|---|---|---|
| ORTHOPEDIC | Fibula Fracture Repair | Sciatic nerve | |
| | | Parasacral nerve | |
| | | Popliteal sciatic nerve | |
| | Anterior cruciate ligament reconstruction | Femoral nerve | |
| | | Sciatic nerve | |
| | Posterior cruciate ligament reconstruction | Parasacral nerve | |
| | Total knee arthroplasty | femoral nerve | femoral triangle |
| | | saphenous nerve | adductor canal |
| | | genicular nerves (superior lateral, superior medial, inferior medial) | |
| | | intra-capsular nerves | Periosteum |
| | | | Suprapatellar pouch/region |
| | | | Medial and lateral gutters |
| | | | Posterior capsule |
| | | Extra-capsular nerves | Quadraceps tendon |
| | | | Arthrotomy line |
| | | | Skin incision line |
| | Ankle fusion and Total ankle arthroplasty | Subgluteal sciatic nerve | |
| | | Parasacral nerve | |
| | | Popliteal sciatic nerve | |
| | Total hip arthroplasty | Lumbar plexus | Psoas compartment |
| | | Sacral plexus | |
| | | Femoral nerve | |
| | | Sciatic nerve | |
| | | Obturator nerve | |
| | Hip fracture | Sciatic nerve | fascia iliaca compartment |
| | | Femoral nerve | |
| | | Obturator nerve | |
| | | Superior gluteal nerve | |
| | Shoulder arthroplasty | Brachial Plexus | Cervical paravertebral |
| | Rotator cuff repair | | Interscalene |
| | Arm fractures (scapula, humerous, radius, ulna) | | Supraclavicular |
| | Elbow arthroplasty | Brachial Plexus | Cervical paravertebral |
| | Wrist arthroplasty | | Infraclavicular |
| | Upper limb trauma | | Axilliary |
| | Wrist and hand | Ulnar, median, radial and cutaneous forearm | antecubital fossa |
| | Spinal fusion | | |
| | Joint fusion | | |
| | Open reduction | | |

*FIG. 28A*

| | Surgical Procedure | Nerve target(s) | Anatomical Access/ Placement |
|---|---|---|---|
| | Open reconstruction | | |
| CHEST | Thoracotomy | Intercostal | Thoracic paravertebral |
| | Esophageus | | |
| | Cardiac | | |
| | Lung resection | | |
| | Thoracic | | |
| BREAST | | Intercostal nerve | Infraclavicular |
| | Augmentation | Pectoral (lateral and median) | Between serratus anterior muscle and latissimus dorsi muscle |
| | Reduction | | |
| | Reconstruction | | |
| Gynecology & Obstetrics | Myomectomy (uterine fibroid removal) | | |
| | Caesarean section | | |
| | Hysterectomy | | |
| | Oophorectomy (ovary removal) | | |
| | Pelvic floor reconstruction | | |
| General, Abdominal & Urology | Proctocolectomy (rectum and | | |
| | Pancreatectomy | | |
| | Appendectomy | | |
| | Hemorrhoidectomy | | |
| | Cholecystectomy (gall bladder removal) | | |
| | Kidney transplant | | |
| | Nephrectomy | | |
| | Radical prostatectomy | | |
| | Nephrectomy | | |
| | Gastrectomy | | |
| | Small bowel resection | | |
| | Splenectomy | | |
| | Incisional hernia repair | Transverse abdominus plane (TAP) | |
| | Inguinal hernai repair | | |
| | Sigmoidectomy | | |
| | Liver resection | | |
| | Enterostomy | | |
| | Rectum resection | | |
| | Kidney stone removal | | |
| | Cystectomy (urinary bladder removal) | | |
| Throat | Tonsillectomy | | |
| | Submucosal resection/reconstruction of nasal septum | | |

*FIG. 28B*

| | Surgical Procedure | Nerve target(s) | Anatomical Access/ Placement |
|---|---|---|---|
| Ear, Nose & | Rhinoplasty | | |
| | Sinus (sinusitus) | | |
| | Inner ear surgery | | |
| | Parotidectomy | | |
| | Submandibular gland surgery | | |
| Oral & Maxillofacial | Dentoalveolar | | |
| | Dental implant | | |
| | Orthognathic jaw | | |
| | Temporomandibular joint (TMJ) | | |
| | Reconstruction | | |
| Oncology | Tumor resection | | |
| Cosmetic | Liposuction | | |

*FIG. 28C*

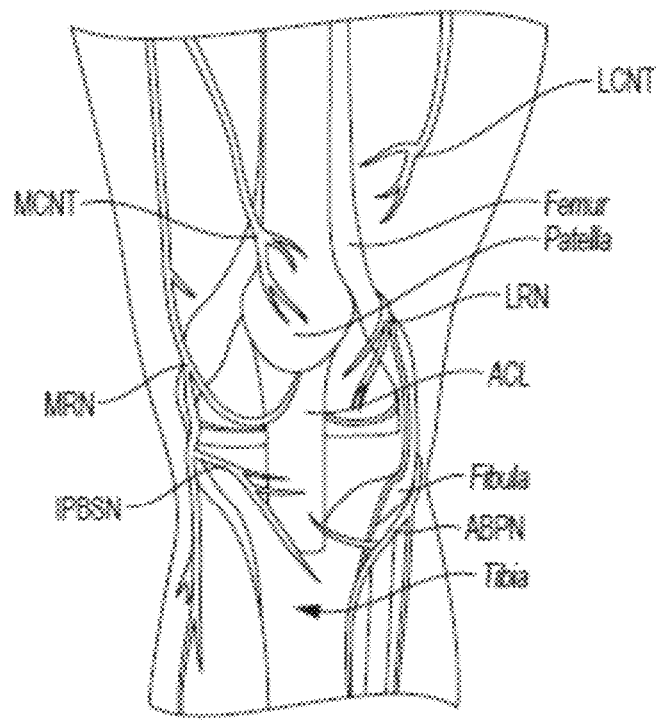
FIG. 29A
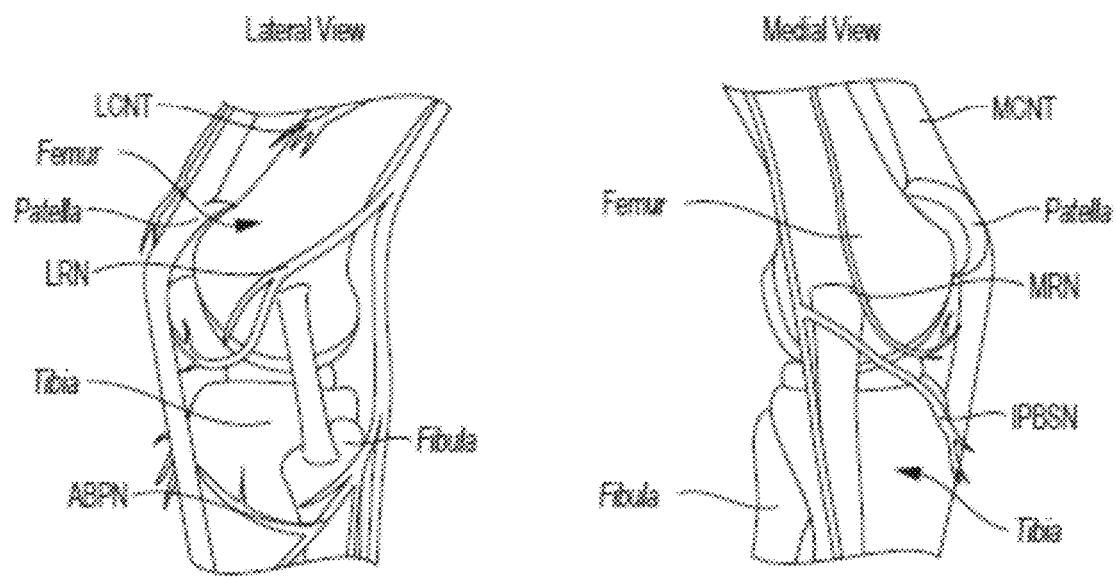
FIG. 29B
FIG. 29C

IMPLANTABLE DEPOTS FOR THE CONTROLLED RELEASE OF THERAPEUTIC AGENTS

CROSS-REFERENCE TO RELATED APPLICATIONS

The present application is a continuation of U.S. patent application Ser. No. 17/248,949, filed Feb. 15, 2021; which is a continuation of U.S. patent application Ser. No. 16/840,215, filed Apr. 3, 2020; which is a continuation of International Application No. PCT/US2018/054777, filed Oct. 6, 2018; which claims the benefit of priority to U.S. Application No. 62/569,349, filed Oct. 6, 2017; U.S. Application No. 62/670,721, filed May 12, 2018; U.S. Application No. 62/640,571, filed Mar. 8, 2018; and U.S. Application No. 62/723,478, filed Aug. 28, 2018, each of which is incorporated by reference herein in its entirety.

TECHNICAL FIELD

The present technology relates to implants for controlled, sustained release of therapeutic agents in vivo.

BACKGROUND OF THE INVENTION

Implantable systems for the controlled release of therapeutic agents offer advantages over other drug delivery methods, such as oral or parenteral methods. Devices comprised of biocompatible and/or biodegradable polymers and therapeutic agents can be implanted in clinically desirable anatomic locations, thereby providing localized delivery of select agents. This localized delivery enables a substantial proportion of the agent to reach the intended target and undesirable systemic side effects can be avoided. However, these systems often suffer from a lack of a true controlled release mechanism in that they typically provide a burst of drug upon contact with surrounding physiologic fluids followed by a residual release of drug.

In order to improve drug release in certain polymer carriers, hydrophilic polymers, such as polysorbate, have been added to these carriers as wetting agents to accelerate or to enhance drug release from biocompatible polymers such polyethylene glycol (PEG) in oral formulations (Akbari, J., et al., ADV. PHARM. BULL., 2015, 5(3): 435-441). However, these formulations are intended to provide an immediate release of a hydrophobic drug into a hydrophilic environment (the in vivo physiologic fluid), where a substantial portion of the entire drug payload is immediately or aggressively released, not a variable or sustained control release.

While these drug release kinetics may be desirable in some clinical applications, a controlled, sustained release of a therapeutic agent can be of clinical benefit in certain circumstances. In particular, it may be desirable to implant a biodegradable carrier holding a large dose of a therapeutic agent for a controlled, sustained release over time. This may have particular value when the carrier loaded with therapeutic agent is implanted in conjunction with an interventional or surgical procedure and, optionally, alongside or as part of an implantable medical device.

Xaracoll® (Innocoll Technologies, Athlone, Ireland) is an example of a sustained-release system for postoperative pain therapy. Xaracoll® is an implantable collagen sponge loaded with bupivacaine for extended release to achieve a local pain block in the surgical field. As shown in FIG. 1, the bupivacaine HCl concentration in plasma peaked within 15 hours of implantation, thereby illustrating a duration of effect that is inadequate.

Thus, a need exists for biocompatible implantable systems capable of providing a highly controlled release of drug.

SUMMARY

The present technology relates to implants for controlled release of a therapeutic agent to treat a medical condition and associated systems and methods. In particular, the present technology relates to implants for local, sustained release of a therapeutic agent at a surgical or interventional site and associated systems and methods.

The subject technology is illustrated, for example, according to various aspects described below, including with reference to FIGS. 1-32. Various examples of aspects of the subject technology are described as numbered clauses (1, 2, 3, etc.) for convenience. These are provided as examples and do not limit the subject technology.

1. A depot for the treatment of postoperative pain via sustained, controlled release of an analgesic, comprising:
   a therapeutic region comprising the analgesic;
   a control region comprising a bioresorbable polymer and a releasing agent mixed with the polymer, wherein the releasing agent is configured to dissolve when the depot is placed in vivo to form diffusion openings in the control region; and
   wherein the depot is configured to be implanted at a treatment site in vivo and, while implanted, release the analgesic at the treatment site for no less than 7 days.

2. The depot of Clause 1, wherein the analgesic in the therapeutic region comprises at least 50% of the total weight of the depot.

3. The depot of Clause 1 or Clause 2, wherein the depot is configured to release the analgesic at the treatment site for no less than 14 days.

4. The depot of Clause 3, wherein about 20% to about 50% of the analgesic is released in the first about 3 to about 5 days of the 14 days, and wherein at least 80% of the remaining analgesic is released in the last 11 days of the 14 days.

5. The depot of Clause 3, wherein about 20% to about 40% of the analgesic is released in the first 3 days of the 14 days, and wherein at least 80% of the remaining analgesic is released in the last 11 days of the 14 days.

6. The depot of any one of Clauses 3 to 5, wherein at least 90% of the remaining analgesic is released in the last 11 days of the 14 days.

7. The depot of any one of Clauses 3 to 6, wherein no more than 15% of the amount of analgesic is released in the first 2 days of the 14 days.

8. The depot of any one of Clauses 3 to 7, wherein no more than 20% of the amount of analgesic is released in the first 2 days of the 14 days.

9. The depot of any one of Clauses 3 to 8, wherein no more than 25% of the amount of analgesic is released in the first 3 days of the 14 days.

10. The depot of any one of Clauses 3 to 9, wherein no more than 30% of the amount of analgesic is released in the first 3 days of the 14 days.

11. The depot of any one of Clauses 1 to 11, wherein the depot is configured to release the analgesic at a first rate for a first period of time and at a second rate for a second period of time.

12. The depot of Clause 12, wherein the first rate is greater than the second rate.

13. The depot of Clause 12, wherein the first period of time is greater than the second period of time.

14. The depot of Clause 12, wherein the first period of time is less than the second period of time.

15. The depot of any one of Clauses 1 to 14, wherein the depot is configured to release at least 90% of the analgesic in the therapeutic region within 14 days.

16. The depot of any one of Clauses 1 to 15, wherein the depot is configured to release about 100 mg to about 500 mg of analgesic to the treatment site per day.

17. The depot of any one of Clauses 1 to 16, wherein the depot is configured to release about 100 mg to about 400 mg of analgesic to the treatment site per day.

18. The depot of any one of Clauses 1 to 17, wherein the depot is configured to release about 100 mg to about 300 mg of analgesic to the treatment site per day.

19. The depot of any one of Clauses 1 to 18, wherein the depot is configured to release no more than 300 mg of analgesic per day within the first 3 days, and no more than 200 mg per day in the remaining days.

20. The depot of any one of Clauses 1 to 19, wherein the depot is configured to release no more than 150 mg of analgesic per day within the first 3 days, and no more than 100 mg per day in the remaining days.

21. The depot of any one of Clauses 1 to 20, wherein no more than 400 mg of analgesic is released within any day of the 14 days.

22. The depot of any one of Clauses 1 to 21, wherein no more than 300 mg of analgesic is released within any day of the 14 days.

23. The depot of any one of Clauses 1 to 22, wherein no more than 250 mg of analgesic is released within any day of the 14 days.

24. The depot of any one of Clauses 1 to 23, wherein no more than 200 mg of analgesic is released within any day of the 14 days.

25. The depot of any one of Clauses 1 to 24, wherein no more than 150 mg of analgesic is released within any day of the 14 days.

26. The depot of any one of Clauses 1 to 25, wherein no more than 100 mg of analgesic is released within any day of the 14 days.

27. The depot of any one of Clauses 1 to 26, wherein the depot is configured to release the analgesic agent at the treatment site in vivo for no less than 1 day, no less than 2 days, no less than 3 days, no less than 4 days, no less than 5 days, no less than 6 days, no less than 7 days, no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 200 days, no less than 300 days, or no less than 365 days.

28. The depot of any one of Clauses 1 to 27, wherein the concentration of the analgesic in the blood plasma of a mammalian patient on day 10 is no less than 70% of the concentration of the analgesic in the blood plasma of the patient on day 5.

29. The depot of any one of Clauses 1 to 28, wherein the therapeutic region comprises a covered portion and an exposed portion, wherein the covered portion is covered by the control region such that, when the depot is initially positioned at the treatment site in vivo, the control region is between the covered portion of the therapeutic region and physiologic fluids at the treatment site and the exposed portion of the therapeutic region is exposed to the physiologic fluids.

30. The depot of any one of Clauses 1 to 29, wherein,
the depot has a total surface area comprising the exposed surface area of the cover region plus the exposed surface area of the therapeutic region, and
when the depot is initially positioned at the treatment site in vivo, a ratio of the exposed surface area of the therapeutic region to the exposed surface area of the cover region is from about 5% to about 20%, or from about 5% to about 15%, or from about 5% to about 10%.

31. The depot of Clause 30, wherein the exposed surface area of the control region is less than the exposed surface area of the therapeutic region.

32. The depot of Clause 30, wherein the exposed surface area of the control region is greater than the exposed surface area of the therapeutic region.

33. The depot of any one of Clauses 1 to 32, wherein the control region is a first control region, and wherein the depot comprises a second control region.

34. The depot of Clause 33, wherein the first control region is disposed at a first side of the therapeutic region and the second control region is disposed at a second side of the therapeutic region opposite the first side.

35. The depot of any one of Clauses 1 to 34, wherein the depot comprises a plurality of control regions and a plurality of therapeutic regions, and wherein each of the therapeutic regions is separated from an adjacent one of the therapeutic regions by one or more control regions.

36. The depot of Clause 35, wherein each of the therapeutic regions and each of the control regions is a micro-thin layer.

37. The depot of Clause 35 or Clause 36, wherein the depot comprises from about 2 to about 100 therapeutic regions.

38. The depot of Clause 35 or Clause 36, wherein the depot comprises from about 2 to about 50 therapeutic regions.

39. The depot of Clause 35 or Clause 36, wherein the depot comprises from about 2 to about 10 therapeutic regions.

40. The depot of any one of Clauses 1 to 34, wherein the therapeutic region is enclosed by the control region such that, when the depot is positioned at the treatment site in vivo, the control region is between the therapeutic region and physiologic fluids at the treatment site.

41. The depot of any one of Clauses 1 to 40, wherein the control region comprises a first control layer and a second control layer.

42. The depot of Clause 41, wherein the second control layer is adjacent to the therapeutic region and the first control layer encapsulates/encloses the therapeutic region and the second control layer.

43. The depot of Clause 41 or Clause 42, wherein the first control layer and the second control layer together enclose the therapeutic region.

44. The depot of any one of Clauses 41 to 43, wherein the first control layer is disposed at a first side of the therapeutic region and the second control layer is disposed at a second side of the therapeutic region opposite the first side.

45. The depot of any one of Clauses 41 to 44, wherein the first control layer comprises a first plurality of sub-layers and the second control layer comprises a second plurality of sub-layers.

46. The depot of any one of Clauses 41 to 45, wherein the first control layer includes a first amount of the releasing agent and the second control layer includes a second amount of the releasing agent different than the first amount.

47. The depot of any one of Clauses 41 to 46, wherein the second control layer is positioned between the first control layer and the therapeutic region, and wherein the first control layer includes a first concentration of the releasing agent and the second control layer includes a second concentration of the releasing agent greater than the first concentration.

48. The depot of any one of Clauses 41 to 46, wherein the second control layer is positioned between the first control layer and the therapeutic region, and wherein the first control layer includes a first concentration of the releasing agent and the second control layer includes a second concentration of the releasing agent less than the first concentration.

49. The depot of any one of Clauses 41 to 48, wherein the second control layer is positioned between the first control layer and the therapeutic region, and wherein
the first control layer includes up to 5% by weight of the releasing agent, up to 10% by weight of the releasing agent, up to 15% by weight of the releasing agent, up to 20% by weight of the releasing agent, up to 25% by weight of the releasing agent, up to 30% by weight of the releasing agent, up to 35% by weight of the releasing agent, up to 40% by weight of the releasing agent, up to 45% by weight of the releasing agent, or 50% by weight of the releasing agent.
the second control layer includes up to 5% by weight of the releasing agent, up to 10% by weight of the releasing agent, up to 15% by weight of the releasing agent, up to 20% by weight of the releasing agent, up to 25% by weight of the releasing agent, up to 30% by weight of the releasing agent, up to 35% by weight of the releasing agent, up to 40% by weight of the releasing agent, up to 45% by weight of the releasing agent, or up to 50% by weight of the releasing agent.

50. The depot of any one of Clauses 41 to 49, wherein the second control layer is positioned between the first control layer and the therapeutic region, and wherein the first control layer includes a first amount of the releasing agent and the second control layer includes a second amount of the releasing agent, the second amount being at least 2×, at least 3×, at least 4×, or at least 5× the first amount.

51. The depot of any one of Clauses 1 to 50, wherein a thickness of the control region is less than or equal to 1/50 of a thickness of the therapeutic region.

52. The depot of any one of Clauses 1 to 50, wherein a thickness of the control region is less than or equal to 1/75 of a thickness of the therapeutic region.

53. The depot of any one of Clauses 1 to 50, wherein a thickness of the control region is less than or equal to 1/100 of a thickness of the therapeutic region.

54. The depot of any one of Clauses 1 to 53, wherein the depot is a flexible solid that is structurally capable of being handled by a clinician during the normal course of a surgery without breaking into multiple pieces and/or losing its general shape.

55. The depot of any one of Clauses 1 to 54, wherein the depot is configured to be placed in the knee of a patient and release the analgesic in vivo for up to 7 days without breaking into multiple pieces.

56. The depot of any one of Clauses 1 to 55, wherein the depot has a width and a thickness, and wherein a ratio of the width to the thickness is 21 or greater.

57. The depot of Clause 56, wherein the ratio is 30 or greater.

58. The depot of Clause 56, wherein the ratio is 40 or greater.

59. The depot of any one of Clauses 1 to 58, wherein the depot has a surface area and a volume, and wherein a ratio of the surface area to volume is at least 1.

60. The depot of any one of Clauses 1 to 59, wherein the diffusion openings include at least one or more pores and/or one or more channels.

61. The depot of any one of Clauses 1 to 60, wherein the two or more micro-thin layers of the bioresorbable polymer are bonded via heat compression to form the therapeutic region.

62. The depot of any one of Clauses 1 to 61, wherein the control region and the therapeutic region are bonded via heat compression.

63. The depot of any one of Clauses 1 to 62, wherein the control region and the therapeutic region are thermally bonded.

64. The depot of any one of Clauses 1 to 63, wherein dissolution of the releasing agent following in vivo placement in the treatment site causes the control region and the therapeutic region to transition from a state of lesser porosity to a state of greater porosity to facilitate the release of the analgesic from the depot.

65. The depot of any one of Clauses 1 to 64, wherein the control region does not include the analgesic at least prior to implantation of the depot at the treatment site.

66. The depot of any one of Clauses 1 to 64, wherein the control region comprises an analgesic different from the analgesic in the therapeutic region.

66a. The depot of any one of Clauses 1 to 66, wherein the therapeutic region does not include any releasing agent prior to implantation of the depot at the treatment site.

67. The depot of any one of Clauses 1 to 66a, wherein the releasing agent is a first releasing agent and the therapeutic region includes a second releasing agent mixed with the analgesic.

68. The depot of any one of Clauses 1 to 67, wherein the releasing agent is a first releasing agent and the polymer is a first polymer, and the therapeutic region includes a second releasing agent and a second polymer mixed with the analgesic.

69. The depot of any one of Clauses 1 to 68, wherein the first releasing agent is the same as the second releasing agent.

70. The depot of any one of Clauses 1 to 68, wherein the first releasing agent is the different than the second releasing agent.

71. The depot of any one of Clauses 1 to 70, wherein a concentration of the first releasing agent within the control region is the greater than a concentration of the second releasing agent within the therapeutic region.

72. The depot of any one of Clauses 1 to 70, wherein a concentration of the first releasing agent within the control region is the less than a concentration of the second releasing agent within the therapeutic region.

73. The depot of any one of Clauses 1 to 70, wherein a concentration of the first releasing agent within the control region is the same as a concentration of the second releasing agent within the therapeutic region.

74. The depot of any one of Clauses 1 to 72, wherein a concentration of the first releasing agent within the control region is different than a concentration of the second releasing agent within the therapeutic region.

75. The depot of any one of Clauses 1 to 74, wherein the therapeutic region includes a plurality of microlayers.

76. The depot of any one of Clauses 1 to 75, wherein the mass of the analgesic comprises at least 50% of the mass of the depot.

77. The depot of any one of Clauses 1 to 76, wherein the ratio of the mass of the analgesic in the depot to the depot polymer mass is at least 3:1.

78. The depot of any one of Clauses 1 to 76, wherein the ratio of the mass of the analgesic in the depot to the depot polymer mass is at least 4:1.

79. The depot of any one of Clauses 1 to 76, wherein the ratio of the mass of the analgesic in the depot to the depot polymer mass is at least 5:1.

80. The depot of any one of Clauses 1 to 76, wherein a ratio of the mass of the analgesic in the depot to the depot polymer mass is at least 6:1.

81. The depot of any one of Clauses 1 to 76, wherein a ratio of the mass of the analgesic in the depot to the depot polymer mass is at least 7:1.

82. The depot of any one of Clauses 1 to 76, wherein a ratio of the mass of the analgesic in the depot to the depot polymer mass is at least 8:1.

83. The depot of any one of Clauses 1 to 76, wherein a ratio of the mass of the analgesic in the depot to the depot polymer mass is at least 10:1.

84. The depot of any one of Clauses 1 to 76, wherein a ratio of the mass of the analgesic in the depot to the depot polymer mass is at least 16:1.

85. The depot of any one of Clauses 1 to 84, wherein the therapeutic region includes at least 60% by weight of the analgesic, 60% by weight of the analgesic, at least 70% by weight of the analgesic, at least 80% by weight of the analgesic, at least 90% by weight of the analgesic, or 100% by weight of the analgesic.

86. The depot of any one of Clauses 1 to 84, wherein the depot includes at least 15% by weight of the analgesic, at least 20% by weight of the analgesic, at least 30% by weight of the analgesic, at least 40% by weight of the analgesic, at least 50% by weight of the analgesic, at least 60% by weight of the analgesic, at least 70% by weight of the analgesic, at least 80% by weight of the analgesic, at least 90% by weight of the analgesic, or 100% by weight of the analgesic.

87. The depot of any one of Clauses 1 to 86, wherein the analgesic comprises at least one of: simple analgesics, local anesthetics, NSAIDs and opioids.

88. The depot of any one of Clauses 1 to 87, wherein the analgesic comprises a local anesthetic selected from at least one of bupivacaine, ropivacaine, mepivacaine, and lidocaine.

89. The depot of any one of Clauses 1 to 88, further comprising an antibiotic, an antifungal, and/or an antimicrobial, wherein the antibiotic, the antifungal, and/or the antimicrobial is selected from at least one of amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, and α-protegrins, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, and amphotericin B.

90. The depot of any one of Clauses 1 to 89, further comprising an anti-inflammatory agent selected from at least one of steroids, prednisone, betamethasone, cortisone, dexamethasone, hydrocortisone and methylprednisolone, nonsteroidal anti-inflammatory drugs (NSAIDs), aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, and COX-2 inhibitors.

91. The depot of any one of Clauses 1 to 90, further comprising at least one of: epinephrine, clonidine, transexamic acid.

92. The depot of any one of Clauses 1 to 91, wherein the releasing agent is a non-ionic surfactant.

93. The depot of any one of Clauses 1 to 92, wherein the releasing agent has hydrophilic properties.

94. The depot of any one of Clauses 1 to 93, wherein the releasing agent is a polysorbate.

95. The depot of any one of Clauses 1 to 94, wherein the releasing agent is Tween 20.

96. The depot of any one of Clauses 1 to 94, wherein the releasing agent is Tween 80.

97. The depot of any one of Clauses 1 to 96, wherein the releasing agent is non-polymeric.

98. The depot of any one of Clauses 1 to 97, wherein the releasing agent is not a plasticizer.

99. The depot of any one of Clauses 1 to 98, wherein the polymer is configured to degrade only after substantially all of the analgesic has been released from the depot.

100. The depot of any one of Clauses 1 to 99, wherein the polymer is a copolymer.

101. The depot of any one of Clauses 1 to 99, wherein the polymer is a terpolymer.

102. The depot of any one of Clauses 1 to 101, wherein the polymer includes at least one of polyglycolide (PGA), polycaprolactone (PCL), poly(DL-lactic acid) (PLA), poly(alpha-hydroxy acids), poly(lactide-co-glycolide)(PLGA or DLG), poly(DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(glycolide-trimethylene carbonate), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, and poly(DL-lactide-co-glycolide-co-caprolactone).

103. The depot of any one of Clauses 1 to 102, wherein the polymer is one of poly(DL-lactide-co-glycolide-co-caprolactone) and poly(DL-lactide-co-glycolide)(PLGA).

104. The depot of any one of Clauses 1 to 102, wherein the polymer is poly(DL-lactide-co-glycolide-co-caprolactone) in a molar ratio of 60:30:10.

105. The depot of any one of Clauses 1 to 102, wherein the polymer is poly(DL-lactide-co-glycolide)(PLGA) in a molar ratio of 50:50.

106. The depot of any one of Clauses 1 to 105, wherein the polymer is ester-terminated.

107. The depot of any one of Clauses 1 to 102, wherein the polymer is a terpolymer that includes three polymers selected from the following: polyglycolide (PGA), polycaprolactone (PCL), poly(L-lactic acid) (PLA), poly(DL-lactic acid) (PLA), poly(trimethylene carbonate) (PTMC), polydioxanone (PDO), poly(4-hydroxy butyrate) (PHB), polyhydroxyalkanoates (PHA), poly(phosphazene), and polyethylene glycol.

108. The depot of any one of Clauses 1 to 107, wherein the polymer is a first polymer, and the therapeutic region includes a second polymer mixed with the analgesic.

109. The depot of Clause 108, wherein the first polymer and the second polymer are the same.

110. The depot of Clause 108, wherein the first polymer and the second polymer are different.

111. The depot of any one of Clauses 108 to 110, wherein the first polymer and/or the second polymer include at least one of polyglycolide (PGA), polycaprolactone (PCL), poly (DL-lactic acid) (PLA), poly(alpha-hydroxy acids), poly (lactide-co-glycolide)(PLGA or DLG), poly(DL-lactide-co-caprolactone) (DL-PLCL), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(ethyl glutamate-co-glutamic acid), poly(tert-butyloxy-carbonylmethyl glutamate), poly (glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, poly (DL-lactide-co-glycolide-co-caprolactone).

112. The depot of any one of Clauses 108 to 111, wherein the first polymer and/or the second polymer selected from the following: poly(DL-lactide-co-glycolide-co-caprolactone) and poly(DL-lactide-co-glycolide)(PLGA).

113. The depot of any one of Clauses 108 to 111, wherein the first polymer and/or the second polymer is poly(DL-lactide-co-glycolide-co-caprolactone) and has a molar ratio of 60:30:10.

114. The depot of any one of Clauses 108 to 111, wherein the first polymer and/or the second polymer is poly(DL-lactide-co-glycolide) and has a molar ratio of 50:50.

115. The depot of any one of Clauses 108 to 114, wherein the first polymer and/or the second polymer is ester-terminated.

116. The depot of any one of Clauses 108 to 111, wherein the first polymer and/or the second polymer is a terpolymer that includes three polymers selected from the following: polyglycolide (PGA), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), and polyethylene glycol.

117. The depot of any one of Clauses 1 to 116, wherein the ratio of the releasing agent to the polymer in the control region is at least 1:1.

118. The depot of any one of Clauses 1 to 116, wherein the ratio of the releasing agent to the polymer in the control region is at least 2:1.

119. The depot of any one of Clauses 1 to 116, wherein the ratio of the releasing agent to the polymer in the control region is at least 3:1.

120. The depot of any one of Clauses 1 to 116, wherein the ratio of the releasing agent to the polymer in the control region is at least 4:1.

121. The depot of any one of Clauses 1 to 116, wherein the ratio of the releasing agent to the polymer in the control region is at least 5:1.

122. The depot of any one of Clauses 1 to 116, wherein the ratio of the releasing agent to the polymer in the control region is at least 6:1.

123. The depot of any one of Clauses 1 to 116, wherein the ratio of the releasing agent to the polymer in the control region is at least 7:1.

124. The depot of any one of Clauses 1 to 116, wherein the ratio of the releasing agent to the polymer in the control region is at least 8:1.

125. The depot of any one of Clauses 1 to 116, wherein the ratio of the releasing agent to the polymer in the control region is at least 9:1.

126. The depot of any one of Clauses 1 to 116, wherein the ratio of the releasing agent to the polymer in the control region is at least 10:1.

127. The depot of any one of Clauses 1 to 116, wherein the ratio of the releasing agent to the polymer in the control region is at least 15:1.

128. The depot of any one of Clauses 1 to 127, wherein:
the polymer is a first polymer and the therapeutic region further includes a second polymer,
the depot has a depot polymer mass equivalent to a mass of the first polymer plus a mass of the second polymer, and
a ratio of a mass of the analgesic in the depot to the depot polymer mass is approximately 1:1.

129. The depot of Clause 128, wherein the first polymer is the same as the second polymer.

130. The depot of Clause 128, wherein the first polymer is different than the second polymer.

131. The depot of any one of Clauses 128 to 130, wherein the ratio of the mass of the analgesic in the depot to the depot polymer mass is at least 2:1.

132. The depot of any one of Clauses 128 to 130, wherein the ratio of the mass of the analgesic in the depot to the depot polymer mass is at least 3:1.

133. The depot of any one of Clauses 128 to 130, wherein the ratio of the mass of the analgesic in the depot to the depot polymer mass is at least 4:1.

134. The depot of any one of Clauses 128 to 130, wherein the ratio of the mass of the analgesic in the depot to the depot polymer mass is approximately 5:1.

135. The depot of any one of Clauses 128 to 130, wherein a ratio of the mass of the analgesic in the depot to the depot polymer mass is at least 6:1.

136. The depot of any one of Clauses 128 to 130, wherein a ratio of the mass of the analgesic in the depot to the depot polymer mass is at least 7:1.

137. The depot of any one of Clauses 128 to 130, wherein a ratio of the mass of the analgesic in the depot to the depot polymer mass is at least 8:1.

138. The depot of any one of Clauses 128 to 130, wherein a ratio of the mass of the analgesic in the depot to the depot polymer mass is at least 10:1.

139. The depot of any one of Clauses 128 to 130, wherein a ratio of the mass of the analgesic in the depot to the depot polymer mass is at least 16:1.

140. The depot of any one of Clauses 1 to 139, wherein the analgesic is a local anesthetic, and wherein the release of the analgesic to the treatment site over the five days inhibits the growth of bacteria and fungi.

141. The depot of Clause 140, wherein depot is configured to inhibit the growth of bacteria and fungi such that a number of bacteria on the depot is 10×, 20×, 30×, 40×, or 50× less than a number of bacteria present on a comparable depot containing no analgesic.

142. The depot of any one of Clauses 1 to 141, wherein the release of analgesic is at a level sufficiently high to create a sensory block, thereby treating postoperative pain, but sufficiently low to avoid a motor block.

143. The depot of any one of Clauses 1 to 142, wherein the release of the analgesic provides motor sparing relief from postoperative pain.

144. A depot for sustained, controlled release of a therapeutic agent, comprising:
a therapeutic region comprising the therapeutic agent;
a control region comprising a bioresorbable polymer and a releasing agent mixed with the polymer, wherein the releasing agent is configured to dissolve when the depot is placed in contact with a fluid to form diffusion openings in the control region; and
wherein, when the depot is placed in contact with a fluid, the depot is configured to release the therapeutic agent into the surrounding fluid for no less than 14 days, and
wherein about 20% to about 50% of the therapeutic agent is released in the first about 3 to about 5 days of the 14 days, and wherein at least 80% of the remaining therapeutic agent is released in the last 11 days of the 14 days.

145. The depot of Clause 144, wherein at least 85% of the remaining therapeutic agent is released in the last 11 days of the 14 days.

146. The depot of Clause 144, wherein at least 90% of the remaining therapeutic agent is released in the last 11 days of the 14 days.

147. The depot of Clause 144, wherein at least 95% of the remaining therapeutic agent is released in the last 11 days of the 14 days.

148. The depot of any one of Clauses 144 to 147, wherein no more than 15% of the amount of therapeutic agent is released in the first 2 days of the 14 days.

149. The depot of any one of Clauses 144 to 147, wherein no more than 20% of the amount of therapeutic agent is released in the first 2 days of the 14 days.

150. The depot of any one of Clauses 144 to 147, wherein no more than 25% of the amount of therapeutic agent is released in the first 3 days of the 14 days.

151. The depot of any one of Clauses 144 to 147, wherein no more than 30% of the amount of therapeutic agent is released in the first 3 days of the 14 days.

152. The depot of any one of Clauses 144 to 147, wherein the releasing agent is configured to dissolve when the depot is placed in contact with phosphate buffered saline to form diffusion openings.

153. A method for treating postoperative pain, comprising:
positioning a depot at a treatment site in vivo having physiologic fluids, the depot comprising (a) a control region including a bioresorbable polymer and a releasing agent mixed with the polymer, and (b) a therapeutic region including at least 50% by weight of an analgesic; and
releasing analgesic from the depot to the treatment site for no less than seven days.

154. The method of Clause 153, further comprising dissolving the releasing agent at a first rate and degrading the polymer at a second rate, wherein the first rate is greater than the second rate.

155. The method of Clause 153 or Clause 154, further comprising dissolving the releasing agent in response to contact between the control region and the physiologic fluids at the treatment site.

156. The method of any one of Clauses 153 to 155, further comprising creating diffusion openings in the control region via the dissolution of the releasing agent in response to physiologic fluids at the treatment site.

157. The method of any one of Clauses 153 to 156, wherein the releasing agent is a first releasing agent and the therapeutic region includes a second releasing agent, and wherein the method further comprises creating microchannels in the therapeutic region and the control region via dissolution of the first and/or second releasing agents.

158. The method of any one of Clauses 153 to 157, wherein at least some of the microchannels penetrate both the therapeutic region and the control region.

159. The method of any one of Clauses 153 to 158, wherein the therapeutic region comprises a plurality of microlayers, and wherein at least some of the microchannels extend through consecutive microlayers.

160. The method of any one of Clauses 153 to 159, wherein the control region comprises a first plurality of microlayers and the therapeutic region comprises a second plurality of microlayers, and wherein at least some of the microchannels extend through the first and second plurality of microlayers.

161. The method of any one of Clauses 153 to 160, further including increasing a porosity of the depot via dissolution of the releasing agent.

162. The method of any one of Clauses 153 to 161, wherein the analgesic is released one or more times in substantially discrete doses after implantation.

163. The method of any one of Clauses 153 to 162, wherein the analgesic is released continuously for at least seven days after implantation.

164. The method of any one of Clauses 153 to 163, wherein the analgesic is released for no less than 10 days.

165. The method of any one of Clauses 153 to 163, wherein the analgesic is released for no less than 14 days.

166. The method of any one of Clauses 153 to 165, wherein no more than 20% of the amount of analgesic is released in the first day of the seven days.

167. The method of any one of Clauses 153 to 166, further comprising securing the depot to the treatment site via an attachment means.

168. The method of any one of Clauses 153 to 167, wherein the attachment means is coupled to the depot prior to implantation.

169. The method of any one of Clauses 153 to 168, wherein the depot is a first depot and the method further comprises positioning a second depot at the treatment site.

170. The method of Clause 169, wherein the first and second depots together release at least 1400 mg of the analgesic to the treatment site over a period of no less than seven days.

171. A method for treating postoperative pain associated with orthopedic surgery with any of the depots of Clauses 1 to 152 and 196 to 198 and/or systems of Clauses 179 to 195.

172a. A method for treating postoperative pain in a patient following orthopedic surgery, the method comprising:
implanting a plurality of depots at a site of the surgery, each of the depots comprising (a) a control region including a bioresorbable polymer and a releasing agent mixed with the polymer, and (b) a therapeutic region including at least 50% by weight of an analgesic; and
releasing analgesic from the depot to the site for no less than seven days.

172b. A method for treating postoperative pain in a patient following orthopedic surgery, the method comprising:
implanting a depot at a site of the surgery, the depot comprising (a) a control region including a bioresorbable polymer and a releasing agent mixed with the polymer, and (b) a therapeutic region including at least 50% by weight of an analgesic; and
releasing analgesic from the depot to the site for no less than seven days.

172c. A method for treating postoperative pain in a patient following total knee arthroplasty, comprising:
positioning a depot in a knee of the patient, the depot comprising (a) a control region including a bioresorbable polymer and a releasing agent mixed with the polymer, and (b) a therapeutic region including at least 50% by weight of an analgesic; and
releasing analgesic from the depot to the patient's knee for no less than seven days.

172a. The method of Clause 172, wherein the depot is any of the depots of Clauses 1 to 152 and 196 to 198.

173. The method of Clause 172 or Clause 172a, wherein positioning the depot comprises placing at least one depot in at least one of: suprapatellar pouch, lateral gutter, medial gutter, posterior capsule, quadricep tendon, skin incision, arthrotomy, adductor canal, saphenous nerve, genicular nerve.

174. The method of any one of Clauses 172 to 173, wherein positioning the depot comprises positioning at least one depot adjacent at least one of a saphenous nerve, an adductor canal, and a femoral nerve.

175. The method of any one of Clauses 172 to 174, wherein positioning the depot comprises intracapsular placement of at least one depot.

176. The method of any one of Clauses 172 to 174, wherein positioning the depot comprises extracapsular placement of at least one depot.

177. The method of any one of Clauses 172 to 176, wherein positioning the depot comprises intracapsular placement without interfering with articulation of the knee.

178. The method of Clause 172, wherein placing at least one depot at at least one of: suprapatellar pouch, lateral gutter, medial gutter, posterior capsule, quadricep tendon, skin incision, arthrotomy, adductor canal.

179. A system for treating postoperative pain associated with orthopedic surgery, the system comprising:
a plurality of depots, each of which is any of the depots described in the previous Clauses, wherein the plurality of depots are configured to be implanted at a treatment site of a patient and release the analgesic to the treatment site.

180. The system of Clause 179, wherein the depots are configured to release analgesic to the treatment site for at least 7 days, at least 8 days, at least 9 days, at least 10 days, at least 11 days, at least 12 days, at least 13 days, or at least 14 days.

181. The system of Clause 180, wherein the depots are configured to collectively release no more than 250 mg of analgesic per day within the first 3 days, and no more than 150 mg per day in the remaining days.

182. A system for treating postoperative pain, comprising:
a delivery system; and
a depot configured to be implanted at a treatment site in vivo with the delivery system, wherein the depot comprises any of the depots of Clauses 1 to 152 and 196 to 198.

182a. A system for treating postoperative pain, comprising:
an attachment means; and
a depot configured to be implanted at a treatment site in vivo and secured at the treatment site via the attachment means, wherein the depot comprises any of the depots of Clauses 1 to 152 and 196 to 198.

183. The system of Clause 182a, wherein the attachment means is coupled to the depot prior to implantation.

184. The system of Clause 182 or Clause 183, wherein the attachment means is at least one of a suture, a tine, a barb, a hook, and a screw.

185. The system of any one of Clauses 182a to 184, wherein the pain is associated with orthopedic surgery.

186. The system of any one of Clauses 182a to 185, wherein the pain is associated with joint replacement surgery.

187. The system of any one of Clauses 182a to 186, wherein the pain is associated with a knee replacement surgery.

188. The system of Clause 187, wherein the pain is associated with a partial knee replacement surgery.

189. The system of Clause 187, wherein the pain is associated with a total knee replacement surgery.

190. The system of Clause 187, wherein the pain is associated with a revision surgery of a knee replacement surgery.

191. The system of any one of Clauses 182a to 190, wherein the depot is configured to be positioned adjacent at least one of a saphenous nerve, an adductor canal, and a femoral nerve.

192. The system of any one of Clauses 182a to 191, wherein the depot is configured to be positioned adjacent at least one of a posterior capsule of the knee, a superior region of the patella, or an incision into the knee capsule.

193. The system of any one of Clauses 182a to 191, wherein the depot is configured to be positioned within the knee capsule within the medial and/or lateral gutters.

194. A system for treating postoperative pain, comprising a delivery system and any of the depots of Clauses 1 to 152 and 196 to 198.

195. A system for treating postoperative pain, comprising a plurality of depots, any of which comprising any of the depots of Clauses 1 to 152 and 196 to 198.

196. A depot for the release of a therapeutic agent to treat or manage a particular condition or disease, comprising:
a therapeutic region comprising the therapeutic agent and a bioresorbable polymer carrier;
a control region comprising a bioresorbable polymer layer and a releasing agent mixed with the polymer, wherein the releasing agent is configured to dissolve over a first period of time following in vivo placement to form diffusion openings in the control region; and
wherein the depot is configured to be implanted at a treatment site in vivo and, while implanted, release the therapeutic agent at the treatment site for a second period of time;
wherein the second period of time is greater than the first period of time;
wherein following the second period of time the polymer carrier of the therapeutic region and the polymer layer of the control region comprise a highly porous polymer structure configured to degrade in vivo without core acidification.

197. The depot of Clause 196, wherein the highly porous polymer structure at the end of the second period of time has a mass that is no greater than 50% of the mass of the depot prior to in vivo placement.

198. The depot of Clause 197, wherein the highly porous polymer structure is configured to degrade in vivo via surface erosion.

199. A method for treating postoperative pain following a non-orthopedic surgical procedure, comprising:
positioning a depot at a treatment site in vivo having physiologic fluids, the depot comprising (a) a control region including a bioresorbable polymer and a releasing agent mixed with the polymer, and (b) a therapeutic region including at least 50% by weight of an analgesic;
dissolving the releasing agent in response to contact between the releasing agent and the physiologic fluids, thereby forming diffusion openings in the control region; and
releasing analgesic through the diffusion openings from the therapeutic region to the treatment site for no less than five days.

200. The method of Clause 199, wherein the surgical procedure comprises at least one of: a thoracotomy, an esophageal surgery, a cardiac surgery, a lung resection, or a thoracic surgery.

201. The method of Clause 200, wherein the treatment site comprises a thoracic paravertebral space.

202. The method of Clause 200 or Clause 201, wherein the analgesic released from the depot at least partially blocks an intercostal nerve.

203. The method of Clause 199, wherein the surgical procedure comprises at least one of: a mastectomy, a breast augmentation, a breast reduction, or a breast reconstruction.

204. The method of Clause 203, wherein the treatment site comprises an infraclavicular space.

205. The method of Clause 203 or Clause 204, wherein the analgesic released from the depot at least partially blocks at least one of: an intercostal nerve, a medial pectoral nerve, or a lateral pectoral nerve.

206. The method of Clause 199, wherein the surgical procedure comprises at least one of: a myomectomy, a Caesarean section, a hysterectomy, an oophorectomy, or a pelvic floor reconstruction.

207. The method of Clause 199, wherein the surgical procedure comprises at least one of: a proctocolectomy, a pancreatectomy, an appendectomy, a hemorrhoidectomy, a cholecystectomy, a kidney transplant, a nephrectomy, a radical prostatectomy, a gastrectomy, a small bowel resection, a splenectomy, an incisional hernia repair, an inguinal hernia repair, a sigmoidectomy, a liver resection, an enterostomy, a rectum resection, a kidney stone removal, or a cystectomy.

208. The method of Clause 207, wherein the analgesic released from the depot at least partially blocks a nerve at or adjacent to a transverse abdominis plane.

209. The method of Clause 199, wherein the surgical procedure comprises at least one of: a tonsillectomy, a submucosal resection, a rhinoplasty, a sinus surgery, an inner ear surgery, a parotidectomy, or a submandibular gland surgery.

210. The method of Clause 199, wherein the surgical procedure comprises at least one of: a dentoalveolar surgery, a dental implant, an orthognathic surgery, a temporomandibular joint (TMJ) surgery, or an oral reconstruction surgery.

211. The method of Clause 199, wherein the surgical procedure comprises a tumor resection.

212. The method of Clause 199, wherein the surgical procedure comprises liposuction.

213. The method of any one of Clauses 199 to 212, further comprising dissolving the releasing agent at a first rate and degrading the polymer at a second rate, wherein the first rate is greater than the second rate.

214. The method of any one of Clauses 199 to 213, wherein the analgesic is released for no less than 10 days.

215. The method of any one of Clauses 199 to 214, wherein the analgesic is released for no less than 14 days.

216. The method of any one of Clauses 199 to 215, wherein no more than 20% of the amount of analgesic is released in the first day of the five days.

217. The method of any one of Clauses 199 to 216, further comprising securing the depot to the treatment site via an attachment means.

218. The method of Clause 217, wherein the attachment means is coupled to the depot prior to implantation.

219. The method of any one of Clauses 199 to 218, wherein the depot is a first depot and the method further comprises positioning a second depot at the treatment site.

220. The method of Clause 219, wherein the first and second depots together release at least 1400 mg of the analgesic to the treatment site over a period of no less than seven days.

221. The method of any one of Clauses 199 to 220, wherein no more than 400 mg of the therapeutic agent is released within any day of the five days.

222. A method for treating postoperative pain following a non-orthopedic surgical procedure, comprising:
    positioning a depot at a treatment site in vivo having physiologic fluids, the depot comprising (a) a control region including a bioresorbable polymer and a releasing agent mixed with the polymer, and (b) a therapeutic region including at least 50% by weight of an analgesic; and
    releasing analgesic from the depot to the treatment site for no less than five days.

223. The method of Clause 222, wherein the surgical procedure comprises at least one of: a thoracotomy, an esophageal surgery, a cardiac surgery, a lung resection, or a thoracic surgery.

224. The method of Clause 223, wherein the treatment site comprises a thoracic paravertebral space.

225. The method of Clause 223 or 224, wherein the analgesic released from the depot at least partially blocks an intercostal nerve.

226. The method of Clause 222, wherein the surgical procedure comprises at least one of: a mastectomy, a breast augmentation, a breast reduction, or a breast reconstruction.

227. The method of Clause 226, wherein the treatment site comprises an infraclavicular space.

228. The method of Clause 226 or 227, wherein the analgesic released from the depot at least partially blocks at least one of: an intercostal nerve, a medial pectoral nerve, or a lateral pectoral nerve.

229. The method of Clause 222, wherein the surgical procedure comprises at least one of: a myomectomy, a caesarean section, a hysterectomy, an oophorectomy, or a pelvic floor reconstruction.

230. The method of Clause 222, wherein the surgical procedure comprises at least one of: a proctocolectomy, a pancreatectomy, an appendectomy, a hemorrhoidectomy, a cholecystectomy, a kidney transplant, a nephrectomy, a radical prostatectomy, a gastrectomy, a small bowel resection, a splenectomy, an incisional hernia repair, an inguinal hernia repair, a sigmoidectomy, a liver resection, an enterostomy, a rectum resection, a kidney stone removal, or a cystectomy.

231. The method of Clause 230, wherein the analgesic released from the depot at least partially blocks a nerve at or adjacent to a transverse abdominis plane.

232. The method of Clause 222, wherein the surgical procedure comprises at least one of: a tonsillectomy, a submucosal resection, a rhinoplasty, a sinus surgery, an inner ear surgery, a parotidectomy, or a submandibular gland surgery.

233. The method of Clause 222, wherein the surgical procedure comprises at least one of: a dentoalveolar surgery, a dental implant, an orthognathic surgery, a temporomandibular joint (TMJ) surgery, or an oral reconstruction surgery.

234. The method of Clause 222, wherein the surgical procedure comprises a tumor resection.

235. The method of Clause 222, wherein the surgical procedure comprises liposuction.

236. A method for treating postoperative pain following a surgical procedure involving a patient's chest, the method comprising:
    positioning a depot proximate to an intercostal nerve at a treatment site having physiologic fluids, the depot comprising (a) a control region including a bioresorbable polymer and a releasing agent mixed with the polymer, and (b) a therapeutic region including at least 50% by weight of an analgesic; and
    releasing analgesic from the depot to the intercostal nerve for no less than five days.

237. The method of Clause 236, wherein the surgical procedure comprises at least one of: a thoracotomy, an esophageal surgery, a cardiac surgery, a lung resection, or a thoracic surgery.

238. The method of Clause 236 or 237, wherein the treatment site comprises a thoracic paravertebral space.

239. A method for treating postoperative pain following a surgical procedure involving a patient's breast, the method comprising:
    positioning a depot proximate to an intercostal and/or pectoral nerve at a treatment site having physiologic fluids, the depot comprising (a) a control region including a bioresorbable polymer and a releasing agent mixed with the polymer, and (b) a therapeutic region including at least 50% by weight of an analgesic; and
    releasing analgesic from the depot to the intercostal and/or pectoral nerve for no less than five days.

240. The method of Clause 239, wherein the surgical procedure comprises at least one of: a mastectomy, a breast augmentation, a breast reduction, or a breast reconstruction.

241. The method of Clause 239 or 240, wherein the treatment site comprises an intraclavicular space.

242. A method for treating postoperative pain following a general, abdominal, or urological surgical procedure, the method comprising:
    positioning a depot proximate to a transverse abdominis plane at a treatment site having physiologic fluids, the depot comprising (a) a control region including a bioresorbable polymer and a releasing agent mixed with the polymer, and (b) a therapeutic region including at least 50% by weight of an analgesic; and
    releasing analgesic from the depot to the intercostal and/or pectoral nerve for no less than five days.

243. The method of Clause 242, wherein the surgical procedure comprises at least one of: a proctocolectomy, a pancreatectomy, an appendectomy, a hemorrhoidectomy, a cholecystectomy, a kidney transplant, a nephrectomy, a radical prostatectomy, a gastrectomy, a small bowel resection, a splenectomy, an incisional hernia repair, an inguinal hernia repair, a sigmoidectomy, a liver resection, an enterostomy, a rectum resection, a kidney stone removal, or a cystectomy.

244. A depot for sustained, controlled release of a therapeutic agent, the depot comprising:
    a therapeutic region comprising the therapeutic agent; and
    a control region comprising a bioresorbable polymer and a releasing agent mixed with the polymer, wherein the releasing agent is configured to dissolve when the depot is placed in vivo to form diffusion openings in the control region;

wherein the depot is configured such that, following submersion of the depot in buffer solution for seven days, the flexural strength of the depot decreases by no more than 75%.

245. The depot of Clause 244, wherein the depot is configured such that, following submersion of the depot in buffer solution for seven days, the flexural strength of the depot decreases by no more than 70%.

246. The depot of Clause 244, wherein the depot is configured such that, following submersion of the depot in buffer solution for seven days, the flexural strength of the depot decreases by no more than 65%.

247. The depot of Clause 244, wherein the depot is configured such that, following submersion of the depot in buffer solution for seven days, the flexural strength of the depot decreases by no more than 60%.

248. The depot of Clause 244, wherein the depot is configured such that, following submersion of the depot in buffer solution for seven days, the flexural strength of the depot decreases by no more than 55%.

249. The depot of Clause 244, wherein the depot is configured such that, following submersion of the depot in buffer solution for seven days, the flexural strength of the depot decreases by no more than 50%.

250. The depot of Clause 244, wherein the depot is configured such that, following submersion of the depot in buffer solution for seven days, the flexural strength of the depot decreases by no more than 45%.

251. A depot for sustained, controlled release of a therapeutic agent, the depot comprising:
a therapeutic region comprising the therapeutic agent; and
a control region comprising a bioresorbable polymer and a releasing agent mixed with the polymer, wherein the releasing agent is configured to dissolve when the depot is placed in vivo to form diffusion openings in the control region;
wherein the depot is configured such that, following submersion of the depot in buffer solution until approximately 75% of the therapeutic agent by weight has been released, the flexural strength of the depot decreases by no more than 75%.

252. The depot of Clause 251, wherein the depot is configured such that, following submersion of the depot in buffer solution until approximately 75% of the therapeutic agent by weight has been released, the flexural strength of the depot decreases by no more than 70%.

253. The depot of Clause 251, wherein the depot is configured such that, following submersion of the depot in buffer solution until approximately 75% of the therapeutic agent by weight has been released, the flexural strength of the depot decreases by no more than 65%.

254. The depot of Clause 251, wherein the depot is configured such that, following submersion of the depot in buffer solution until approximately 75% of the therapeutic agent by weight has been released, the flexural strength of the depot decreases by no more than 60%.

255. The depot of Clause 251, wherein the depot is configured such that, following submersion of the depot in buffer solution until approximately 75% of the therapeutic agent by weight has been released, the flexural strength of the depot decreases by no more than 55%.

256. The depot of Clause 251, wherein the depot is configured such that, following submersion of the depot in buffer solution until approximately 75% of the therapeutic agent by weight has been released, the flexural strength of the depot decreases by no more than 50%.

257. The depot of Clause 251, wherein the depot is configured such that, following submersion of the depot in buffer solution until approximately 75% of the therapeutic agent by weight has been released, the flexural strength of the depot decreases by no more than 45%.

258. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 14 days, and
wherein about 20% to about 40% of the analgesic is released in the first 3 days of the 14 days, and wherein at least 80% of the remaining analgesic is released in the last 11 days of the 14 days.

259. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 3 days, and
wherein the control region does not include the analgesic at least prior to implantation of the depot at the treatment site.

260. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region; and
wherein the depot is configured to be implanted at a treatment site in vivo and, while implanted, release the analgesic at the treatment site for no less than 3 days,
wherein the control region comprises an analgesic different from the analgesic in the therapeutic region.

261. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 3 days, and
wherein the releasing agent is a first releasing agent and the therapeutic region includes a second releasing agent mixed with the analgesic.

262. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 3 days, and
wherein the releasing agent is a first releasing agent and the polymer is a first polymer, and the therapeutic region includes a second releasing agent and a second polymer mixed with the analgesic.

263. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 3 days, and
wherein a thickness of the control region is less than or equal to 1/50 of a thickness of the therapeutic region.

264. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 3 days, and
wherein a thickness of the control region is less than or equal to 1/75 of a thickness of the therapeutic region.

265. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 3 days, and
wherein a thickness of the control region is less than or equal to 1/100 of a thickness of the therapeutic region.

266. A depot for the treatment of postoperative pain via sustained, controlled release of an analgesic, comprising:
a therapeutic region comprising the analgesic; and
a control region comprising a bioresorbable polymer and a releasing agent mixed with the polymer, wherein the releasing agent is configured to dissolve when the depot is placed in vivo to form diffusion openings in the control region,
wherein the depot is configured to be implanted at a treatment site in vivo and, while implanted, release the analgesic at the treatment site for no less than 3 days, and
wherein the first control layer includes a first amount of the releasing agent and the second control layer includes a second amount of the releasing agent different than the first amount.

267. A depot for the treatment of postoperative pain via sustained, controlled release of an analgesic, comprising:
a therapeutic region comprising the analgesic;
a control region comprising a bioresorbable polymer and a releasing agent mixed with the polymer, wherein the releasing agent is configured to dissolve when the depot is placed in vivo to form diffusion openings in the control region;
wherein the depot is configured to be implanted at a treatment site in vivo and, while implanted, release the analgesic at the treatment site for no less than 3 days,
wherein the depot has a total surface area comprising the exposed surface area of the cover region plus the exposed surface area of the therapeutic region, and
wherein, when the depot is initially positioned at the treatment site in vivo, a ratio of the exposed surface area of the therapeutic region to the exposed surface area of the cover region is from about 5% to about 20%, or from about 5% to about 15%, or from about 5% to about 10%.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 9A is an isometric view of a depot in accordance with some embodiments of the present technology.

FIG. 9B is a cross-sectional view of the depot shown in FIG. 9A.

FIG. 10 is a cross-sectional view of a depot in accordance with some embodiments of the present technology.

FIG. 11 is a cross-sectional view of a depot in accordance with some embodiments of the present technology.

FIGS. 28A-28C illustrate a table showing common surgical procedures for which the depots of the present technology may be utilized for treating postoperative pain. FIGS. 28A-28C also show nerve targets and anatomical access/placement associated with the different surgeries.

FIGS. 29A-29C are anterior, lateral, and medial views of a human knee, showing the location of the nerves innervating the knee.

DETAILED DESCRIPTION

The present technology relates to implantable depots for the sustained, controlled release of therapeutic agents, and associated devices, systems, and methods of use. An overview of the depots of the present technology and associated release kinetics are described below with reference to FIGS. 2 and 3 and Section I. Selected embodiments of the depots of the present technology are described below with reference to FIGS. 4-19C and Section II. Selected examples of the depots of the present technology and associated release profiles are described below with reference to FIGS. 20-26C and Section III. Selected devices, systems, and methods for using the depots of the present technology for treating postoperative pain associated with orthopedic surgery are described below with reference to FIGS. 27A-32 and Section IV. Selected devices, systems, and methods for using the depots of the present technology for treating postoperative pain associated with other surgeries are described below at Section V.

I. OVERVIEW

Disclosed herein are implantable depots and associated devices, systems, and methods for treating (i.e., preventing, reducing, and/or eliminating) postoperative pain via sustained, controlled release of a therapeutic agent while the depot is implanted at a treatment site in vivo. Many embodiments of the present technology comprise one or more depots configured to be implanted at or near a surgical site of a patient to treat pain following a surgery. While implanted in vivo, the depot(s) are configured to release a therapeutic agent (such as an analgesic) to the surgical site in a controlled, prescribed manner for at least 3 days following implantation.

As used herein, a "depot" comprises the composition in which at least one therapeutic agent is administered to the body of a patient. Thus, a depot may comprise a physical structure or carrier to facilitate implantation and retention in a desired site (e.g., tissue at the intracapsular and/or extracapsular space of a knee joint). The depot also comprises the therapeutic agent itself. A "depot" includes but is not limited to films, sheets, strips, ribbons, capsules, coatings, matrices, wafers, pills, pellets, or other pharmaceutical delivery apparatus or a combination thereof. Moreover, as used herein, "depot" may refer to a single depot, or may refer to multiple depots. As an example, the statement "The depot may be configured to release 2 g of therapeutic agent to a treatment site" describes (a) a single depot that is configured to release 2 g of therapeutic agent to a treatment site, and (b) a plurality of depots that collectively are configured to release 2 g of therapeutic agent to a treatment site.

Figure 1:
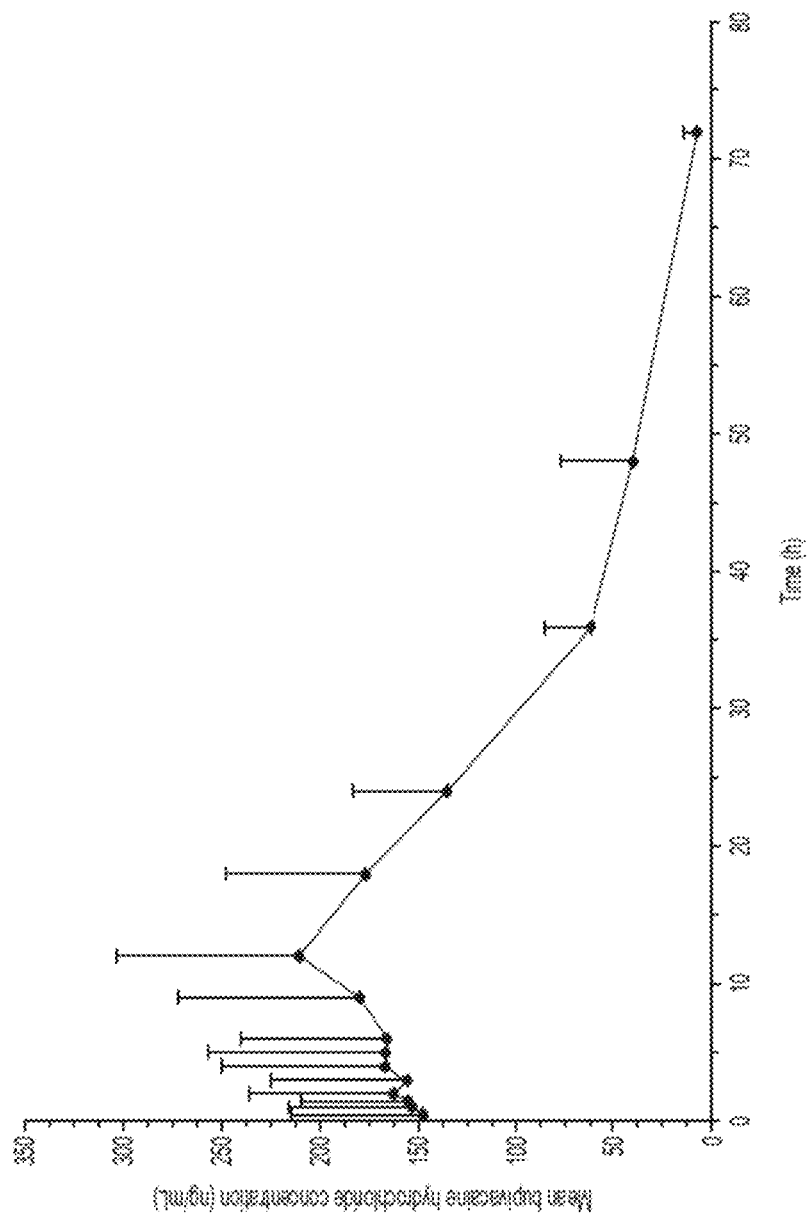
FIG. 1 depicts the release of bupivacaine hydrochloride over time from a Xaracoll® sponge.
Figure 2:
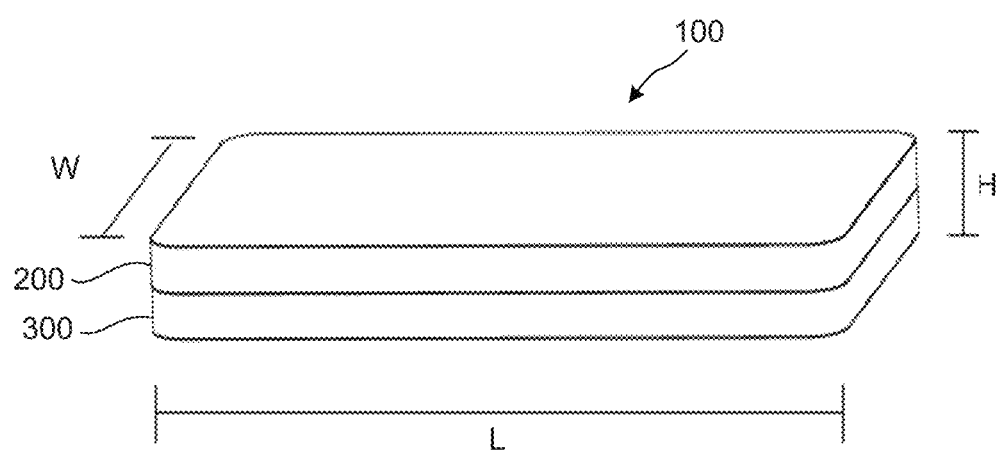
FIG. 2 is an isometric view of a depot configured in accordance with the present technology.

FIG. 2 is an isometric view of an implantable depot 100 in accordance with several embodiments of the present technology. The depot 100 may be a thin, multi-layered polymer film configured to be implanted at a treatment site comprising a therapeutic region 200 containing a therapeutic agent (such as an analgesic), and a control region 300 configured to regulate the release of the therapeutic agent from the depot 100 in a controlled and sustained manner. The depot 100 may include a high therapeutic payload of the therapeutic agent, especially as compared to other known films of equal thickness or polymer weight percentage. For example, in some embodiments, the depot 100 comprises at least 50% by weight of the therapeutic agent.

The control region 300 may comprise a bioresorbable polymer and a releasing agent mixed with the polymer, and the therapeutic region 200 may comprise a bioresorbable polymer and a releasing agent mixed with the polymer and the therapeutic agent. The control region 300 may optionally include a therapeutic agent, or the control region may include no therapeutic agent at all. As detailed in Section II below, in some embodiments the therapeutic region 200 and/or the control region 300 may have different constituents and/or formulations.

When a fluid contacts the depot 100, the releasing agent dissolves within the surrounding polymer of the control region 300 and/or therapeutic region 200 faster than the polymer degrades. As the releasing agent dissolves, the space vacated by the dissolved releasing agent forms diffusion openings (e.g., channels, voids, pores, etc.) in the surrounding polymer region. The concentration and type of releasing agent, among other parameters, can be selected to regulate the release of the therapeutic agent from the therapeutic region 200 and through the control region 300 into the surrounding fluid at a controlled dosage rate over a desired period of time.

As shown in FIG. 2, at least a portion of the control region 300 may be disposed on or adjacent the therapeutic region 200 such that, when the depot 100 is initially positioned in vivo, the control region 300 is between at least a portion of the therapeutic region 200 and physiologic fluids at the treatment site. For example, the control region 300 can cover all or a portion of one or more sides or edges of the therapeutic region 200. When the depot 100 is exposed to physiologic fluids, the therapeutic agent elutes from the exposed surfaces of the therapeutic region 200 and through the control region 300 by way of the diffusion openings created by dissolution of the releasing agent. In general, the therapeutic agent elutes from the exposed surfaces of the therapeutic region 200 at a faster (e.g., greater) rate than through the control region 300. As a result, the control region 300 prolongs the release of the therapeutic agent from the therapeutic region 200 to provide for longer release times and regulates the dosage rate to provide the desired degree of pain relief and avoid complications related to overdosing.

The depot of the present technology is configured to release a therapeutic agent in a highly controlled, predetermined manner that is specifically tailored to the medical condition being treated and the therapeutic agent used. As described in greater detail below in Section II, the release kinetics of the depots may be customized for a particular application by varying one or more aspects of the depot's composition and/or structure, such as the shape and size of the depot; the exposed surface area of the therapeutic region 200; the type of polymer (in the therapeutic region 200 and/or in the control region 300); the weight percentage of the therapeutic agent, the polymer, and/or the releasing agent (within a particular region or generally throughout the depot 100); and the composition of the therapeutic region 200 and the control region 300.

Figure 3:
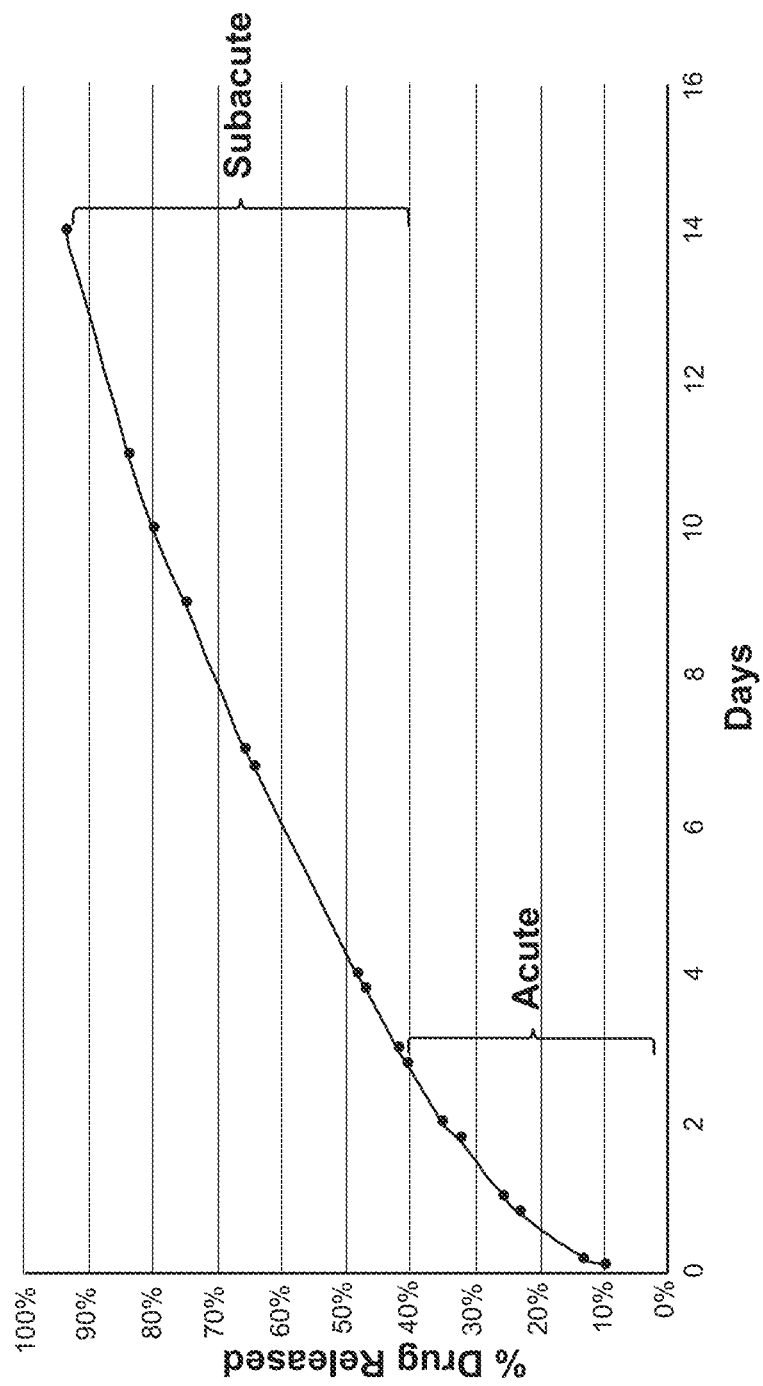
FIG. 3 depicts the release profile over time of one or more depots of the present technology.

As shown in FIG. 3, in many embodiments the depot 100 (or a system of depots 100) is configured to release a disproportionately larger volume of a therapeutic agent per day for a first period of time than for a longer second period of time. In some embodiments, the depot 100 (or a system of depots 100) is configured to release the therapeutic agent for at least 14 days post-implantation (or post-immersion in a fluid), where a controlled burst of about 20% to about 50% of the therapeutic agent payload is released in the first 3-5 days, and at least 80% of the remaining therapeutic agent payload is released at a slower rate over the last 10-11 days. In some embodiments, at least 90% of the therapeutic agent payload is released by the end of 14 days.

A two-stage, second-order release profile-such as that shown in FIG. 3—may be especially beneficial in the context of treating pain resulting from a total knee arthroplasty ("TKA"). TKA patients typically experience the greatest pain within the first 1-3 days following surgery (clinically referred to as "acute pain") with increasingly less pain over the next 7-10 days (clinically referred to as "subacute pain"). The acute period often overlaps or coincides with the patient's inpatient care (usually 1-3 days), and the subacute period generally begins when the patient is discharged and returns home. The two-stage, second-order release profile shown in FIG. 3 is also beneficial for other surgical applications, such as other orthopedic applications (e.g., ligament repair/replacement and other damage to the knee, shoulder, ankle, etc.) or non-orthopedic surgical applications. Excessive pain following any surgery may extend inpatient care, cause psychological distress, increase opioid consumption, and/or impair patient participation in physical therapy, any of which may prolong the patient's recovery and/or mitigate the extent of recovery. Pain relief during the subacute period may be particularly complicated to manage, as patient compliance with the prescribed pain management regimen drops off when patients transition from an inpatient to home environment.

To address the foregoing challenges in post-surgical pain management, the depot 100 (or depot system comprising multiple depots 100) of the present technology may have a release profile tailored to meet the pain management needs specific to the acute and subacute periods. For example, to address the greater acute pain that occurs immediately following surgery, the depot 100 may be configured to release the therapeutic agent at a faster rate for the first 3-5 days after implantation (as shown in FIG. 3) compared to a subsequent period of 9-11 days. In some embodiments, the depot 100 may deliver a local anesthetic at a rate of from about 150 mg/day to about 400 mg/day during this first, acute period. To address the diminishing pain during the subacute period, the depot 100 may be configured to release the therapeutic agent at a slower rate for the remaining 9-11 days. In some embodiments, the depot 100 may deliver a local anesthetic at a rate of from about 50 mg/day to about 250 mg/day during this second, subacute period. In some embodiments, the rate of release continuously decreases throughout the first period and/or the second period.

The release profile of the depot 100 may be tuned to release a therapeutic agent for other durations and/or at other release rates by adjusting the structure, composition, and the process by which the depot is manufactured. For example, in some embodiments the depot 100 may be configured to release the therapeutic agent at a constant rate throughout the entire duration of release. In particular embodiments, the depot 100 may be configured to release the therapeutic agent at a constant rate for a first period of time and at a non-constant rate for a second period of time (which may occur before or after the first period of time).

In some embodiments, the depot 100 is configured to release no more than 20%, no more than 25%, no more than 30%, no more than 35%, no more than 40%, no more than 45%, no more than 50%, no more than 55%, no more than 60%, no more than 65%, or no more than 70% of the therapeutic agent in the first day, 2 days, 3 days, 4 days, 5 days, 6 days, 8 days, 9 days, 10 days, 11 days, 12 days, or 13 days of the duration of release, and wherein at least 75%, at least 80%, at least 85%, at least 90%, at least 95%, or 100% of the remaining therapeutic agent is released in the remaining days of the duration of release. The intended duration of release may be at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days.

In some embodiments, the depot 100 is configured to release at least 70%, at least 75%, at least 80%, at least 85%, at least 90%, at least 95%, at least 96%, at least 97%, at least 98%, at least 99%, or 100% of the therapeutic agent in the depot 100 within the intended duration of treatment. The intended duration of treatment may be at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 40 days, at least 50 days, at least 60 days, at least 70 days, at least 90 days, at least 100 days, at least 200 days, at least 300 days, or at least 365 days.

In some embodiments, the depot 100 is configured to release from about 50 mg/day to about 600 mg/day, 100 mg/day to about 500 mg/day, or from about 100 mg/day to about 400 mg/day, or from about 100 mg/day to about 300 mg/day of the therapeutic agent to the treatment site. In general, the release rate can be selected to deliver the desired dosage to provide the extent of pain relief needed at a given time after the surgical procedure, control toxicity, and deliver the therapeutic agent for a sufficient period of time for pain relief.

In some embodiments, the depot 100 is configured to release from about 50 mg/day to about 600 mg/day, from about 100 mg/day to about 500 mg/day, or from about 100 mg/day to about 400 mg/day, or from about 100 mg/day to about 300 mg/day of the therapeutic agent to the treatment site within a first period of release. The depot 100 can further be configured to release from about 500 mg/day to about 600 mg/day, about 100 mg/day to about 500 mg/day, or from about 100 mg/day to about 400 mg/day, or from about 100 mg/day to about 300 mg/day of the therapeutic agent to the treatment site within a second period of release. The release rate during the first period may be the same as, different than, less than, or greater than the release rate during the second period. Moreover, the first period may be longer or shorter than the second period. The first period may occur before or after the second period.

In some embodiments, the depot 100 is configured to release no more than 50 mg, no more than 100 mg, no more than 150 mg, no more than 200 mg, no more than 250 mg, no more than 300 mg, no more than 350 mg, no more than 400 mg, no more than 450 mg, no more than 500 mg, no more than 600 mg, no more than 700 mg, no more than 800 mg, no more than 900 mg, or no more than 1000 mg of the therapeutic agent within any day of a first period of release. This may be useful for providing different degrees of pain relief at different times after the surgical procedure, and it may also be useful to control toxicity. In such embodiments, the depot 100 may be configured to release no more than 50 mg, no more than 100 mg, no more than 150 mg, no more than 200 mg, no more than 250 mg, no more than 300 mg, no more than 350 mg, no more than 400 mg, no more than 450 mg, no more than 500 mg, no more than 600 mg, no more than 700 mg, no more than 800 mg, no more than 900 mg, or no more than 1000 mg of the therapeutic agent within any day of a second period of release. The first period of release and/or the second period of release may be 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. The depot 100 may be configured to release the therapeutic agent at a first rate during the first period and at a second rate during the second period. The first rate may be the same as, different than, less than, or greater than the second rate. Moreover, the first period may be longer or shorter than the second period. The first period may come before or after the second period.

In some embodiments, the depot 100 is configured to release no more than 50 mg, no more than 100 mg, no more than 150 mg, no more than 200 mg, no more than 250 mg, no more than 300 mg, no more than 350 mg, no more than 400 mg, no more than 450 mg, no more than 500 mg, no more than 600 mg, no more than 700 mg, no more than 800 mg, no more than 900 mg, or no more than 1000 mg of therapeutic agent within any day of the duration of release.

In some embodiments, the depot 100 is configured to release the therapeutic agent at a treatment site in vivo and/or in the presence of one or more fluids for no less than 1 day, no less than 2 days, no less than 3 days, no less than 4 days, no less than 5 days, no less than 6 days, no less than 7 days, no less than 8 days, no less than 9 days, no less than 10 days, no less than 11 days, no less than 12 days, no less than 13 days, no less than 14 days, no less than 15 days, no less than 16 days, no less than 17 days, no less than 18 days, no less than 19 days, no less than 20 days, no less than 21 days, no less than 22 days, no less than 23 days, no less than 24 days, no less than 25 days, no less than 26 days, no less than 27 days, no less than 28 days, no less than 29 days, no less than 30 days, no less than 40 days, no less than 50 days, no less than 60 days, no less than 70 days, no less than 90 days, no less than 100 days, no less than 200 days, no less than 300 days, or no less than 365 days.

II. SELECTED DEPOT EMBODIMENTS

The release kinetics of the depots of the present technology may be tuned for a particular application by varying one or more aspects of the depot's structure, such as the exposed surface area of the therapeutic region 200, the porosity of the control region 300 during and after the releasing agent dissolves, the concentration of the therapeutic agent in the therapeutic region, the post-manufacturing properties of the polymer, the structural integrity of the depots to avoid a sudden release of the therapeutic agent, the relative thicknesses of the therapeutic region 200 compared to the control region 300, and other properties of the depots. Several embodiments of depots of the present technology combine one or more of these properties in a manner that produces exceptional two-phase release profiles in animal studies that significantly outperform existing injectable or implantable systems, while also overcoming the shortcomings of disclosed prophetic devices. For example, several embodiments have exhibited two-phase release profiles that deliver an adequate mass of therapeutic agent to treat pain associated with joint replacement surgery or other applications over a 14-day period while maintaining sufficient structural integrity to withstand the forces of a joint to avoid a sudden release of too much therapeutic agent. This surprising result enables depots of the present technology to at least reduce, if not replace, opioids and/or enhance other existing pain relief systems for orthopedic surgical applications, non-orthopedic surgical applications, and for other applications (e.g., oncological).

For example, the release profile can be tuned by, at least in part, controlling the amount of exposed surface area of the therapeutic region 200 because depots having a therapeutic region 200 covered only partially by a control region 300 (see, for example, FIGS. 2, 4-8, and 13) will generally release a higher proportion of the total payload over a shorter period of time as compared to embodiments where the therapeutic region 200 is completely encapsulated by the control region 300 (see, for example, FIGS. 9A-12). More specifically, depot designs having a therapeutic region 200 with exposed edges will typically release the therapeutic agent at a high, substantially linear rate for a first period of time and then at a lower, substantially linear rate for a second period of time. Alternatively, depot designs having a therapeutic region 200 with edges that are substantially covered by one or more control regions 300 may achieve a zero-order release such that the release of the payload of therapeutic agent is at substantially the same rate.

Figure 4:
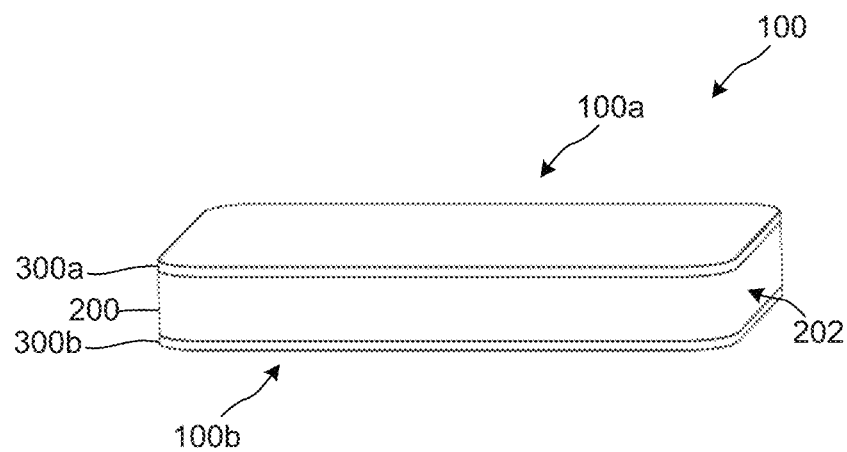
FIG. 4 is an isometric view of a depot in accordance with some embodiments of the present technology.

As shown in FIG. 4, in some embodiments the depot 100 may comprise a multi-layer polymer film having a therapeutic region 200 and first and second control regions 300a, 300b positioned at opposite sides 100a, 100b of the therapeutic region 200. The depot 100 may be in the form of a flexible, rectangular strip having a length L, a width W, and a height H (or thickness). In some embodiments, the depot 100 has a length L of from about 20 mm to about 30 mm (e.g., about 25 mm, etc.), a width W of from about 10 mm to about 20 mm (e.g., about 15 mm, etc.), and a height H of from about 0.4 mm to about 4 mm (e.g., of from about 1 mm to about 3 mm, of from about 1 mm to about 2 mm, at least 0.4 mm, at least 0.5 mm, at least 0.6 mm, at least 0.7 mm, at least 0.8 mm, at least 0.9 mm, at least 1 mm, at least 1.2 mm, at least 1.4 mm, at least 1.5 mm, at least 1.6 mm, at least 1.7 mm, at least 1.8 mm, at least 2 mm, at least about 3 mm, etc.). In some embodiments, the depot 100 may have other shapes and/or dimensions, such as those detailed below.

The control regions 300a, 300b may only cover a portion of the therapeutic region 200 such that a portion of each of the sides (e.g., sidewall) of the therapeutic region 200 is exposed to physiologic fluids immediately upon implantation of the depot 100 in vivo. When the depot 100 is exposed to physiologic fluids (or any similar fluid in an in vitro setting), the therapeutic agent will elute from the exposed surfaces 202 (in addition to through the control regions 300a, 300b), such that the therapeutic agent is released faster than if the therapeutic region 200 had no exposed regions. As such, the surface area of the exposed surfaces 202 may be tailored to provide an initial, controlled burst, followed by a tapering release (for example, similar to that shown at FIG. 3). The initial, more aggressive release of the therapeutic agent is slowed in part by the control regions 300a, 300b that initially reduce the surface area of the therapeutic region 200 exposed to the fluids. Unlike the depots 100 of the present technology, many conventional drug-eluting technologies provide an initial, uncontrolled burst release of drug when exposed to physiologic fluids. Several embodiments of depots of the present technology not only enable enough therapeutic agent to be implanted for several days' or weeks' worth of dosage to achieve a sustained, durable, in vivo pharmacological treatment, but they also release the therapeutic agent as prescribed and thereby prevent a substantial portion of the entire payload being released in an uncontrolled manner that could potentially result in complications to the patient and/or reduce the remaining payload such that there is not enough therapeutic agent remaining in the depot to deliver a therapeutic amount for the remaining duration of release.

In some embodiments, the depot 100 shown in FIG. 4 is configured such that about 20% to about 50% of the analgesic is released in the first about 3 days to about 5 days of the 14 days, and wherein at least 80% of the remaining analgesic is released in the last about 9 days to about 11 days of the 14 days. This release profile provides higher dosages of the therapeutic agent during the acute period after surgery compared to the subacute period. In some embodiments, the depot 100 shown in FIG. 4 is configured to release about 100 mg to about 500 mg of analgesic to the treatment site per day, and in some cases no more than 400 mg or no more than 300 mg of analgesic per day within the first 3 days of implantation and no more than 200 mg per day in the remaining days. Additionally, some embodiments of the depot shown in FIG. 4 are configured such that a thickness of the control regions 300a and 300b, either individually or collectively, is less than or equal to $\frac{1}{50}$ of a thickness of the therapeutic region 200. The thickness of the control regions 300a and 300b, either individually or collectively, can further be no more than $\frac{1}{75}$ or $\frac{1}{100}$ of the thickness of the therapeutic region 200. Further, the depot 100 shown FIG. 4 can have a ratio of the mass of the analgesic in the depot to the depot polymer mass is at least 16:1, 10:1, 8:1, 7:1, 6:1, 5:1, 4:1, 3:1, or 2:1.

Several embodiments of the depot 100 shown in FIG. 4 are also configured to maintain their structural integrity even after a substantial portion of the releasing agent has eluted from the depot 100. As the releasing agent(s) dissolves and therapeutic agent(s) elutes, the functional mechanical aspects of the depot 100 may change over time. Such mechanical aspects include structural integrity, flexural strength, tensile strength, or other mechanical characteristics of the depot. If a depot 100 experiences too much degradation too fast, it may fail mechanically and release an undesirable burst of therapeutic agent into the body. Several embodiments of depots 100 shown in FIG. 4 are loaded with enough therapeutic agent to deliver 100 mg to 500 mg of the therapeutic agent per day while still being able to maintain its structural integrity such that depot remains largely intact up to at least 14 days after implantation. For example, the therapeutic agent can be at least 50%-95% by weight of the total weight of the depot 100 before implantation, or 55%-85% by weight of the total weight of the depot 100 before implantation, or 60%-75% by weight of the total weight of the depot 100 before implantation. A depot can be sufficiently intact, for example, if it does not fracture into multiple component pieces with two or more of the resulting pieces being at least 5% of the previous size of the depot. Alternatively, or additionally, a depot can be considered to be sufficiently intact if the release rate of the therapeutic agent does not increase by more than a factor of three as compared to the release rate of therapeutic agent in a control depot submerged in a buffered solution.

Several embodiments of the depot 100 shown in FIG. 4 having one or more combinations of the parameters described in the preceding paragraphs have provided exceptional results in animal studies as described herein. For example, a depot 100 was configured such that (a) the thickness of the control regions 300a-b were each or collectively less than or equal to 1/50 of the thickness of the therapeutic region 200, (b) the mass of therapeutic agent payload was sufficient to release about 100 mg to about 500 mg of analgesic to the treatment site per day, and (c) the structural integrity was such that the depot remained largely intact for at least 14 days after implantation. These embodiments were able to release about 20% to about 50% of the analgesic payload in the first about 3 days to about 5 days of the 14 days, and then release at least 80% of the remaining analgesic payload in the last about 9 days to about 11 days of the 14 days. This was unexpected because, at least in part, (a) providing such a large payload of therapeutic agent in the therapeutic region was expected to cause the depot 100 fail mechanically on or before 14 days post-implant, and (b) no disclosed devices had achieved a release profile wherein about 20% to about 50% of the analgesic was released in the first about 3 days to about 5 days of the 14 days, and then at least 80% of the remaining analgesic was released in the last about 9 days to about 11 days of the 14 days.

Figure 5:
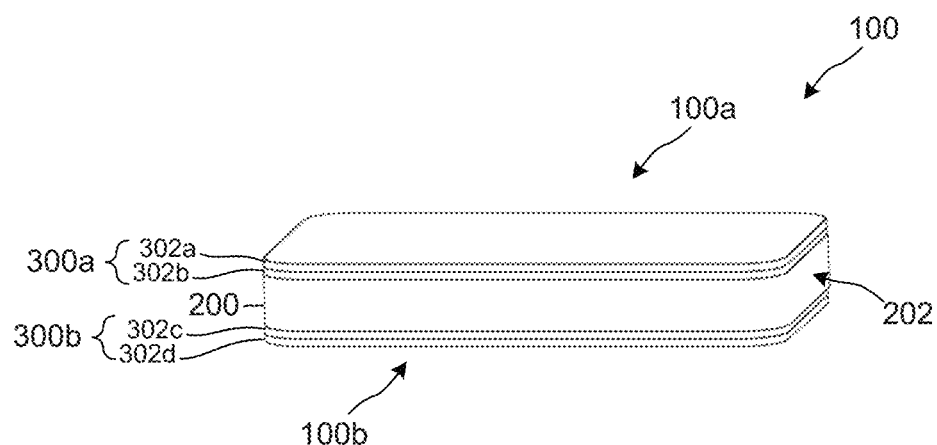
FIG. 5 is an isometric view of a depot in accordance with some embodiments of the present technology.

In some embodiments, one or more control regions 300 of the depot 100 may comprise two or more sub-control regions. For example, as shown in FIG. 5, the depot 100 may have a first control region 300a and a second control region 300b, each of which comprises first and second sub-control regions 302a, 302b and 302c, 302d, respectively. The first and second control regions 300a, 300b and/or one, some or all of the sub-control regions 302a-302d may have the same or different amounts of releasing agent, the same or different concentrations of releasing agent, the same or different releasing agents, the same or different amounts of polymer, the same or different polymers, the same or different polymer to releasing agent ratios, and/or the same or different thicknesses. In some embodiments, the concentration of the releasing agent in the individual outer control sub-regions 302a, 302d is less than the concentration of the releasing agent in the individual inner control sub-regions 302b, 302c such that the outer portion of the collective control region will elute the therapeutic agent more slowly than the inner portion of the collective control region. In some embodiments, the concentration of the releasing agent in the individual outer control sub-regions 302a, 302d is greater than the concentration of the releasing agent in the individual inner control sub-regions 302b, 302c. In those embodiments where the control region includes more than two sub-regions, the concentration of releasing agent per sub-region or layer may increase, decrease, or remain constant as the sub-control regions are farther away from the therapeutic region 200.

In certain embodiments, the outer control sub-regions include at least 5% by weight of the releasing agent, at least 10% by weight of the releasing agent, at least 15% by weight of the releasing agent, at least 20% by weight of the releasing agent, at least 25% by weight of the releasing agent, at least 30% by weight of the releasing agent, at least 35% by weight of the releasing agent, at least 40% by weight of the releasing agent, at least 45% by weight of the releasing agent, or at least 50% by weight of the releasing agent. In some embodiments, the inner control sub-regions include at least 5% by weight of the releasing agent, at least 10% by weight of the releasing agent, at least 15% by weight of the releasing agent, at least 20% by weight of the releasing agent, at least 25% by weight of the releasing agent, at least 30% by weight of the releasing agent, at least 35% by weight of the releasing agent, at least 40% by weight of the releasing agent, at least 45% by weight of the releasing agent, or at least 50% by weight of the releasing agent. In some embodiments, the outer control sub-regions may include a first amount of the releasing agent and the inner control sub-regions may include a second amount of the releasing agent, where the second amount is at least 200%, at least 300%, at least 400%, or at least 500% greater than the first amount.

Figure 6:
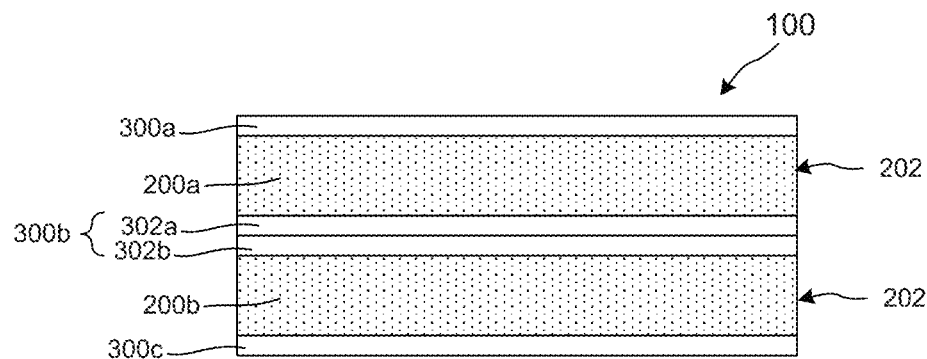
FIG. 6 is a cross-sectional view of a depot in accordance with some embodiments of the present technology.
Figure 7:
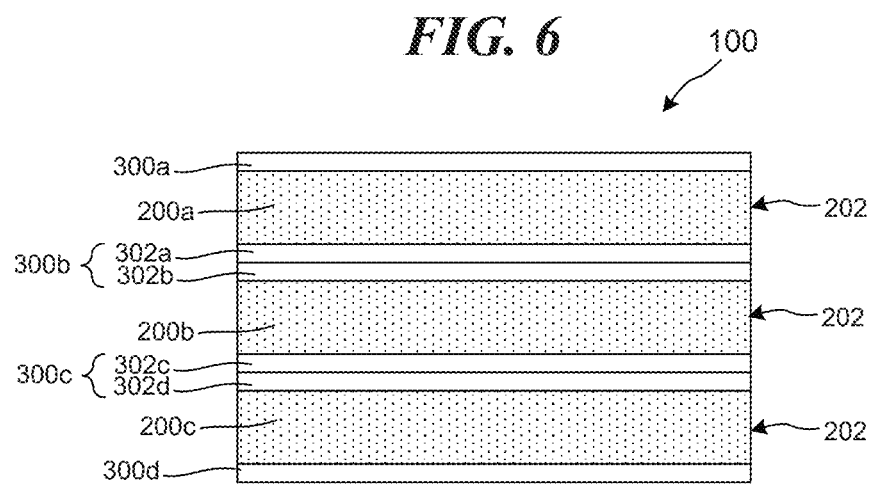
FIG. 7 is a cross-sectional view of a depot in accordance with some embodiments of the present technology.
Figure 8:
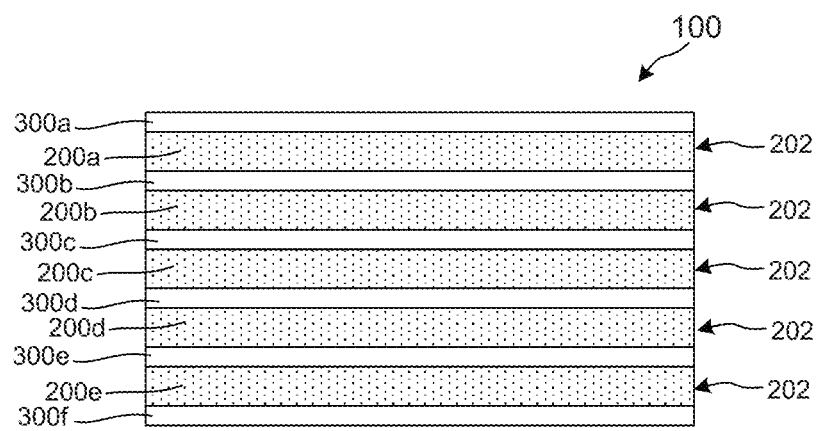
FIG. 8 is a cross-sectional view of a depot in accordance with some embodiments of the present technology.

FIGS. 6-8 show depot embodiments having a plurality of alternating therapeutic regions 200 and control regions 300 in accordance with the present technology. The depot 100 may have two or more control regions 300 and/or sub-regions 302 (e.g., 2, 3, 4, 5, 6, 7, 8, 9, 10, 20, etc.), and the depot 100 may have one or more therapeutic regions 200 and/or sub-regions 202 (e.g., 1, 2, 3, 4, 5, 6, 7, 10, 15, 20, etc.) surrounded by at least one control region 300 and/or sub-region 302. In some embodiments, each of the therapeutic regions 200 may comprise a single layer and/or each of the control regions 300 may comprise a single layer. In some embodiments, one, some, or all of the therapeutic regions 200 may comprise multiple layers and/or one, some, or all of the control regions 300 may comprise multiple layers. In some embodiments, for example as shown in FIGS. 6 and 7, two or more sub-regions 302a-b (FIG. 6) and 302a-b and 302c-d (FIG. 7) may be adjacent to each other between sub-regions 202 of the therapeutic region 200. Moreover, one or more of the individual control regions 300 and/or one or more of the therapeutic regions 200 may have the same or different amounts and/or types of releasing agent, and one or more of the therapeutic regions may have the same or different amounts and/or types of therapeutic agent.

The embodiments shown in FIGS. 6-8 may be beneficial where the therapeutic region comprises a large payload of the therapeutic agent (e.g., equivalent to many days, weeks or months of dosage). These embodiments may be beneficial because, with such a large payload, should the therapeutic region 200 be exposed to the body abruptly, the entire payload may be released prematurely, subjecting the patient to an abnormally and undesirably high dose of the therapeutic agent. For example, if the integrity of the control region 300 were compromised, the patient may be exposed in vivo to the therapeutic agent at a higher rate than intended, potentially resulting in a clinical complication. Particularly with respect to the administration of local anesthetics (e.g., bupivacaine, ropivacaine, etc.), manufacturing guidelines recommend no more than 400 mg should be administered within a 24-hour period. However, multiple studies have demonstrated that doses higher than 400 mg from extended release products are safe due to their slower release over an extended period of time. Regardless, in the event that a control region 300 is compromised, it is desirable for the patient to be subjected only to a fraction of the total payload, whereby the fraction to which the patient is exposed if prematurely released would be within safety margins for the particular therapeutic agent. The structural integrity of the control regions 300, as well as that of the therapeutic region(s) 200, is an important property for depots with large masses of therapeutic agents that are to be delivered over a long period of time.

To address this concern, in some embodiments of the present technology, the depot 100 may comprise multiple therapeutic regions 200 separated by one or more control regions 300 (for example, as shown in FIGS. 6-8). Such a configuration allows the therapeutic agent in each therapeutic region 200 (which carries a fraction of the total payload), to be individually sequestered. In the event a particular control region is compromised, only the fractional payload corresponding to the therapeutic region associated with the compromised control region would prematurely release. For example, in some of the foregoing embodiments, the total payload of the depot 100 may be at least 100 mg, at least 150 mg, at least 200 mg, at least 300 mg, at least 400 mg, at least 500 mg, at least 600 mg, at least 700 mg, at least 800 mg, at least 900 mg, or at least 1000 mg of therapeutic agent, such as an analgesic (e.g., bupivacaine, ropivacaine, etc.). Likewise, in some embodiments the fractional payload of each therapeutic region or sub-region may be up to 1%, up to 5%, up to 10%, up to 15%, up to 20%, up to 25%, up to 30%, up to 40%, up to 50%, up to 60%, up to 70%, up to 80%, up to 90%, or up to 100% of the total payload contained within the depot 100. As a result, if any single sub-region 202 of the therapeutic region 200 is compromised, it can release only a proportionate fraction of the total payload of the depot.

In some embodiments, each of the therapeutic regions and each of the control regions is a micro-thin layer. In some embodiments, the depot comprises from about 2 to about 100 therapeutic regions, or from about 2 to about 50 therapeutic regions, or from about 2 to about 10 therapeutic regions.

FIGS. 9A-11 show some aspects of the present technology in which the depots 100 may have one or more therapeutic regions 200 completely enclosed or surrounded by one or more control regions 300. In contrast to the previously described embodiments, at least one therapeutic region of such fully-enclosed embodiments does not have any exposed surface area. For example, as shown in FIGS. 9A and 9B, in some embodiments the depot 100 may comprise a therapeutic region 200 surrounded or fully-enclosed by a control region 300 such that no portion of the therapeutic region 200 is exposed through the control region 300. As a result, the control region 300 substantially prevents contact between the therapeutic agent and physiologic fluids, thereby preventing an uncontrolled, burst release of the therapeutic agent when implanted. Over time, the releasing agent imbedded in the polymer of the control region contacts physiologic fluids and dissolves, thereby forming micro-diffusion openings in the control region. The combination of the restriction imposed by the control region and the micro-diffusion openings formed by dissolution of the releasing agent enables a controlled, linear release of the therapeutic agent from the depot over the course of several days, weeks, or months. Although the depot 100 is shown as a rectangular, thin film in FIGS. 9A and 9B, in other embodiments the depot 100 may have other shapes, sizes, or forms.

FIG. 10 illustrates a depot 100 having a therapeutic region fully-enclosed by a control region 300 having a first control region 300a and a second control region 300b. As depicted in FIG. 10, in some embodiments the therapeutic region 200 may be sandwiched between the first control region 300a and the second control region 300b, and the first and second control regions 300a-b may be bonded via heat compression around the therapeutic region 200 to enclose the therapeutic region 200 therebetween. In certain embodiments, a bioresorbable polymer may be wrapped around the entire depot and sealed on the top or bottom surface creating a control region structure similar to that depicted in FIG. 9A. The outer portion of the first and second control regions 300a-b may be incorporated as the final wrapped layer to seal the edges. Additionally, the first and second control regions 300a-b can be integrally formed with each other using dip coating and/or spray coating techniques, such as dipping the therapeutic region 200 in a solution of the control region material or spraying a solution of control region material onto the surfaces of the therapeutic region 200.

In FIG. 10, the first control region 300a can have first and second sub-regions 302a-b, and the second control region 300b can have first and second sub-regions 302c-d. The first control region 300a can define a top control region member, and the first and second sub-regions 302a-b can comprise a first top control layer and a second top control layer, respectively. The second control region 300b can define a bottom control region member, and the first and second sub-regions 302c-d can comprise a first bottom control layer and a second bottom control layer, respectively. The first and second top/bottom control layers can be any variation of the first and second control sub-regions discussed above with reference to FIG. 5. In addition, the first top control layer of the top control region member may have the same or different properties (e.g., thickness, polymer, releasing agent, concentration of releasing agent, total amount of releasing agent, polymer to releasing agent ratio, etc.) as the first bottom control layer of the bottom control region member. Similarly, the second top control layer of the top control region member may have the same or different properties as the second bottom control layer of the bottom control region member. Variations in the loading and construction of the layers may be designed into the depot 100 to achieve a release profile or kinetics that suits the objectives of the intended therapy. In other embodiments, the first control region 300a and/or the second control region 300b has a single layer.

FIG. 11 shows some embodiments in which the depot 100 may have a therapeutic region 200 fully-enclosed by a control region 300 having different sub-region configurations. The depot 100 of FIG. 11 includes a first control region 300a and a second control region 300b that together fully enclose the therapeutic region 200. In contrast to the depot 100 shown in FIG. 10, the first control region 300a has an outer top control region 301a with first and second top sub-control regions 302a and 302b, respectively, and an inner top control region 301b with first and second top layers 303a and 303b. The first and second top layers 303a-b are over only the top surface of the therapeutic region 200, while the first and second top sub-control regions 302a-b cover a portion the sidewall of the therapeutic region 200 and the inner top control region 301b. The second control region 300b has an outer bottom control region 301c with first and second bottom sub-control regions 302c and 302d, respectively, and an inner bottom control region 301d with first and second bottom layers 303d and 303e, respectively. As such, when the depot 100 is positioned at the treatment site in vivo, the outer top and bottom control regions 301a and 301c are between: (a) the therapeutic region 200 and the inner top and bottom control regions 301b and 301d, respectively, and (b) physiologic fluids at the treatment site. In certain embodiments, such as that shown in FIG. 11, one or more of the outer top/bottom control regions 301a/301c may comprise one or more control sub-regions, and one or more inner top/bottom control regions 301b/301d may include one or more control sub-regions.

Figure 12:
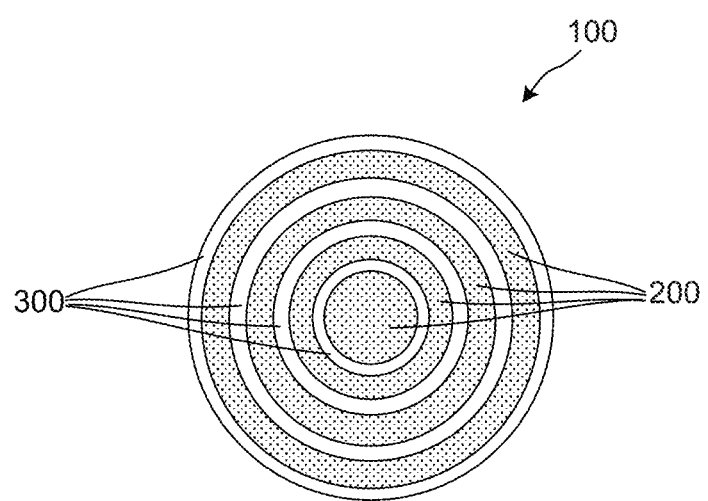
FIG. 12 is a cross-sectional view of a depot in accordance with some embodiments of the present technology.

FIG. 12 shows a cross-section of a spherical depot 100 in accordance with several embodiments of the present technology having a plurality of alternating therapeutic regions 200 and control regions 300 in accordance with the present technology. The depot 100 may have two or more control regions 300 (e.g., 2, 3, 4, 5, 6, 7, 8, 9, 10, 20, etc.), and the depot may have one or more therapeutic regions 200 (e.g., 1, 2, 3, 4, 5, 6, 7, 10, 15, 20, etc.) surrounded by at least one control region 300. In some embodiments, each of the therapeutic regions 200 may comprise a single layer and/or each of the control regions 300 may comprise a single layer. In some embodiments, one, some, or all of the therapeutic regions 200 may comprise multiple layers and/or one, some, or all of the control regions 300 may comprise multiple layers. Moreover, one or more of the individual control regions 200 and/or one or more of the therapeutic regions 300 may have the same or different amounts and/or types of releasing agent, and one or more of the therapeutic regions 200 may have the same or different amounts and/or types of therapeutic agent.

Figure 13:
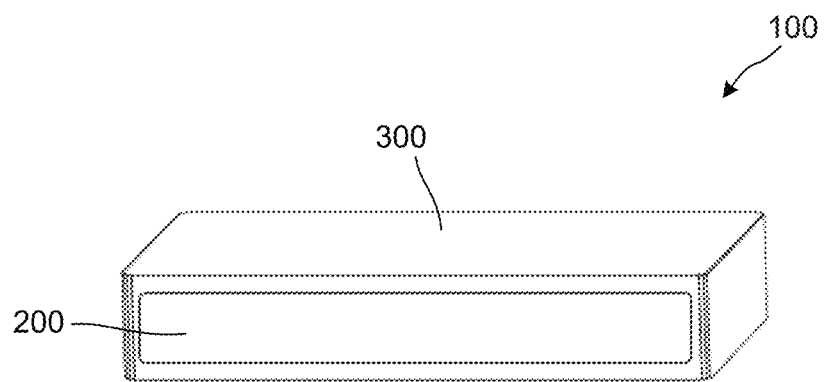
FIG. 13 is an isometric view of a depot in accordance with some embodiments of the present technology.

FIG. 13 shows a depot 100 in accordance with several embodiments of the present technology having a therapeutic region 200 enclosed on the top and bottom surfaces as well as two of four sides of the sidewall by a control region 300. This configuration is expected to release the therapeutic agent more slowly, at least initially, compared to a depot with the same dimensions and fully exposed sidewalls (see, e.g., the depot 100 shown in FIG. 4).

The release kinetics of the depots of the present technology may also be tuned for a particular application by varying the shape and size of the depot 100. Depending on the therapeutic dosage needs, anatomical targets, etc., the depot 100 can be different sizes, shapes, and forms for implantation and/or injection in the body by a clinical practitioner. The shape, size, and form of the depot 100 should be selected to allow for ease in positioning the depot at the target tissue site, and to reduce the likelihood of, or altogether prevent, the depot from moving after implantation or injection. This may be especially true for depots being positioned within a joint (such as a knee joint), wherein the depot is a flexible solid that is structurally capable of being handled by a clinician during the normal course of a surgery without breaking into multiple pieces and/or losing its general shape. Additionally, the depot may be configured to be placed in the knee of a patient and release the analgesic in vivo for up to 7 days without breaking into multiple pieces.

Some of the form factors producible from the depot 100 or to be used adjunctive to the depot for implantation and fixation into the body include: strips, ribbons, hooks, rods, tubes, patches, corkscrew-formed ribbons, partial or full rings, nails, screws, tacks, rivets, threads, tapes, woven forms, t-shaped anchors, staples, discs, pillows, balloons, braids, tapered forms, wedge forms, chisel forms, castellated forms, stent structures, suture buttresses, coil springs, sponges, capsules, coatings, matrices, wafers, sheets, strips, ribbons, pills, pellets.

The depot 100 may also be processed into a component of the form factors mentioned in the previous paragraph. For example, the depot could be rolled and incorporated into tubes, screws, tacks, or the like. In the case of woven embodiments, the depot may be incorporated into a multi-layer woven film/braid/mesh wherein some of the filaments used are not the inventive device. In one example, the depot is interwoven with Dacron, polyethylene or the like. For the sake of clarity, any form factor corresponding to the depot of the present technology, including those where only a portion or fragment of the form factor incorporates the depot, may be referred to herein as a "depot."

Figure 14A:
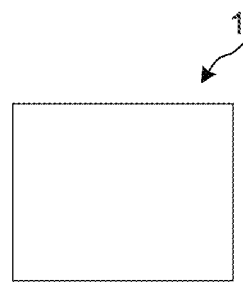
FIGS. 14A-H are depots having different cross-sectional areas and shapes in accordance with the present technology.
Figure 14B:
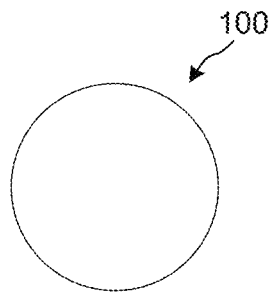
Figure 14C:
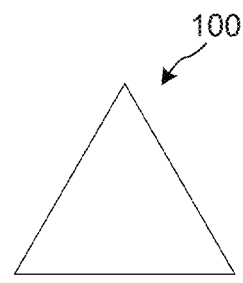
Figure 14D:
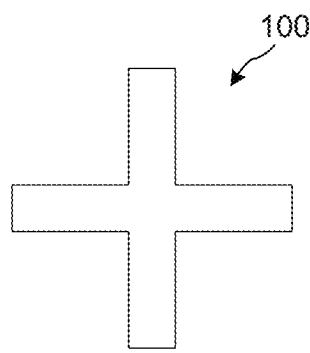
Figure 14E:
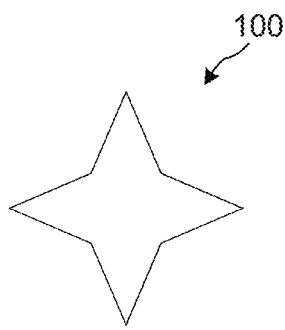
Figure 14F:
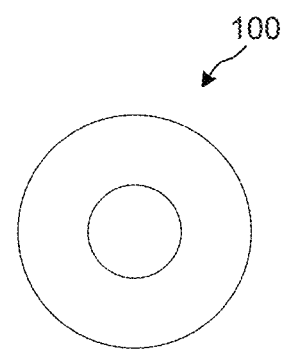
Figure 14G:
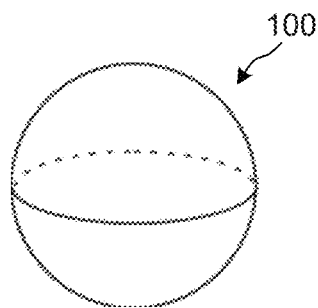
Figure 14H:
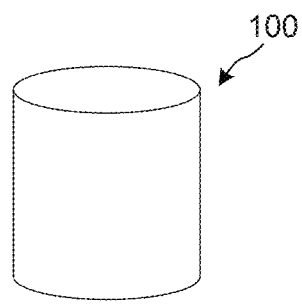

As shown in FIGS. 14A-14H, in various embodiments, the depot can be shaped like a sphere, a cylinder such as a rod or fiber, a flat surface such as a disc, film, ribbon, strip or sheet, a paste, a slab, microparticles, nanoparticles, pellets, mesh or the like. FIG. 14A shows a rectilinear depot 100. FIG. 14B shows a circular depot 100. FIG. shows a triangular depot 100. FIG. 14D show cross-like depot 100, FIG. 14E shows a star-like depot 100, and FIG. 14F shows a toroidal depot 100. FIG. 14G shows a spheroid depot 100, and FIG. 14H shows a cylindrical depot 100. The shape of the depot 100 can be selected according to the anatomy to fit within a given space and provide the desired fixation and flexibility properties. This is because the fit, fixation and flexibility of the depot may enhance the ease of implanting the depot, ensure delivery of the therapeutic agent to the target site, and prolong the durability of the implant in dynamic implant sites.

In various embodiments, the depot can be different sizes, for example, the depot may be a length of from about 0.4 mm to 100 mm and have a diameter or thickness of from about 0.01 to about 5 mm. In various embodiments, the depot may have a layer thickness of from about 0.005 to 5.0 mm, such as, for example, from 0.05 to 2.0 mm. In some embodiments, the shape may be a rectangular or square sheet having a ratio of width to thickness in the range of 20 or greater, 25 or greater, 30 or greater, 35 or greater, 40 or greater, 45 or greater, or 50 or greater.

In some embodiments, a thickness of the control region (a single sub-control region or all sub-control regions combined) is less than or equal to $1/50$, $1/75$, or $1/100$ of a Thickness of the therapeutic region.

In some embodiments, the depot 100 has a width and a thickness, and a ratio of the width to the thickness is 21 or greater. In some embodiments, the ratio is 22 or greater, 23 or greater, 24 or greater, 25 or greater, 26 or greater, 27 or greater, 28 or greater, 29 or greater, 30 or greater, 35 or greater, 40 or greater, 45 or greater, or 50 or greater.

In some embodiments, the depot 100 has a surface area and a volume, and a ratio of the surface area to volume is at least 1, at least 1.5, at least 2, at least 2.5, or at least 3.

In any of the foregoing embodiments shown and described above with respect to FIGS. 2-14H, dissolution of the releasing agent(s) and elution of the therapeutic agent(s) can change functional mechanical aspects of the depot 100 overtime. Such mechanical aspects include structural integrity, flexural strength, tensile strength, or other mechanical characteristics of the depot 100. In some instances, undesirable degradation of the depot 100, such as premature degradation, can cause mechanical failure of the depot 100 and a corresponding undesirable burst release of therapeutic agent into the body. Accordingly, it can be beneficial for the depot 100 to maintain sufficient flexural strength and/or mechanical integrity in vivo for at least a predetermined period of time or until a predetermined proportion of therapeutic agent has been released from the depot 100. The depot 100 can be considered to maintain its structural integrity if the depot 100 remains largely intact with only partial or gradual reduction due to elution of therapeutic agent or dissolution of the control layers or releasing agent. The depot 100 can be considered to lose its structural integrity if it separates (e.g., fractures) into multiple component pieces, for example, with two or more of the resulting pieces being at least 5% of the previous size of the depot 100. Alternatively, or additionally, the depot 100 can be considered to lose its structural integrity if the release rate of the therapeutic agent increases by more than a factor of three as compared to the release rate of therapeutic agent in a control depot submerged in a buffered solution.

In some embodiments, the depot 100 is configured to maintain its structural integrity in vivo for at least a predetermined length of time. For example, the depot 100 can be configured to maintain its structural integrity in vivo for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days, at least 40 days, at least 50 days, at least 60 days, at least 70 days, at least 90 days, at least 100 days, at least 200 days, at least 300 days, or at least 365 days.

In some embodiments, the depot 100 is configured to maintain its structural integrity in vivo until at least a predetermined proportion of therapeutic agent payload has been released from the depot. For example, the depot 100 can be configured to maintain its structural integrity in vivo until at least 5% by weight of the original payload has been released, at least 10% by weight of the original payload has been released, at least 15% by weight of the original payload has been released, at least 20% by weight of the original payload has been released, at least 25% by weight of the original payload has been released, at least 30% by weight of the original payload has been released, at least 35% by weight of the original payload has been released, at least 40% by weight of the original payload has been released, at least 45% by weight of the original payload has been released, at least 50% by weight of the original payload has been released, at least 55% by weight of the original payload has been released, at least 60% by weight of the original payload has been released, at least 65% by weight of the original payload has been released, at least 70% by weight of the original payload has been released, at least 75% by weight of the original payload has been released, at least 80% by weight of the original payload has been released, at least 85% by weight of the original payload has been released, at least 90% by weight of the original payload has been released, or until at least 95% by weight of the original payload has been released.

One aspect of the structural integrity of the depot 100 when it is in vivo can be quantified using a bend test, such as a three-point bend test that measures flexural properties including the flexural strength and/or maximum flexural stress sustained by a specimen before breaking. Such a bend test may represent (e.g., simulate) the forces that the depot 100 will encounter in vivo in an anatomical joint (e.g., a knee joint). In one example, a depot can be subjected to a three-point bend test based on ASTM-D790-17, "Standard Test Methods for Flexural Properties of Unreinforced and Reinforced Plastics and Electrical Insulating Materials." The text of this standard is hereby incorporated by reference in its entirety. The depot 100 may be suspended in a medium configured to simulate in vivo conditions, for example a phosphate buffered saline (PBS) at approximately 37° C. The bend test may be performed after different time periods of submersion in the medium to evaluate changes in the flexural strength of the depot 100 over time in simulated in vivo conditions.

Figure 15:
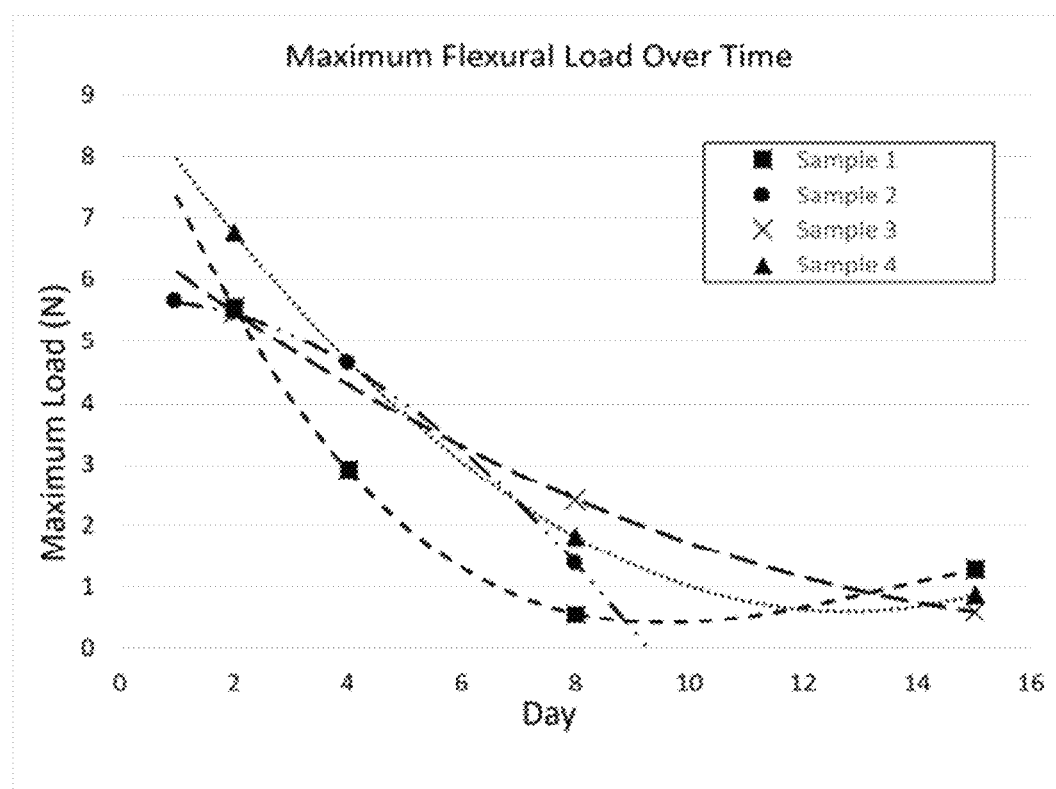
FIG. 15 depicts the maximum flexural load of an implant over time from testing performed on implant samples submerged in buffered solution.

Table 1 shows the maximum flexural load sustained by four different samples of the depot 100 at different time periods following submersion in the medium as measured using a three-point bend test with maximum deflection set at 2.13 mm. The values in Table 1 reflect measurements made from two instances of each of the listed samples. FIG. 15 is a graph illustrating these values plotted graphically and fitted with trendlines. In each of these four samples, the depot 100 includes a therapeutic region 200 surrounded by upper and lower control regions 300*a-b* as shown and described above with reference to FIG. 4 or 5. The therapeutic region 200 has exposed lateral edges 202 between the first and second control regions 300*a-b*. The depots 100 each have lateral dimensions of approximately 2.5 cm by 1.5 cm, with a thickness of approximately 1 mm.

Sample 1 is a depot having a therapeutic region with a ratio by weight of releasing agent to polymer to therapeutic agent of 0.5:10:20. The polymer in this sample is P(DL)GACL with a PDLLA:PGA:PCL ratio of 6:3:1, the releasing agent is Tween 20, and the therapeutic agent is bupivacaine hydrochloride. In this sample, the depot includes a first control region 300*a* comprising a single control layer over the upper surface of the therapeutic region 200 and a second control region 300*b* comprising single control layer over the lower surface of the therapeutic region 200, as shown and described above with reference to FIG. 4. Each control region 300*a-b* individually has a ratio of releasing agent to polymer of 5:10.

Sample 2 is a depot having a therapeutic region 200 with a ratio by weight of releasing agent to polymer to therapeutic agent of 1:10:20. The polymer in this sample is PLGA with a PLA:PGA ratio of 1:1, the releasing agent is Tween 20, and the therapeutic agent is bupivacaine hydrochloride. Similar to Sample 1, the depot of Sample 2 includes a control region 300 comprising a first control region 300*a* with a single control layer over the upper surface of the therapeutic region 200 and a second control region 300*b* comprising a single control layer over the lower surface of the therapeutic region 200, as shown and described above with reference to FIG. 4. Each control region 300*a-b* individually has a ratio of releasing agent to polymer of 5:10.

Sample 3 is a depot having therapeutic region 200 with a ratio by weight of releasing agent to polymer to therapeutic agent of 5:10:20. The polymer in this sample is P(DL)GACL with a PDLLA:PGA:PCL ratio of 6:3:1, the releasing agent is Tween 20, and the therapeutic agent is bupivacaine hydrochloride. In this sample, the depot includes a control region 300 comprising a first control region 300*a* with two sub-control regions 302*a-b* over the upper surface of the therapeutic region 200, and a second control region 300*b* with two sub-control regions 302*c-d*, as shown and described above with reference to FIG. 5. Each of the inner sub-control regions 302*b* and 302*c* contacts the surface of the therapeutic region 200 and has a ratio of releasing agent to polymer of 5:10, and each of the outer sub-control regions 302*a* and 302*d* has a ratio of releasing agent to polymer of 1:10. The depot of Sample 3, therefore, includes a total of four sub-control regions.

Sample 4 is a depot having a therapeutic region 200 with a ratio by weight of releasing agent to polymer to therapeutic agent of 5:10:20. The polymer in this sample is PLGA with a PLA:PGA ratio of 1:1, the releasing agent is Tween 20, and the therapeutic agent is bupivacaine hydrochloride. As with Sample 3, the depot of Sample 4 includes a control region 300 having first and second control region 300*a-b* that each have two sub-control regions 302*a-b* and 302*c-d*, respectively, as shown and described with respect to FIG. 5. The depot of Sample 4 according also has a total of four sub-control regions 302a-d, two over the upper surface of the therapeutic region 200 and two over the lower surface of the therapeutic region 200. The inner of the sub-control regions 302b and 302c has a ratio of releasing agent to polymer of 5:10, and the outer of the sub-control regions 302a and 302d has a ratio of releasing agent to polymer of 1:10.

TABLE 1

| Depot Sample | Day 0 | Day 1 | Day 3 | Day 7 | Day 14 | Day 28 |
|---|---|---|---|---|---|---|
| Sample 1: P(DL)GACL 6:3:1 2 control layers | No break | 5.553N 1.25 lbf | 2.903N 0.0653 lbf | 0.569N 0.134 lbf | 1.263N 0.284 lbf | Not tested |
| Sample 2: PLGA 1:1 2 control layers | 5.623N 1.264 lbf | 5.447N 1.22 lbf | 4.623N 1.04 lbf | 1.386N 0.312 lbf | Not tested | Not tested |
| Sample 3: P(DL)GACL 6:3:1 4 control layers | No break | 5.474N 1.23 lbf | Not tested | 2.430N 0.546 lbf | 0.605N 0.136 lbf | Sample degraded |
| Sample 4: PLGA 1:1 4 control layers | No break | 6.763N 1.52 lbf | Not tested | 1.816N 0.408 lbf | 0.869N 0.195 lbf | Sample degraded |

As shown in Table 1, all samples were intact and maintained sufficient structural integrity after 14 days of being suspended in the medium to withstand a bending force before fracturing. Although the maximum load tolerated by each sample decreased over time, the flexural strength of these samples at 14 days was sufficient to maintain the structural integrity desired for implantation in an active joint, such as the knee or shoulder. As shown above, for two of the samples tested at 28 days, the samples had degraded such that the test could not be performed because the sample was no longer structurally intact. In such instances, it may be desirable to configure the depots such that all or substantially all the therapeutic agent payload has been released from the depot prior to its degradation and loss of structural integrity.

In this series of experiments summarized in Table 1, the sample depots are generally flexible at Day 0 before submersion in PBS. Following submersion, the flexural strength of the depots decreased such that the depots became more brittle with time. Yet, at 7-14 days, the depots were still sufficiently functionally intact. Without being bound by theory, it is believed that after the therapeutic agent has eluted, the depots gradually become an empty polymer matrix. For example, after 14-28 days in the solution, the depots may weigh only approximately 30% of their starting weight before submersion in the PBS. At this lower weight and in the porous state, the depots may be more brittle, with lower flexural strength and less resistance to bending loads.

As noted above, it can be advantageous for the depots 100 to maintain their structural integrity and flexural strength even while they gradually degrade as the therapeutic agent payload releases into the body. In some embodiments, the depot 100 can be configured such that, in in vitro testing utilizing a three-point bend test, the flexural strength of the depot 100 decreases by no more than 95%, no more than 90%, no more than 85%, no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% after being submerged in PBS for a predetermined period of time. In various embodiments, the predetermined period of time that the depot 100 is submerged in PBS before being subjected to the three-point bend test is 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, after 21 days, after 22 days, 23 days, 24 days, 25 days, 26 days, 27 days, 28 days, or more. In at least some embodiments, the change in flexural strength of the depot 100 can be measured between day 0 (e.g., before submersion in the PBS) and a subsequent time after some period of submersion in PBS. In other embodiments, the change in flexural strength of the depot 100 can be measured between day 1 (e.g., after 24 hours of submersion in PBS) and a subsequent time following longer submersion in PBS.

In some embodiments, the depot 100 can be configured such that, in in vitro testing utilizing a three-point bend test, the flexural strength of the depot 100 decreases by no more than 95%, no more than 90%, no more than 85%, no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% over the time period in which a predetermined percentage of the initial therapeutic agent payload is released while the depot 100 is submerged in PBS. In various embodiments, the predetermined percentage of payload released when the depot 100 is submerged in PBS before being subjected to the three-point bend test is about 5%, about 10%, about 15%, about 20%, about 25%, about 30%, about 35%, about 40%, about 45%, about 50%, about 55%, about 60%, about 65%, about 70%, about 75%, about 80%, about t 85%, about 90%, or about 95%. As noted above, in at least some embodiments, the change in flexural strength of the depot 100 can be measured between day 0 (prior to submersion in PBS) or day 1 (after 24 hours of submersion in PBS) and a subsequent following longer submersion in PBS.

In some embodiments, the depot 100 has (a) lateral dimensions of about 1.0-3.0 cm, (b) a thickness of about 0.5-2.5 mm, and (c) a payload of therapeutic agent sufficient to release about 100 mg to about 500 mg of therapeutic agent per day for up to 7, 8, 9, 10, 11, 12, 13, 14, 15, 16, 17, 18, 19, or 20 days, and the depot 100 is configured to remain sufficiently mechanically intact to provide sustained, controlled release of therapeutic agent for at least 7 days. Such embodiments of the depot 100 can comprise the therapeutic region 200 with a therapeutic agent and the control region 300. The control region 300 can have first and second control regions 300a-b, such as those shown and described above with reference to FIGS. 4-13, and the control region 300 comprises a bioresorbable polymer and a releasing agent mixed with the bioresorbable polymer. The releasing agent is configured to dissolve when the depot 100 is placed in vivo to form diffusion openings in the control region 300. The depot 100 is further configured such that, following submersion of the depot 100 in a buffer solution for seven days, the flexural strength of the depot 100 decreases by no more than 75%, or by no more than 70%, or by no more than 65%, or by no more than 60%, or by no more than 55%, or by no more than 50%, or by no more than 45%

In some embodiments, the depot 100 has (a) lateral dimensions of about 1.0-3.0 cm, (b) a thickness of about 0.5-2.5 mm, and (c) a payload of therapeutic agent sufficient to release about 100 mg to about 500 mg of therapeutic agent per day for up to 7, 8, 9, 10, 11, 12, 13, 14, 15, 16, 17, 18, 19, or 20 days, and the depot 100 is configured to remain sufficiently mechanically intact to provide sustained, controlled release of therapeutic agent for at least 7 days. Such embodiments of the depot 100 can comprise the therapeutic region 200 with a therapeutic agent and the control region 300. The control region 300 can have first and second control regions 300*a-b*, such as those shown and described above with reference to FIGS. 4-13, and the control region 300 comprises a bioresorbable polymer and a releasing agent mixed with the bioresorbable polymer. The releasing agent is configured to dissolve when the depot 100 is placed in vivo to form diffusion openings in the control region 300. The depot is further configured such that, following submersion of the depot in buffer solution until approximately 75% of the therapeutic agent by weight has been released, the flexural strength of the depot decreases by no more than 75%, or by no more than 70%, or by no more than 65%, or by no more than 60%, or by no more than 55%, or by no more than 50%, or by no more than 45%.

A. Therapeutic Region

The total payload and release kinetics of the depots 100 of the present technology may be tuned for a particular application by varying the composition of the therapeutic region 200. In many embodiments, the therapeutic region 200 may include a high therapeutic payload of the therapeutic agent, especially as compared to other known polymer devices of equal thickness or polymer weight percentage. In some embodiments, the ratio of releasing agent to polymer to therapeutic agent in the therapeutic region 200 is of from about 0.1:10:20 to about 2:10:20, and in some embodiments of from about 0.1:10:20 to about 1:10:20, and in some embodiments of from about 0.1:10:20 to about 0.5:10:20, and in some embodiments of from about 0.5:10:20 to about 0.1:10:20

In some embodiments the therapeutic region 200 (or one or more therapeutic sub-regions) comprises the therapeutic agent as an essentially pure compound or formulated with a pharmaceutically acceptable carrier such as diluents, adjuvants, excipients or vehicles known to one skilled in the art. In some embodiments, the therapeutic region 200 may comprise a single layer, and in some embodiments the therapeutic region may include a plurality of microlayers containing the therapeutic agent in the same and/or different amounts. In some embodiments, the therapeutic region 200 may comprise one or more sub-regions containing the therapeutic agent and a polymer and/or releasing agent, and (b) one or more sub-regions containing the therapeutic agent as an essentially pure compound (i.e., without any polymer and/or releasing agent). In some embodiments, the therapeutic region 200 includes releasing agent, and in some embodiments, the therapeutic region 200 does not include any releasing agent prior to implantation of the depot 100 at the treatment site.

In some aspects of the technology, the therapeutic region 200 may comprise a microlayer structure of multiple micro-thin sheets of biodegradable, bioresorbable polymer, each micro-thin sheet (or layer) loaded with therapeutic agent. In this microlayer embodiment of the therapeutic region 200, the micro-thin sheets may have a substantially uniform construction and are stacked and bonded together. These micro-thin polymer sheets may each have a thickness from approximately 5 µm to 100 µm, 5 µm to 50 µm, 5 µm to 25 µm, 5 µm to 10 µm, 5 µm to 7 µm, or 7 to 9 µm thick, with the overall thickness of the therapeutic region based on the total number of micro-thin sheets that are stacked. Having a therapeutic region 200 with multiple layers may provide a more linear, controlled release of the therapeutic agent over time (beyond the first day of implantation). In addition, layering of the therapeutic region may also contribute to a more flexible, structurally competent depot (as compared to a depot having a therapeutic region comprised of pure therapeutic agent). Such durability is beneficial for the clinician when handling/manipulating the depot before and while positioning the depot 100 at a treatment site.

B. Control Region

The composition of the control region 300 may also be varied. For example, in many embodiments, the control region 300 does not include any therapeutic agent at least prior to implantation of the depot at the treatment site. In some embodiments, the control region 300 may include a therapeutic agent which may be the same as or different than the therapeutic agent in the therapeutic region 200.

Within the control region 300, the amount of releasing agent may be varied to achieve a faster or slower release of the therapeutic agent. In those embodiments where both the therapeutic region 200 and control region 300 include a releasing agent, the type of releasing agent within the therapeutic region 200 may be the same or different as the releasing agent in the control region 300. In some embodiments, a concentration of a first releasing agent within the control region is the greater than a concentration of a second releasing agent (the same or different as the first releasing agent) within the therapeutic region. In some embodiments, a concentration of the releasing agent within the control region is the less than a concentration of the releasing agent within the therapeutic region. In some embodiments, a concentration of the releasing agent within the control region 300 is the same as a concentration of the releasing agent within the therapeutic region 200.

As previously mentioned, in some embodiments the depot 100 may include a control region 300 comprised of multiple layers. In some embodiments, one, some, or all of the layers within the control region comprise a micro-thin sheet. Without being bound by theory, it is believed that such a multilayer configuration improves the control region's ability to control the release of the therapeutic agent (as compared to a single layer control region). As shown, the channels left by dissolution of the releasing agent in both microlayers of the control region create a path for a released therapeutic agent to travel that is longer and, potentially, more cumbersome to traverse as compared to the more direct path created by the channels in the single layer control region. The multiple micro-thin sheets of the control region in this embodiment may be heat compressed together on the therapeutic region 200 to regulate the therapeutic agent release rate by allowing a releasing agent to form independent non-contiguous channels through each control region from the in vivo environment to the therapeutic region. Having a control region 300 with multiple layers may provide a more linear, controlled release of the therapeutic agent over time (beyond the first day of implantation). In addition, layering of the control region 300 may also contribute to a more flexible, structurally competent depot (as compared to a depot having a therapeutic region comprised of pure therapeutic agent). Such durability is beneficial for the clinician when handling/manipulating the depot 100 before and while positioning the depot 100 at a treatment site.

In various embodiments of the depots disclosed herein, the control region may take several different forms. In some embodiments (for example, FIG. 4), the control region may comprise a single layer on either side of the therapeutic region 200 comprised of biodegradable, bioresorbable polymer mixed with a releasing agent. In some embodiments, the control region itself may comprise a structure having multiple layers of biodegradable, bioresorbable polymer. The layers of this multiple layer structure may additionally or alternatively comprise multiple micro-thin sheets or layers (i.e., microlayers), where each micro-thin layer has a thickness of from approximately 5 µm to 100 µm, 5 µm to 50 µm, 5 µm to 25 µm, 5 µm to 10 µm, 5 µm to 7 µm, or 7 µm to 9 µm. In these multi-layered embodiments of the control region 300, at least one layer of the multilayer structure may comprise a polymer mixed with a releasing agent and at least one other layer of the multilayer structure may comprise a polymer having no releasing agent mixed therein. In some embodiments, the control region 300 may comprise a multilayer structure wherein multiple layers have a releasing agent mixed into each polymer layer, but these layers may have the releasing agent in different concentrations. In particular embodiments, the multiple control layers have a releasing agent mixed into each polymer layer, and at least one of the layers may have a different releasing agent than at least one of the other layers.

C. Therapeutic Agents

The therapeutic agent carried by the depots 100 of the present technology may be any biologically active substance (or combination of substances) that provides a therapeutic effect in a patient in need thereof. As used herein, "therapeutic agent" or "drug" may refer to a single therapeutic agent, or may refer to a combination of therapeutic agents. In some embodiments, the therapeutic agent may include only a single therapeutic agent, and in some embodiments, the therapeutic agent may include two or more therapeutic agents for simultaneous or sequential release.

In several embodiments, the therapeutic agent includes an analgesic agent. The term "analgesic agent" or "analgesic" includes one or more local or systemic anesthetic agents that are administered to reduce, prevent, alleviate or remove pain entirely. The analgesic agent may comprise a systemic and/or local anesthetic, narcotics, and/or anti-inflammatory agents. The analgesic agent may comprise the pharmacologically active drug or a pharmaceutically acceptable salt thereof. Suitable local anesthetics include, but are not limited to, bupivacaine, ropivacaine, mepivacaine, etidocaine, levobupivacaine, trimecaine, carticaine, articaine, lidocaine, prilocaine, benzocaine, procaine, tetracaine, chloroprocaine, and combinations thereof. Preferred local anesthetics include bupivacaine, lidocaine and ropivacaine. Typically, local anesthetics produce anesthesia by inhibiting excitation of nerve endings or by blocking conduction in peripheral nerves. Such inhibition is achieved by anesthetics reversibly binding to and inactivating sodium channels. Sodium influx through these channels is necessary for the depolarization of nerve cell membranes and subsequent propagation of impulses along the course of the nerve. When a nerve loses depolarization and capacity to propagate an impulse, the individual loses sensation in the area supplied by the nerve. Any chemical compound possessing such anesthetic properties is suitable for use in the present technology.

In some embodiments, the therapeutic agent includes narcotics, for example, cocaine, and anti-inflammatory agents. Examples of appropriate anti-inflammatory agents include steroids, such as prednisone, betamethasone, cortisone, dexamethasone, hydrocortisone and methylprednisolone. Other appropriate anti-inflammatory agents include non-steroidal anti-inflammatory drugs (NSAIDs), such as aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, and other COX-2 inhibitors, and combinations thereof.

In some embodiments, the therapeutic agent comprises an antibiotic, an antimicrobial or antifungal agent or combinations thereof. For example, suitable antibiotics and antimicrobials include, but are not limited to, amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, and α-protegrins. Antifungal agents include, but are not limited to, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, and amphotericin B.

In several embodiments, the therapeutic agent may be an adrenocorticostatic, a β-adrenolytic, an androgen or antiandrogen, an antianemic, a antiparasitic, an anabolic, an anesthetic or analgesic, an analeptic, an antiallergic, an antiarrhythmic, an anti-arteriosclerotic, an antibiotic, an antidiabetic, an antifibrinolytic, an anticonvulsive, an angiogenesis inhibitor, an anticholinergic, an enzyme, a coenzyme or a corresponding inhibitor, an antihistaminic, an antihypertensive, an antihypotensive, an anticoagulant, an antimycotic, an antiseptic, an anti-infective, an antihemorrhagic, a β-receptor antagonist, a calcium channel antagonist, an antimyasthenic, an antiphlogistic, an antipyretic, an antirheumatic, a cardiotonic, a chemotherapeutic, a coronary dilator, a cytostatic, a glucocorticoid, a hemostatic, an immunoglobulin or its fragment, a chemokine, a cytokine, a mitogen, a cell differentiation factor, a cytotoxic agent, a hormone, an immunosuppressant, an immunostimulant, a morphine antagonist, an muscle relaxant, a narcotic, a vector, a peptide, a (para)sympathicomimetic, a (para)sympatholytic, a protein, a cell, a selective estrogen receptor modulator (SERM), a sedating agent, an antispasmodic, a substance that inhibits the resorption of bone, a vasoconstrictor or vasodilator, a virustatic or a wound-healing agent.

In various embodiments, the therapeutic agent comprises a drug used in the treatment of cancer or a pharmaceutically acceptable salt thereof. Such chemotherapeutic agents include antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include, but are not limited to, adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, beta-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, vindesine, and tamoxifen.

In some embodiments, the therapeutic agent comprises a botulinum toxin (or neurotoxin) drug used in the treatment of various neuromuscular and/or neuroglandular disorders and neuropathies associated with pain. The botulinum toxin (or neurotoxin) may comprise the pharmacologically active drug or a pharmaceutically acceptable salt thereof. The botulinum toxin (or neurotoxin) as described and used herein may be selected from a variety of strains of *Clostridium botulinum* and may comprise the pharmacologically active drug or a pharmaceutically acceptable salt thereof. In one embodiment, the botulinum toxin is selected from the group consisting of botulinum toxin types A, B, C, D, E, F and G. In a preferred embodiment, the botulinum toxin is botulinum toxin type A. Commercially available botulinum toxin, BOTOX® (Allergan, Inc., Irvine, CA), consists of a freeze-dried, purified botulinum toxin type A complex, albumin and sodium chloride packaged in sterile, vacuum-dried form.

The paralytic effect of botulinum toxin is the most common benefit of commercial therapeutics, where muscles are relaxed in order to treat muscle dystonias, wrinkles and the like. However, it has been shown that in addition to its anti-cholinergic effects on muscle and smooth muscle, the neurotoxin can have therapeutic effects on other non-muscular cell types, and on inflammation itself. For example, it has been shown that cholinergic goblet cells, which produce mucus throughout the airway system, react to and can be shut down by introduction of botulinum toxin. Research also shows that botulinum toxin has direct anti-inflammatory capabilities. All of these therapeutic effects, muscle, smooth muscle, goblet cell and anti-inflammatory affects, may be derived from delivery of the toxin from the inventive devices.

A pharmaceutically acceptable salt refers to those salts that retain the biological effectiveness and properties of neutral therapeutic agents and that are not otherwise unacceptable for pharmaceutical use. Pharmaceutically acceptable salts include salts of acidic or basic groups, which groups may be present in the therapeutic agents. The therapeutic agents used in the present technology that are basic in nature are capable of forming a wide variety of salts with various inorganic and organic acids. Pharmaceutically acceptable acid addition salts of basic therapeutic agents used in the present technology are those that form non-toxic acid addition salts, i.e., salts comprising pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The therapeutic agents of the present technology that include an amino moiety may form pharmaceutically acceptable salts with various amino acids, in addition to the acids mentioned above. Suitable base salts are formed from bases which form non-toxic salts and examples are the aluminum, calcium, lithium, magnesium, potassium, sodium, zinc and diethanolamine salts.

A pharmaceutically acceptable salt may involve the inclusion of another molecule such as water or another biologically compatible solvent (a solvate), an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The therapeutic agent or pharmaceutically acceptable salt thereof may be an essentially pure compound or be formulated with a pharmaceutically acceptable carrier such as diluents, adjuvants, excipients or vehicles known to one skilled in the art. The carrier(s) must be "acceptable" in the sense of being compatible with the other ingredients of the formulations and not deleterious to the recipient thereof. For example, diluents include lactose, dextrose, sucrose, mannitol, sorbitol, cellulose, glycine and the like. For examples of other pharmaceutically acceptable carriers, see Remington: THE SCIENCE AND PRACTICE OF PHARMACY (21st Edition, University of the Sciences in Philadelphia, 2005).

The therapeutic agent or pharmaceutically acceptable salt form may be jet milled or otherwise passed through a sieve to form consistent particle sizes further enabling the regulated and controlled release of the therapeutic agent. This process may be particularly helpful for highly insoluble therapeutic agents.

In one embodiment, the biodegradable, bioresorbable polymer used in various layers of the depot may manifest as a layer of electrospun microfibers or nanofibers. Biocompatible electrospun microfibers/nanofibers are known in the art and may be used, for example, to manufacture implantable supports for the formation of replacement organs in vivo (U.S. Patent Publication No. 2014/0272225; Johnson; Nanofiber Solutions, LLC), for musculoskeletal and skin tissue engineering (R. Vasita and D. S. Katti, Int. J. Nanomedicine, 2006, 1:1, 15-30), for dermal or oral applications (PCT Publication No. 2015/189212; Hansen; Dermtreat APS) or for management of postoperative pain (U.S. Patent Publication No. 2013/0071463; Palasis et al.). As a manufacturing technique, electrospinning offers the opportunity for control over the thickness and the composition of the nano- or micro-fibers along with control of the porosity of the fiber meshes (Vasita and Katti, 2006). These electrospun scaffolds are three-dimensional and thus provide ideal supports for the culture of cells in vivo for tissue formation. Typically, these scaffolds have a porosity of 70-90% (U.S. Pat. No. 9,737,632; Johnson; Nanofiber Solutions, LLC). Suitable biodegradable polymers and copolymers for the manufacture of electrospun microfibers include, but are not limited to, natural materials such as collagen, gelatin, elastin, chitosan, silk fibrion, and hyaluronic acid, as well as synthetic materials such as poly(F-caprolactone) (PCL), poly(glycolic acid) (PGA), poly(lactic-co-glycolic acid) (PLGA), poly(1-lactide-co-F-caprolactone), and poly(lactic acid) (PLA).

Electrospun microfibers that are made from a bioresorbable polymer or copolymer and have been used in conjunction with a therapeutic agent are known in the art. For example, Johnson et al. have disclosed the treatment of joint inflammation and other conditions with an injection of biocompatible polymeric electrospun fiber fragments along with a carrier medium containing chitosan (U.S. Published Application No. 2016/0325015; Nanofiber Solutions, LLC). Weldon et al. reported the use of electrospun bupivacaine-eluting sutures manufactured from poly(lactic-co-glycolic acid) in a rat skin wound model, wherein the sutures provided local anesthesia at an incision site (J. Control Release, 2012, 161:3, 903-909). Similarly, Palasis et al. disclosed the treatment of postoperative pain by implanting electrospun fibers loaded with an opioid, anesthetic or a non-opioid analgesic within a surgical site (U.S. Patent Publication No. 2013/0071463; Palasis et al.). Electrospun microfibers suitable for use in the present technology may be obtained by the methods disclosed in the above cited references, which are herein incorporated in their entirety.

An important criterion for determining the amount of therapeutic agent needed for the treatment of a particular medical condition is the release rate of the drug from the depot of the present technology. The release rate is controlled by a variety of factors, including, but not limited to, the rate that the releasing agent dissolves in vivo into the surrounding fluid, the in vivo degradation rate of the bioresorbable polymer or copolymer utilized. For example, the rate of release may be controlled by the use of multiple control regions between the therapeutic region and the physiological fluid. See, for example, FIGS. 6-8.

Suitable dosage ranges utilizing the depot of the present technology are dependent on the potency of the particular therapeutic agent, but are generally about 0.001 mg to about 500 mg of drug per kilogram body weight, for example from about 0.1 mg to about 200 mg of drug per kilogram body weight, and about 1 to about 100 mg/kg-body wt. per day. Dosage ranges may be readily determined by methods known to one skilled in the art. Dosage unit forms will generally contain between about 1 mg to about 500 mg of active ingredient. For example, commercially available bupivacaine hydrochloride, marketed under the brand name Marcaine™ (Pfizer; New York, NY), is generally administered as a peripheral nerve block using a dosage range of 37.5-75 mg in a 0.25% concentration and 25 mg up to the daily maximum level (up to 400 mg) in a 0.5% concentration (Marcaine®™ package insert; FDA Reference ID: 3079122). In addition, commercially available ropivacaine hydrochloride, marketed under the brand name Naropin® (Fresenius Kabi USA, LLC; Lake Zurich, IL), is administered in doses of 5-300 mg for minor and major nerve blocks (Naropin® package insert; Reference ID: 451112G). Suitable dosage ranges for the depot of the present technology are equivalent to the commercially available agents customarily administered by injection.

In some embodiments, the therapeutic region 200 includes at least 15% by weight of the analgesic, at least 20% by weight of the analgesic, at least 30% by weight of the analgesic, at least 40% by weight of the analgesic, at least 50% by weight of the analgesic, at least 60% by weight of the analgesic, at least 70% by weight of the analgesic, at least 80% by weight of the analgesic, at least 90% by weight of the analgesic, or 100% by weight of the analgesic.

In some embodiments, the depot includes at least 15% by weight of the analgesic, at least 20% by weight of the analgesic, at least 30% by weight of the analgesic, at least 40% by weight of the analgesic, at least 50% by weight of the analgesic, at least 60% by weight of the analgesic, at least 70% by weight of the analgesic, at least 80% by weight of the analgesic, at least 90% by weight of the analgesic, or 100% by weight of the analgesic. In many embodiments, the depot 100 includes at least 50% by weight of the analgesic.

In some aspects of the technology, the therapeutic region 200 may include multiple layers. In such embodiments, the multiple layers may improve efficient loading of therapeutic agents. For example, multilayering may be a direct and effective way of loading substantial amounts of therapeutic agent. It can often be challenging to load a large amount of therapeutic agent in a single film layer, even by increasing the drug to polymer ratio or increasing the thickness of the layer. Even when the thickness of the therapeutic region can be theoretically increased to load more drug, consistent fabrication of a thick therapeutic region via casting could prove to be a challenge. In contrast, the stacking and bonding of thin films or sheets, each with a predetermined load of therapeutic agent, may present as a more reliable casting alternative. Data from an example of loading an analgesic (i.e., ropivacaine) is provided in Table 2.

TABLE 2

|  | Drug Load (ug) | Thickness (mm) |
| --- | --- | --- |
| Single layer | 212.66 | 0.019 |
| Five layers | 1120.83 | 0.046 |
| Multiple | 5.27 | 2.42 |

As but one example, a single layer loaded with ropivacaine and having a thickness of 0.019 mm was produced. A 5-layer film sample, where each layer was loaded with ropivacaine, having a thickness of 0.046 mm was also produced. Even though the thickness of the 5-layer film sample was only 2.42 times the thickness of the single layer, the load of therapeutic agent in the 5-layer sample was 5.27 times that of the single layer sample. Accordingly, the multilayering approach enabled a substantially higher density of therapeutic agent.

As described above, heat compression bonding of multiple layers enables an effective reduction in film thickness and an increased density of therapeutic agent loading. In the example illustrated in Table 2, the multilayer structure enabled a 124% increase in the density of the therapeutic agent. In other embodiments, the increase in density of the therapeutic agent enabled by a multilayer structure of the therapeutic region may be approximately 50%, 75%, 100%, 125%, 150% or 200%.

D. Biodegradable Polymers

The depots 100 of the present technology are comprised of bioresorbable polymers. In some embodiments, both the therapeutic region 200 and the control region 300 comprise a polymer (or mix of polymers), which can be the same or different polymer (or mix of polymers) in the same or different amount, concentration, and/or weight percentage. In some embodiments, the control region 300 comprises a polymer and the therapeutic region 200 does not include a polymer. In some embodiments, the therapeutic region 200 comprises a polymer and the control region 300 does not include a polymer. At least as used in this section, "the polymer" applies to a polymer that may be used in the therapeutic region 200 and/or in the control region 300.

The bioresorbable polymers used in the present technology preferably have a predetermined degradation rate. The terms "bioresorbable," or "bioabsorbable," mean that a polymer will be absorbed within the patient's body, for example, by a cell or tissue. These polymers are "biodegradable" in that all or parts the polymeric film will degrade over time by the action of enzymes, by hydrolytic action and/or by other similar mechanisms in the patient's body. In various embodiments, the biodegradable, bioresorbable polymer film can break down or degrade within the body to non-toxic components while a therapeutic agent is being released. Polymers used as base components of the depots of the present technology may break down or degrade after the therapeutic agent is fully released. The bioresorbable polymers are also "bioerodible," in that they will erode or degrade over time due, at least in part, to contact with substances found in the surrounding tissue, fluids or by cellular action.

Criteria for the selection of the bioresorbable polymer suitable for use in the present technology include: 1) in vivo safety and biocompatibility; 2) therapeutic agent loading capacity; 3) therapeutic agent releasing capability; 4) degradation profile; 5) potential for inflammatory response; and 6) mechanical properties, which may relate to form factor and manufacturability. As such, selection of the bioresorbable polymer may depend on the clinical objectives of a particular therapy and may involve trading off between competing objectives. For example, PGA (polyglycolide) is known to have a relatively fast degradation rate, but it is also fairly brittle. Conversely, polycaprolactone (PCL) has a relatively slow degradation rate and is quite elastic. Copolymerization provides some versatility if it is clinically desirable to have a mix of properties from multiple polymers. For biomedical applications, particularly as a biodegradable depot for drug release, a polymer or copolymer using at least one of poly(L-lactic acid) (PLA), PCL, and PGA are generally preferred. The physical properties for some of these polymers are provided in Table 3 below.

et al., Materials, 2009, 2:307-44). Rapid in vivo degradation of PGA leads to loss of mechanical strength and a substantial local production of glycolic acid, which in substantial amounts may provoke an inflammatory response.

In many embodiments, the polymer may include polylactide (PLA). PLA is a hydrophobic polymer because of the presence of methyl (—CH3) side groups off the polymer backbone. It is more resistant to hydrolysis than PGA because of the steric shielding effect of the methyl side groups. The typical glass transition temperature for representative commercial PLA is 63.8° C., the elongation at break is 30.7%, and the tensile strength is 32.22 MPa (Vroman, 2009). Regulation of the physical properties and biodegradability of PLA can be achieved by employing a hydroxy acids co-monomer component or by racemization of D- and L-isomers (Vroman, 2009). PLA exists in four forms: poly(L-lactic acid) (PLLA), poly(D-lactic acid) (PDLA), meso-poly(lactic acid) and poly(D,L-lactic acid) (PDLLA), which is a racemic mixture of PLLA and PDLA. PLLA and PDLLA have been the most studied for biomedical applications.

Copolymerization of PLA (both L- and D,L-lactide forms) and PGA yields poly(lactide-co-glycolide) (PLGA), which is one of the most commonly used degradable polymers for biomedical applications. In many embodiments, the polymer may include PLGA. In many embodiments, the polymer may include PLGA. Since PLA and PGA have significantly different properties, careful choice of PLGA composition can enable optimization of performance in intended clinical applications. Physical property modulation is even more significant for PLGA copolymers. When a composition is comprised of 25-75% lactide, PLGA forms amorphous polymers which are very hydrolytically unstable compared to the more stable homopolymers. This is demonstrated in the degradation times of 50:50 PLGA, 75:25 PLGA, and 85:15 PLGA, which are 1-2 months, 4-5 months and 5-6 months, respectively. In some embodiments, the polymer may be an ester-terminated poly (DL-lactide-co-glycolide) ("PLGA") in a molar ratio of 50:50 (DURECT Corporation).

In some embodiments, the polymer may include polycaprolactone (PCL). PCL is a semi-crystalline polyester with high organic solvent solubility, a melting temperature of 55-60° C., and glass transition temperature of −54° C. (Vroman, 2009). PCL has a low in vivo degradation rate and high drug permeability, thereby making it more suitable as a depot for longer term drug delivery. For example, Capro-

TABLE 3

| Materials | Tg (° C.) [1] | Tg (° C.) [1] | Elastic Modulus (GPa) [1] | Tensile Stength (MPa) [1] | Tensile Elongation (%) [1] | Degradation Time (months) [2] |
|---|---|---|---|---|---|---|
| PLA | 45-60 | 150-162 | 0.35-3.5 | 21-60 | 2.5-6 | 12-16 |
| PLLA | 55-65 | 17-200 | 2.7-4.14 | 15.5-150 | 3-10 | >24 |
| PDLA | 50-60 | — | 1.0-3.45 | 27.6-50 | 2-10 | 6-12 |
| PLA/PGA (50:50) | 40-50 | — | 1.0-4.34 | 41.4-55.2 | 2-10 | 3 |
| PGA | 35-45 | 220-233 | 6.0-7.0 | 60-99.7 | 1.5-20 | 6-12 |
| PCL | −60--65 | 58-65 | 0.21-0.44 | 20.7-42 | 300-1000 | >24 |

In many embodiments, the polymer may include polyglycolide (PGA). PGA is one of the simplest linear aliphatic polyesters. It is prepared by ring opening polymerization of a cyclic lactone, glycolide. It is highly crystalline, with a crystallinity of 45-55%, and thus is not soluble in most organic solvents. It has a high melting point (220-225° C.), and a glass transition temperature of 35-40° C. (Vroman, L., nor® is a commercial contraceptive PCL product that is able to deliver levonorgestrel in vivo for over a year. PCL is often blended or copolymerized with other polymers like PLLA, PDLLA, or PLGA. Blending or copolymerization with polyethers expedites overall polymer erosion. Additionally, PCL has a relatively low tensile strength (~23 MPa), but very high elongation at breakage (4700%), making it a very good elastic biomaterial. PCL also is highly processable, which enables many potential form factors and production efficiencies.

Suitable bioresorbable polymers and copolymers for use in the present technology include, but are not limited to, poly(alpha-hydroxy acids), poly(lactide-co-glycolide) (PLGA or DLG), poly(DL-lactide-co-caprolactone) (DL-PLCL), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(glycolide-co-carolactone) (PGCL), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives and copolymers thereof. Other suitable polymers or copolymers include polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, or combinations thereof.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

As described above, it may be desirable in certain clinical applications using depots for controlled delivery of therapeutic agents to use copolymers comprising at least two of PGA, PLA, PCL, PDO, and PVA. These include, for example, poly(lactide-co-caprolactone) (PLCL) (e.g. having a PLA to PCL ratio of from 90:10 to 60:40) or its derivatives and copolymers thereof, poly(DL-lactide-co-caprolactone) (DL-PLCL) (e.g. having a DL-PLA to PCL ratio of from 90:10 to 50:50) or its derivatives and copolymers thereof, poly(glycolide-co-caprolactone) (PGCL) (e.g. having a PGA to PCL ratio of from 90:10 to 10:90) or its derivatives and copolymers thereof, or a blend of PCL and PLA (e.g. a ratio blend of PCL and PLA having a wt:wt ratio of 1:9 to 9:1). In one preferred embodiment, the bioresorbable polymer comprises a copolymer of polycaprolactone (PCL), poly(L-lactic acid) (PLA) and polyglycolide (PGA). In such a preferred embodiment, the ratio of PGA to PLA to PCL of the copolymer may be 5-60% PGA, 5-40% PLA and 10-90% PCL. In additional embodiments, the PGA:PLA:PCL ratio may be 40:40:20, 30:30:50, 20:20:60, 15:15:70, 10:10:80, 50:20:30, 50:25:25, 60:20:20, or 60:10:30. In some embodiments, the polymer is an ester-terminated poly (DL-lactide-co-glycolide-co-caprolactone) in a molar ratio of 60:30:10 (DURECT Corporation).

In some embodiments, a terpolymer may be beneficial for increasing the degradation rate and ease of manufacturing, etc.

To minimize the size of a bioresorbable depot, it is generally preferred to maximize the loading of therapeutic agent in the polymer to achieve the highest possible density of therapeutic agent. However, polymer carriers having high densities of therapeutic agent are more susceptible to burst release kinetics and, consequently, poor control over time release. As described above, one significant benefit of the depot structure described herein, and particularly the control region feature of the depot, is the ability to control and attenuate the therapeutic agent release kinetics even with therapeutic agent densities that would cause instability in other carriers. In certain embodiments, the therapeutic agent loading capacity includes ratios (wt:wt) of the therapeutic agent to biodegradable polymer of approximately 1:3, 1:2, 1:1, 3:2, 2:1, 3:1, 4:1, 5:1, 6:1, 7:1, 8:1, 9:1, 10:1, 12:1, 14:1, or 16:1. In some embodiments, it may be desirable to increase the therapeutic effect or potency of the therapeutic agent released from the depot described herein while still maintaining the same or similar polymer to therapeutic agent ratio. This can be accomplished by using an essentially pure form of the therapeutic agent as opposed to a salt derivative. Additionally or alternatively, the therapeutic agent can be mixed with clonidine or epinephrine, which are known to increase the therapeutic effect of certain drugs.

When implanted in a patient's joint (for example, a knee joint), the biodegradable depot described above may be positioned in the joint such that it will be articulating throughout the duration of release. So as to avoid premature release of the analgesic, it is desirable for the depot to have a threshold level of mechanical integrity and stability until most of the analgesic has been released. While it may be desirable to maximize the loading of therapeutic agent in the biodegradable depot, as described above, such maximization can typically be at the expense of mechanical integrity and stability of the depot. Given the high dosage of anesthetic necessary to provide analgesia through both the acute and subacute postoperative pain periods and limited space in the knee, it is desirable for the depot described herein to have a high density loading of anesthetic while still maintaining sufficient mechanical integrity and stability in the knee. The layered structure and, particularly, the presence of the control region provide some safeguard against the premature release of anesthetic. Moreover, the use of heat compression in the manufacturing process enables substantial loading of anesthetic into the therapeutic region while creating a thermal bond between the therapeutic region and control region, thereby preventing delamination, and a consequent uncontrolled release of drug, when the depot is subjected to mechanical stress in the knee.

It is generally desirable that the implanted polymer fully degrade following complete delivery of the therapeutic agent. Full degradation is preferred because, unless the implanted polymer provides some structural function or support, the clinical practitioner would have to reconcile leaving in a foreign body with no functional purpose, which could be a source of inflammation or infection, or perform another surgery simply to remove the remaining polymer. As an alternative to full degradation, it would be desirable for any remaining polymer to be fully encapsulated by the body.

The degradation of an implanted polymer consists essentially of two sequential processes: diffusion of an aqueous solution (i.e., physiological fluids) followed by hydrolytic degradation. Degradation usually takes one of two forms: (1) surface erosion; and (2) bulk degradation. Surface erosion of a polymer occurs when the polymer erodes from the surface inward, where hydrolytic erosion at the surface is faster than the ingress of water into the polymer. Conversely, bulk degradation occurs throughout the entire polymer, where water penetrates and degrades the interior of the material faster than the surface can erode. Polymers such as PLA, PGA, PLGA and PCL all resorb into the body via bulk degradation.

The time necessary for complete degradation can vary greatly based on the material selected and the clinical performance requirements of the depot. For example, in the case of treating and managing postoperative pain, it may be desirable for the polymer depot to release therapeutic agent (i.e., an analgesic) for anywhere from 5 to 30 days. In the case of treating or preventing infection of a prosthetic joint (e.g., knee or hip implant), it may be desirable for the polymer depot to release an anti-infective agent for anywhere from 2 to 4 months. Alternatively, even if the entire amount of therapeutic agent loaded into the polymer has been released, it may be desirable for the polymer to degrade over a longer period than the duration of drug release. For example, rapid degradation can often make the polymer brittle and fragile, thereby compromising mechanical performance, or provoking an inflammatory response from the body. In particular, it may be desirable, in certain clinical applications, to have an embodiment wherein degradation of the polymer commenced only after release of substantially all of the therapeutic agent.

In certain embodiments of the present technology, it may be desirable for the polymer to fully resorb into the body after substantially all therapeutic agent loaded therein is released. In certain embodiments, this degradation can be as short as 1 month. Alternatively, in other embodiments, full degradation could take as long as 2 months, 3 months, 4 months, 6 months, 9 months or 12 months. In some embodiments, the bioresorbable polymer substantially degrades in vivo within about one month, about two months, about three months, about four months, about five months or about six months. In some embodiments, it may be desirable for full degradation to be 6 months such that the mechanical properties of the implanted polymer are preserved for the first 2 months following implantation.

Core Acidification

Figure 17:
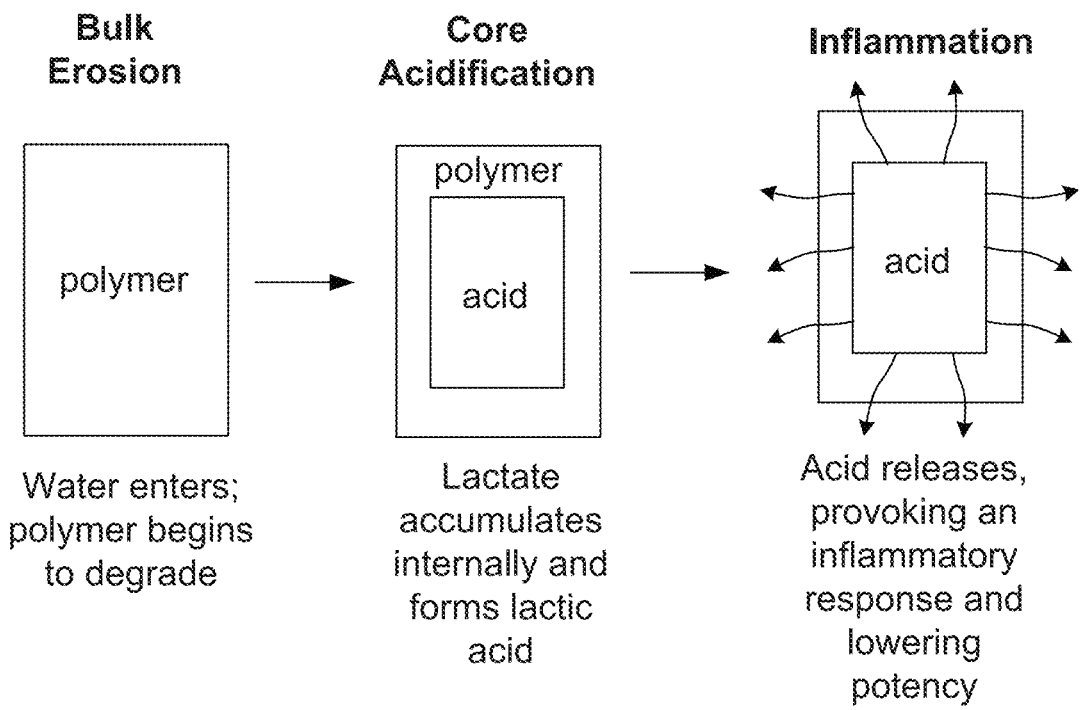
FIG. 17 is a schematic representation of core acidification of the prior art.
Figure 18:
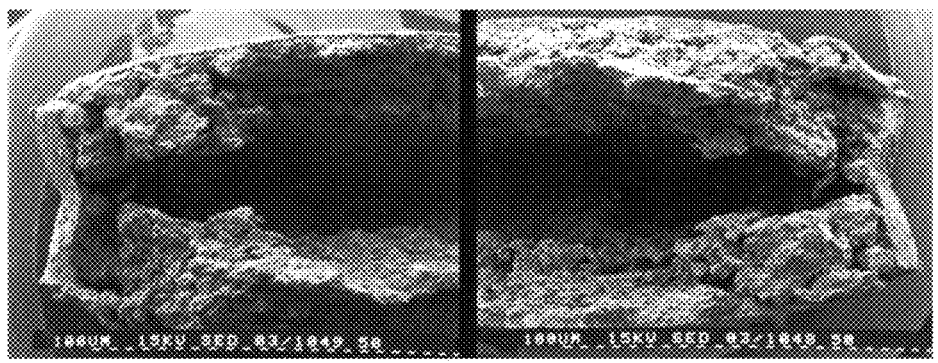
FIG. 18 is a scanning electron microscope image of a polymer tablet of the prior art after 20 days of degradation.

Traditional biodegradable orthopedic implants often lead to tissue inflammation due to a phenomenon known as "core acidification." For example, as shown schematically in FIG. 17, polymer implants having a thickness greater than 1 mm degrade by bulk erosion (i.e., degradation occurs throughout the whole material equally; both the surface and the inside of the material degrade at substantially the same time). As the polymer degrades, lactate accumulates at an internal region of the implant. Eventually, because of the high pH in the internal region of the implant, the lactate becomes lactic acid. The accumulated lactic acid will invariably release into the body, thereby provoking an inflammatory response. FIG. 18, for example, is a scanning electron microscope ("SEM") image of a polymer tablet (DL-PLGA (50:50)) of the prior art after 20 days of degradation in phosphate buffer at pH 7.4 and 37° C. (Taken from FIG. 2 of Avgoustakis, K., *Synthesis and Evaluation of Some Poly(Lactide-co-Glycolides) for Use in Sustained Release Tables*, Ph.D. thesis, University of London, 1992.) Inflammation in and around a prosthetic joint may be particularly concerning because of the risk of inflammation-induced osteolysis, which may cause a loosening of the newly implanted joint. Moreover, core acidification causes extracellular pH to drop, which then causes the amount of free base bupivacaine to drop. Only free base bupivacaine can cross the lipid bilayer forming the cell membrane into the neuron. Once bupivacaine crosses into the neuron the percent of bupivacaine HCl increases. It is the bupivacaine HCl form that is active by blocking sodium from entering the neuron thus inducing analgesia. Thus, any reduction in extracellular pH (for example, via core acidification) slows transfer of the analgesic into the neuron, thereby reducing or altogether eliminating the therapeutic effects of the analgesic.

The degree of core acidification is determined in large part by the geometry and dimensions of the polymer implant. (See, e.g., Grizzi et al., Hydrolytic degradation of devices based on poly(dl-lactic acid) size-dependence, BIOMATERIALS, 1995, Vol. 16 No. 4, pp. 305-11; Fukuzaki et al., in vivo characteristics of high molecular weight copoly(1-lactide/glycolide) with S-type degradation pattern for application in drug delivery systems, Biomaterials 1991, Vol. 12 May, pp. 433-37; Li et al., Structure-property relationships in the case of degradation of massive alipathic poly-(α-hydroxy acids) in aqueous media, JOURNAL OF MATERIALS SCIENCE: MATERIALS IN MEDICINE I (1990), pp. 123-130.) For example, degradation in more massive monolithic devices (mm-size scales and greater) proceeds much more rapidly in their interior than on their surface, leading to an outer layer of slowly degrading polymer entrapping more advanced internal degradation products from interior zone autocatalysis (so-called "S-type" non-linear kinetic degradation profile). In contrast to a thicker film, a thin film of less than 1 mm thickness will typically degrade via surface erosion, wherein the lactate resulting from degradation will not accumulate in the interior of the film. Thin films, because of their high surface area to volume ratios, are known to degrade uniformly and do not lead to core acidification. (See Grizzi et al.)

Figure 19A:
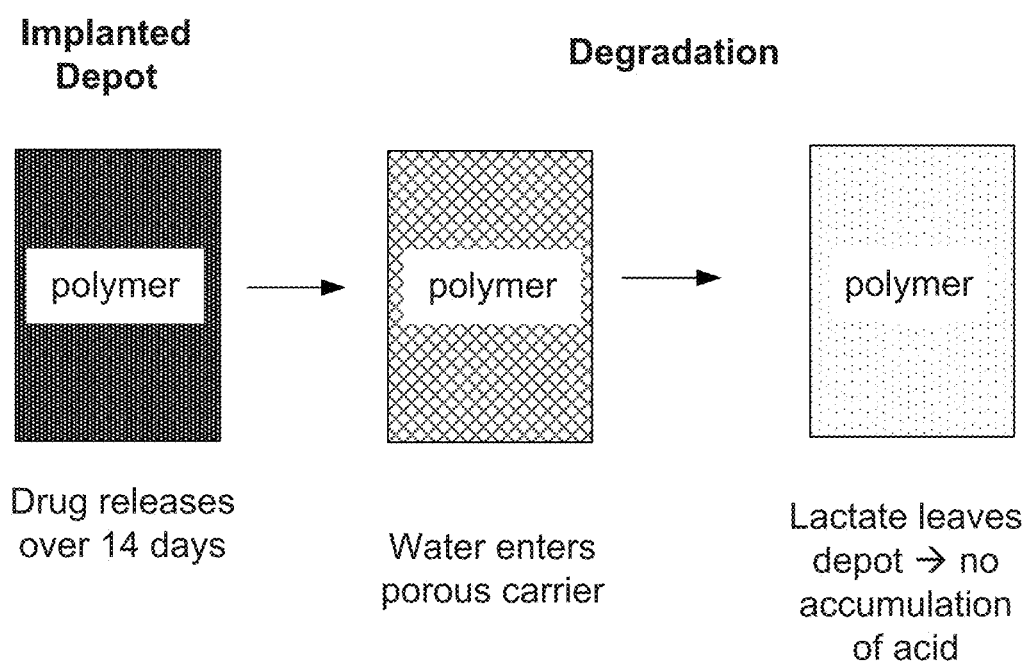
FIG. 19A is a schematic representation of the degradation of the depots of the present technology.
Figure 19B:
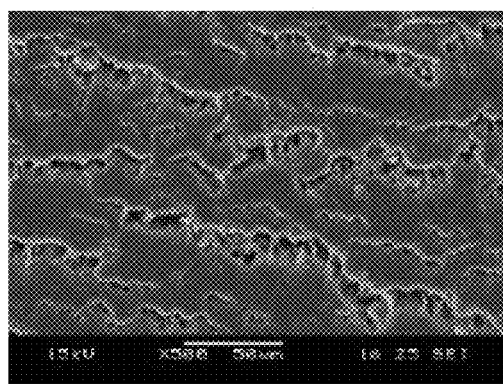
FIGS. 19B and 19C are scanning electron microscope ("SEM") images of cross-sections of depots of the present technology at different timepoints during degradation.
Figure 19C:
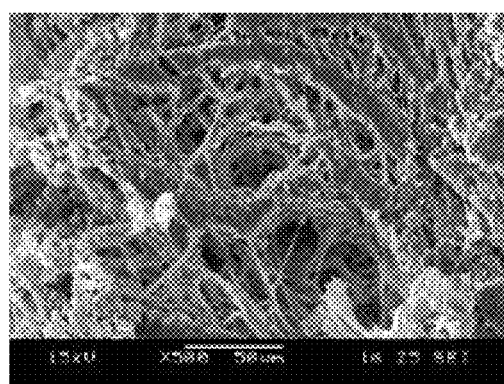

As shown schematically in FIG. 18, the depots of the present technology may shed up to 50%, 60%, 70% or 80% of their individual mass (anesthetic and releasing agent) over the course of releasing the anesthetic (e.g., 5 days, 7 days, 10 days, 14 days, 20 days, 30 days, etc.), resulting in a highly porous, mesh-like system that—at least for the purpose of degradation-behaves like a thin-film because of its high surface area to volume ratio. Body fluids will invade the highly porous polymer carrier to degrade the remaining polymer via surface erosion, thereby avoiding core acidification and the resulting inflammatory response. Without being bound by theory, it is believed that the drug core matrix of the therapeutic region becomes highly porous as degradation continues. For example, FIGS. 19B and 19C are scanning electron microscope ("SEM") images showing the therapeutic region before and after elution, respectively. However, even after the release of therapeutic agent, there is still a clear porous structure left through which water and acid can diffuse effectively. Thus, depots 100 of the present technology having a thickness greater than about 1 mm degrade like a thin film, and surprisingly do not exhibit core acidification.

E. Releasing Agent

In many implantable drug eluting technologies, the depot provides an initial, uncontrolled burst release of drug followed by a residual release. These drug release kinetics may be desirable in certain clinical applications, but may be unavoidable even when undesirable. Hydrophilic drugs loaded in a polymer carrier will typically provide a burst release when exposed to physiologic fluids. This dynamic may present challenges, particularly when it is desirable to load a large volume of drug for controlled, sustained in vivo administration. For example, although it may be desirable to implant several days or weeks' worth of dosage to achieve a sustained, durable, in vivo pharmacological treatment, it is imperative that the therapeutic agent is released as prescribed, otherwise release of the entire payload could result in severe complications to the patient.

To achieve finer control over the release of the therapeutic agent when exposed to fluids, the depots 100 of the present technology may include a releasing agent. In some embodiments, both the therapeutic region 200 and the control region 300 include a releasing agent (or mix of releasing agents), which can be the same or different releasing agent (or mix of releasing agents) in the same or different amount, concentration, and/or weight percentage. In some embodiments, the control region 300 includes a releasing agent and the therapeutic region 200 does not include a releasing agent. In some embodiments, the therapeutic region 200 includes a releasing agent and the control region 300 does not include a releasing agent. At least as used in this section, "the releasing agent" applies to a releasing agent that may be used in the therapeutic region 200 and/or in the control region 300.

The type and/or amount of releasing agent within the therapeutic region 200 and/or control region 300 may be varied according to the desired release rate of the therapeutic agent into the surrounding biological fluids. For example, choosing releasing agents with different dissolution times will affect the rate of release. Also, the weight percentage of releasing agent in a region of polymer will influence the number and the size of the diffusion openings subsequently formed in the polymer, thereby affecting the rate of therapeutic agent release from the depot 100 (e.g., the greater the weight percentage of releasing agent, the faster the release). The presence of releasing agent in select regions also influences the release rate of therapeutic agent. For example, a depot with releasing agent in the control region 300 and/or therapeutic region 200 will generally release therapeutic agent at a higher rate compared to a depot with no releasing agent. Similarly, releasing agent in both the control region 300 and the therapeutic region 200 will generally release therapeutic agent at a higher rate than when releasing agent is in the control region alone.

In certain embodiments of the present technology, the layer-by-layer ratio of releasing agent to bioresorbable polymer can be adjusted to control the rate of therapeutic agent released from the depot 100. For example, in many embodiments of the present technology, the depot 100 includes a therapeutic region 200 having a weight percentage of releasing agent that is different than the weight percentage of the releasing agent in the control region 200. For example, the therapeutic region 200 may have a greater or lesser weight percentage of releasing agent than the control region 300. In some embodiments, the control region 300 may have a weight percentage of releasing agent that is at least 2 times greater than the weight percentage of the releasing agent in the therapeutic region 200. In some embodiments, the control region 300 may have a weight percentage of releasing agent that is at least 3-20 times greater than the weight percentage of the releasing agent in the therapeutic region 200.

In many embodiments of the present technology, the releasing agent is a surfactant. Unlike the use as a releasing agent as described herein, surfactants are usually used to control the dispersions, flocculation and wetting properties of a drug or polymer. Fundamentally, surfactants operate on the interface between the polymer and drug or the interface between the drug and biological membrane. Depending on the type of formulation, surfactants typically play a role in several aspects of drug delivery: (1) solubilization or stabilization of hydrophobic drugs by lowering the entropic cost of solvating hydrophobic drug through complexation with drug molecules in solution (C. Bell and K. A. Woodrow, ANTIMICROB. AGENTS CHEMOTHER., 2014, 58:8, 4855-65); (2) improvement of the wetting of tablet or polymer for fast disintegration (M. Irfan, et al., SAUDI PHARM. J., 2016, 24, 537-46); (3) formation of colloidal drug delivery systems, such as reverse micelles, vesicles, liquid crystal dispersions, nanoemulsions and nanoparticles (M. Fanun, Colloids in Drug Delivery, 2010, p. 357); and (4) improvement the bioperformance of drugs by altering the permeability of biological membrane and consequently drug penetration/permeation profile (S. Jain, et al., Lipid Based Vesicular Drug Delivery Systems, 2014, Vol. 2014, Article ID 574673).

In order to illustrate the unique aspects of using a releasing agent in the polymeric control region to form microchannels in the present technology, it is helpful to explain the more common approach of using hydrophilic molecules to enhance drug release. Conventionally, drug release is enhanced by creating a larger surface area in order to increase contact between the drug and the bodily fluid, thereby accelerating drug release. The most common pore-forming mechanism is to use non-surfactant hydrophilic molecules as pore-forming agents in polymer layers, either as a coating layer or a free-standing film (Kanagale, P., et al., AAPS PHARM. SCI. TECH., 2007; 8(3), E1-7). Usually, pores are pre-formed by blending hydrophilic molecules with polymer, then removing the hydrophilic molecules by contact with water. However, when hydrophilic molecules are blended with hydrophobic polymer, the molecules tend to form hydrophilic domains and hydrophobic domains, which are energetically favorable due to the increase in entropy. When the film contacts water, hydrophilic domains are removed and replaced with large pores. The rate of drug release in this case is solely controlled by the porosity of the film and the resulting increased total surface area. The typical drug release curve in this case has a high, uncontrolled initial burst followed with a very slow release of residual drug afterwards.

Previously, when non-surfactant hydrophilic molecules are mixed into the polymer and then removed, a film with a porous structure is created. This porous layer reduces mechanical strength and elasticity, making it less suitable for certain applications. Additionally, this structure does not withstand heat compression bonding of the film because the pores would collapse. The loss of porous structure during heat compression negates the original intent of using the hydrophilic molecule, thus resulting in a densely packed film without any enhanced therapeutic agent release capability.

Further, if the hydrophilic molecule remains in the polymer layer during heat compression, the dissolution of the hydrophilic molecule in vivo causes the formation of very large pores, approximately 3-10 µm in diameter. Such large pores provide a large surface area, thereby causing a burst release of drug. In contrast to the use of hydrophilic molecules, the use of a surfactant as a releasing agent in the present technology enables the formation of microchannels approximately 5-20 nanometers in diameter, which is two orders of magnitude smaller than the pores resulting from the use of hydrophilic molecules. This allows tight control of the drug release by diffusion and, if desirable, without an uncontrolled burst release upon implantation. Additionally, use of a surfactant as a releasing agent allows the agent to remain present in the polymer prior to use and no pre-formed pores are created. This approach is particularly advantageous because the polymer's mechanical properties are preserved, thereby allowing the polymer to be easily processed and worked into different configurations.

In the present technology, the releasing agent is pre-mixed into the bioresorbable polymer such that each layer of polymer is contiguous and dense. The depot 100 is then formed when these layers are bonded together via heat compression without any adverse impact to the functional capabilities of the film. When the densely packed film is ultimately implanted, the releasing agent dissolves to enable efficient, controlled release of the therapeutic agent.

In some embodiments, the releasing agent comprises a polysorbate. Polysorbate is commonly used in the pharmaceutical industry as an excipient and solubilizing agent. Polysorbate is a non-ionic surfactant formed by the ethoxylation of sorbitan followed by esterification by lauric acid. Polysorbate 20 [IUPAC name: polyoxyethylene(20)sorbitan monolaurate] contains a mixture of ethoxylated sorbitan with 20 repeat units of polyethylene glycol distributed among four different sites in the sorbitan molecule. Common commercial names include Tween™ and Tween 20™ (Croda International Plc, Goole, East Yorkshire, UK) and Alkest® TW 20 (Oxiteno, Houston, TX).

Polysorbate is often utilized to improve oral bioavailability of a poorly water-soluble/hydrophobic drug. For example, polysorbate was used to improve bioavailability of active molecules that possess low solubility and/or intestinal epithelial permeability and it was observed that the bioavailability of this poorly water-soluble drug was greatly enhanced in a formulation with polysorbate or similar surfactants. (WO2008/030425; Breslin; Merck.) Akbari, et al., observed that using the hydrophilic carrier polyethylene glycol (PEG) along with polysorbate leads to faster an oral enhanced drug release rate because the polysorbate brings the drug in close contact with the PEG. (Akbari, J., et al., ADV. PHARM. BULL., 2015, 5(3): 435-41.)

Polysorbate also functions as a water-soluble emulsifier that promotes the formation of oil/water emulsions. For example, the drug famotidine is known to have high solubility in water but low in vivo permeability. Polysorbate was used in an oral microemulsion formulation for enhancing the bioavailability of famotidine. (Sajal Kumar Jha, et al., IJDDR, 2011, 3(4): 336-43.) Polysorbate is also used as a wetting agent to achieve rapid drug delivery. For example, Ball et al., achieved rapid delivery of maraviroc via a combination of a polyvinylpyrrolidone (PVP) electrospun nanofiber and 2.5 wt % Tween 20, which allowed for the complete release of 28 wt % maraviroc in just six minutes. It was believed that use of Tween 20 as a wetting agent allowed water to penetrate the PVP nanofiber matrix more quickly, thereby increasing the rate of drug release. (Ball, C., et al., ANTIMICROB. AGENTS CHEMOTHERAPY, 2014, 58:8, 4855-65.)

As described above, in order to improve drug release in certain polymer carriers, hydrophilic polymers, such as polysorbate, have been added to these carriers to accelerate or to enhance drug release from biocompatible polymers such as polyethylene glycol (PEG) in oral formulations (Akbari, J., et al., ADV. PHARM. BULL., 2015, 5(3): 435-441). However, these formulations are intended to provide an immediate release of a hydrophobic drug into a hydrophilic environment (the in vivo physiologic fluid), not a variable or sustained controlled release as part of a control region.

In some embodiments, the releasing agent is polysorbate 20, commercially known as Tween 20™. Other releasing agents suitable for use in the present technology include polysorbates, such as Polysorbate 80, Polysorbate 60, Polysorbate 40, and Polysorbate 20; sorbitan fatty acid esters, such as sorbitan monostearate (Span 60), sorbitan tristearate (Span 65), sorbitane trioleate (Span 85), sorbitan monooleate (Span 80), sorbitan monopalmitate, sorbitan monostearate, sorbitan monolaurate, sorbitan monopalmitate, sorbitan trioleate, and sorbitan tribehenate; sucrose esters, such as sucrose monodecanoate, sucrose monolaurate, sucrose distearate, and sucrose stearate; castor oils such as polyethoxylated castor oil, polyoxyl hydrogenated castor oil, polyoxyl 35 castor oil, Polyoxyl 40 Hydrogenated castor oil, Polyoxyl 40 castor oil, Cremophor® RH60, and Cremophor® RH40; polyethylene glycol ester glycerides, such as Labrasol®, Labrifil® 1944; poloxamer; polyoxyethylene polyoxypropylene 1800; polyoxyethylene fatty acid esters, such as Polyoxyl 20 Stearyl Ether, diethylene glycol octadecyl ether, glyceryl monostearate, triglycerol monostearate, Polyoxyl 20 stearate, Polyoxyl 40 stearate, polyoxyethylene sorbitan monoisostearate, polyethylene glycol 40 sorbitan diisostearate; oleic acid; sodium desoxycholate; sodium lauryl sulfate; myristic acid; stearic acid; vitamin E-TPGS (vitamin E d-alpha-tocopherol polyethylene glycol succinate); saturated polyglycolized glycerides, such as Gelucire® 44/14 and Gelucire® 50/13; and polypropoxylated stearyl alcohols such as Acconon® MC-8 and Acconon® CC-6.

Diffusion Openings

The channels or voids formed within the therapeutic region 200 and/or control region 300 by dissolution of the releasing agent may be in the form of a plurality of interconnected openings or pores and/or a plurality of interconnected pathways. In some embodiments, one or more of the channels may be in the form of discrete pathways, channels, or openings within the respective therapeutic and/or control region. Depending on the chemical and material composition of the therapeutic and control regions, one or more of the formed channels may extend: (a) from a first end within the therapeutic region to a second end also within the therapeutic region; (b) from a first end within the therapeutic region to a second end at the interface of the therapeutic region and the control region; (c) from a first end within the therapeutic region to a second end within the control region; (d) from a first end within the therapeutic region through the control region to a second end at an outer surface of the control region; (e) from a first end at the interface between the therapeutic region and the control region through the control region to a second end within the control region; (f) from a first end at the interface between the therapeutic region and the control region to a second end at an outer surface of the control region; (g) from a first end within the control region to a second end also within the control region; and (h) from a first end within the control region to a second end at an outer surface of the control region. Moreover, one or more of the channels may extend between two or more microlayers of the therapeutic region and/or control region.

F. Constituent Ratios

In some embodiments, the ratio of the polymer in the control region 300 to the releasing agent in the control region 300 is at least 1:1. In some embodiments, the ratio may be at least 1.5:1, at least 2:1, at least 2.5:1, or at least 3:1.

In some embodiments, a ratio of the mass of the therapeutic agent in the depot 100 to the polymer mass of the depot is at least 1:1, at least 2:1, at least 3:1, at least 4:1, at least 5:1, at least 6:1, at least 7:1, at least 8:1, at least 9:1, at least 10:1, at least 11:1, at least 12:1, at least 13:1, at least 14:1, at least 15:1, or at least 16:1.

In some embodiments, the ratio of releasing agent to polymer to therapeutic agent in the therapeutic region 200 is of from about 0.1:10:20 to about 2:10:20, and in some embodiments of from about 0.1:10:20 to about 1:10:20, and in some embodiments of from about 0.1:10:20 to about 0.5:10:20.

In some embodiments, the ratio of releasing agent to polymer in the control region 300 is of from about 1:2 to about 1:10. In some embodiments, one or more of the control regions may have a ratio of releasing agent to polymer of 1:2, and one or more of the other control regions may have a ratio of releasing agent to polymer of 1:10

G. Selected Depot Embodiments Including a Base Region

In some embodiments, the depot 100 may be configured to release the therapeutic agent in an omnidirectional manner. In other embodiments, the depot may include one or more base regions covering one or more portions of the therapeutic region 200 and/or control region 300, such that release of the therapeutic agent is limited to certain directions. The base region may provide structural support for the depot. The base region may comprise a low porosity, high density of bioresorbable polymer configured to provide a directional release capability to the depot. In this configuration, the substantial impermeability of this low porosity, high density polymer structure in the base region blocks or impedes the passage of agents released from the therapeutic region 200. Accordingly, the agents released from the therapeutic region 200 take a path of less resistance through the control region 300 opposite from the base region, particularly following the creation of diffusion openings in the control region 300.

Figure 16A:
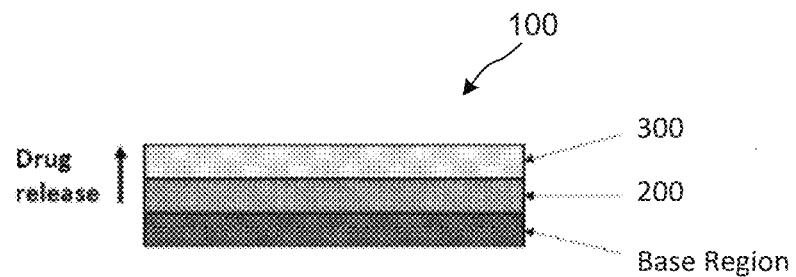
FIGS. 16A-16E depict various depot embodiments including a base region and/or a delayed release region in accordance with the technology.

An example a depot 100 of the present technology having a base region is shown in FIG. 16A. The base region may comprise a low porosity, high density of bioresorbable polymer configured to provide a directional release capability to the multi-region depot. In this configuration, the low porosity, high density polymer structure in the base region blocks or impedes passage of agents release from the therapeutic region 200. Accordingly, the agents released from the therapeutic region 200 take a path of lesser resistance through the control region opposite from the base region, particularly following the creation of channels in the control region. In an additional embodiment, the porosity of other regions of the multi-region depot can be varied to facilitate the release of therapeutic agent. For example, in this embodiment, the base region, the therapeutic region 200, and the control region 300 of the multi-region depot depicted in FIG. 16A may have different porosities ranging from low porosity in the base region to higher porosities in the therapeutic agent and control regions to facilitate the release of therapeutic agent from the multi-region depot. In additional embodiments, the porosities of the edges of the multi-region depot, or within portions of any of the individual regions, can be varied to properly regulate or manipulate the release of therapeutic agent.

Figure 16B:
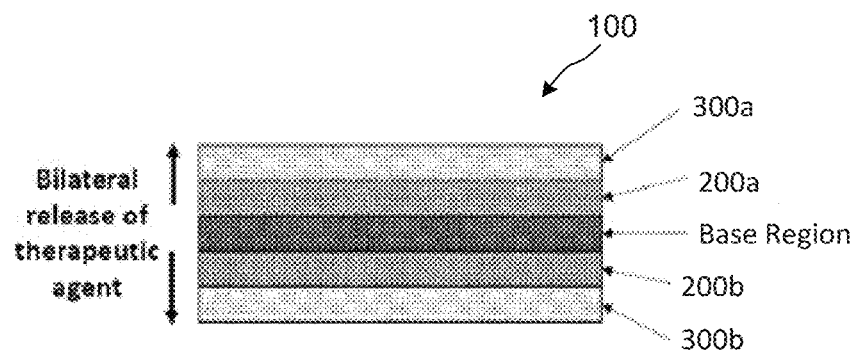
Figure 16C:
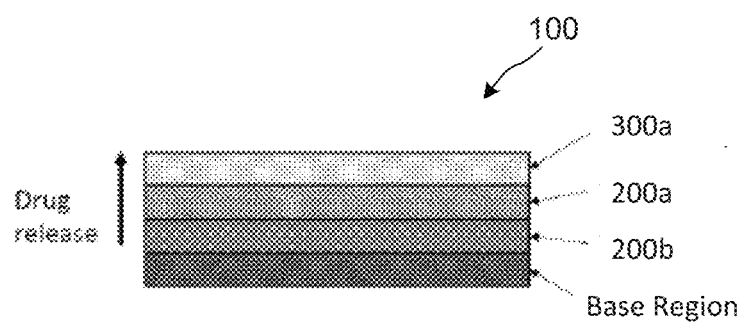

In the embodiment depicted in FIG. 16B, the multi-region depot provides for a bilateral or bidirectional release of therapeutic agent. This bidirectional release capability is accomplished through symmetric regioning about a high density base region, wherein, as described above, the therapeutic agent releases along a path of less resistance, thereby releasing away from the high density base region. More specifically, disposed on one side of the base region is a control region 300a and a therapeutic region 200a and, disposed on the other side of the base region, is a control region 300b and a therapeutic region 200b that are substantially similar to the pair on the other side. These pairs on either side of the base region are configured to produce substantially equivalent, bidirectional release of therapeutic agent. In an alternate embodiment, a bidirectional release that is not equivalent (i.e., the therapeutic agent and/or rate of release in each direction is not the same) may be accomplished by asymmetric regioning, whereby the control region and therapeutic region pairs on either side of the base region are substantially different.

In additional embodiments, it may be desirable for the multi-region depot to release multiple therapeutic agents. This capability can be particularly useful when multimodal pharmacological therapy is indicated. In the embodiment shown in FIG. 16C, the multi-region depot comprises a topmost or outermost control region 300a, a first therapeutic region 200a adjacent to the control region, a second therapeutic region 200b adjacent to the first therapeutic region 200a, and a base region adjacent to the second therapeutic region 200b. In this embodiment, the first therapeutic region 200a and the second therapeutic region 200b comprise a first therapeutic agent and a second therapeutic agent, respectively. In certain embodiments, the first and second therapeutic agents are different. In one embodiment, the multi-region depot is configured to release the first and second therapeutic agents in sequence, simultaneously, or in an overlapping fashion to yield a complementary or synergistic benefit. In this configuration, the presence and function of the control region 300a may also ensure consistent and, if desired, substantially even release of multiple therapeutic agents residing beneath. Since many conventional drug delivery devices can fail to provide an even release of multiple drugs with different molecular weights, solubility, etc., the role of the control region in achieving a substantially even release of different therapeutic agents can be a significant advantage.

In some embodiments, the first therapeutic agent and second therapeutic agent are the same therapeutic agent but are present in the first and second therapeutic regions, respectively, in different relative concentrations to represent different dosages to be administered. In some embodiments, the first and second therapeutic agents of the first and second therapeutic regions, respectively, may have no clinical association or relationship whatsoever. For example, in an embodiment for use as part of a total joint replacement (e.g., total knee arthroplasty, total hip arthroplasty) or other surgical procedure, it may be clinically desirable to administer in the vicinity of the surgical site both an analgesic (e.g., local anesthetic) to treat and better manage postoperative pain for several days or weeks following the surgery and an antibiotic to treat or prevent surgical site infection associated with the surgery or implanted prosthesis (if any) for several weeks or months following the surgery. In this embodiment, the first therapeutic region 200a may comprise a therapeutically effective dose of local anesthetic to substantially provide pain relief for no less than 3 days and up to 15 days following the surgery and the second therapeutic region 200b may comprise a therapeutically effective dose of antibiotics to substantially provide a minimally effective concentration of antibiotic in the vicinity of the surgical site for up to three months following the surgery.

Figure 16D:
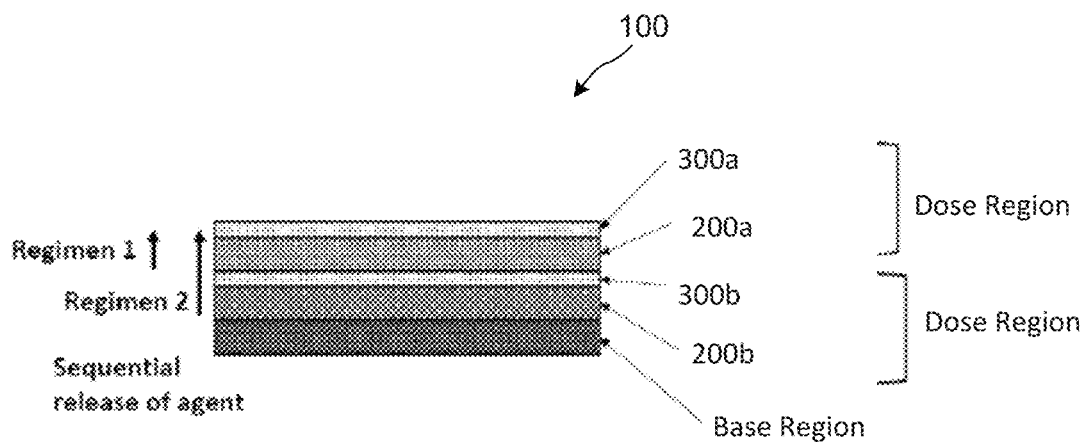

In some embodiments, as shown in FIG. 16D, the depot 100 comprises a first dosage region and a second dosage region, wherein the first and second dosage regions correspond to first and second dosage regimens. More specifically, each dosage region comprises a control region and therapeutic region pair, wherein each pair is configured for controlled release of a therapeutic agent from the therapeutic region 200a, 200b in accordance with a predetermined dosage regimen. For example, in treating and/or managing postoperative pain, it may be desirable for the multi-region depot to consistently release 50-400 mg/day of local anesthetic (e.g., bupivacaine, ropivacaine and the like) for at least 2-3 days following surgery (i.e., first dosage regimen) and then release a local anesthetic at a slower rate (e.g., 25-200 mg/day) for the next 5 to 10 days (i.e., second dosage regimen). In this exemplary embodiment, the first dosage region, and the control region and therapeutic region pair therein, would be sized, dimensioned, and configured such that the multi-region depot releases the first therapeutic agent in a manner that is consistent with the prescribed first dosage regimen. Similarly, the second dosage region, and the control region and therapeutic region pair therein, would be sized, dimensioned and configured such that the multi-region depot releases the second therapeutic agent in a manner that is consistent with the prescribed second dosage regimen. In another embodiment, the first and second dosage regions may correspond to dosage regimens utilizing different therapeutic agents. In one embodiment, the multi-region depot 100 is configured to administer the first and second dosage regimens in sequence, simultaneously, or in an overlapping fashion to yield a complementary or synergistic benefit. In an alternate embodiment of this scenario, the first and second dosage regimens, respectively, may have no clinical association or relationship whatsoever. For example, as described above with respect to the embodiment depicted in FIG. 16C, the first dosage regimen administered via the first dosage region may be treating or managing postoperative pain management and the second dosage regimen administered via the second dosage region may be treating or preventing infection of the surgical site or implanted prosthesis (if any).

Figure 16E:
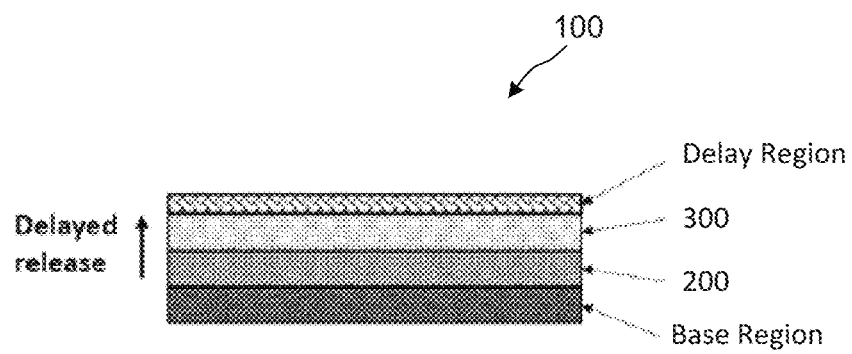

Certain embodiments of the present invention utilize delayed release agents. As illustrated in FIG. 16E, the depot 100 may include a delay region as the outermost (i.e., topmost) region to the multi-region depot and adjacent to a control region 300 comprising a releasing agent. The delay region presents a barrier to physiologic fluids from reaching and dissolving the releasing agent within the control region. In one embodiment, the delay region may comprise a delayed release agent mixed with a bioresorbable polymer, but without a releasing agent. Delayed release agents are different from the releasing agents used in the multi-region depot of the invention. Delayed release agents dissolve in physiological fluids more slowly than do releasing agents and thus provide the possibility for release of a therapeutic agent a defined amount of time following implantation of the multi-region depot. In embodiments where a delayed release agent is not present in the delay region, it may take more time for the physiological fluids to traverse the delay region and contact the releasing agent. Only when the physiological fluids make contact with the control region will the releasing agent begin to dissolve, thus allowing the controlled release of the therapeutic agent. Delayed release agents may be advantageously used in the therapeutic methods of the invention wherein the therapeutic agent is not immediately required. For example, a nerve blocking agent may be injected prior to a surgical procedure, numbing the entire area around a surgical site. The controlled release of a local anesthetic is not required in such a surgery until the nerve block wears off.

Suitable delayed release agents for use in the present invention are pharmaceutically acceptable hydrophobic molecules such as fatty acid esters. Such esters include, but are not limited to, esters of myristoleic acid, sapienic acid, vaccenic acid, stearic acid, arachidic acid, palmitic acid, erucic acid, oleic acid, arachidonic acid, linoleic acid, linoelaidic acid, eicosapentaenoic acid, docosahexaenoic acid. Preferred esters include stearic acid methyl ester, oleic acid ethyl ester, and oleic acid methyl ester. Other suitable delayed release agents include tocopherol and esters of tocopherol, such as tocopheryl nicotinate and tocopheryl linolate.

H. Example Methods of Manufacture

The depots of the present technology may be constructed using various combinations of biodegradable, bioresorbable polymer layers, wherein these layers may include therapeutic agents, releasing agents, delay release agents, etc., in varying combinations and concentrations in order to meet the requirements of the intended clinical application(s). In some embodiments, the polymer layers may be constructed using any number of known techniques to form a multilayer film of a particular construction. For example, a bioresorbable polymer and a therapeutic agent can be solubilized and then applied to the film via spray coating, dip coating, solvent casting, and the like. In an alternative embodiment, a polymer layer for use as a control layer and/or a therapeutic agent layer can be constructed from electrospun nanofibers.

The depots 100 described herein may be constructed by placing therapeutic regions (and/or sub-regions) and/or control regions (and/or sub-regions) on top of one another in a desired order and heat compressing the resulting multilayer configuration to bond the layers together. Heat compression may be accomplished using any suitable apparatus known in the art. In one embodiment, the heat compression process consists of utilizing a heat compressor (Kun Shan Rebig Hydraulic Equipment Co. Ltd., China), and heat compressing the stacked assembly of therapeutic 200 and/or control regions 300 at a temperature that is above room temperature (e.g., at least 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., or 120° C., etc.) and a pressure of from about 0.01 MPa to about 1.0 MPa, or about 0.10 MPa to about 0.8 MPa, or about 0.2 MPa to about 0.6 MPa. The inventors have discovered that heating the therapeutic and control regions during compression (separately or after stacking) increases the therapeutic agent density in the depot 100. The inventors have also discovered that heat compression at lower pressures enable higher drug densities.

Depending on the therapeutic dosage needs, anatomical targets, etc., the depot 100 can be processed, shaped and otherwise engineered to produce form factors that can be administered to the patient by implantation in the body by a clinical practitioner. For example, various configurations of the film may be achieved by using a jig with a pre-shaped cutout, hand cutting the desired shape or both. Some of the form factors producible from the multilayer film for implantation into the body include: strips, ribbons, hooks, rods, tubes, patches, corkscrew-formed ribbons, partial or full rings, nails, screws, tacks, rivets, threads, tapes, woven forms, t-shaped anchors, staples, discs, pillows, balloons, braids, tapered forms, wedge forms, chisel forms, castellated forms, stent structures, suture buttresses, coil springs, and sponges. The depot 100 may also be processed into a component of the form factors mentioned above. For example, the depot 100 could be rolled and incorporated into tubes, screws tacks or the like. In the case of woven embodiments, the depot 100 may be incorporated into a multi-layer woven film wherein some of the filaments used are not the inventive device. In one example, the depot 100 is interwoven with Dacron, polyethylene or the like.

III. EXAMPLES

The following examples are offered by way of illustration and not by way of limitation.

Example 1

Preparation of bioresorbable polymer drug films. Two depots of the present technology containing a high payload the local anesthetic bupivacaine were prepared according to the following procedures.

Each of the sample depots consisted of a heat compressed, multi-layer film having the configuration shown in FIG. 5. The therapeutic region consisted of a single layer and was sandwiched between two inner control layers (closest to the therapeutic layer, such as 302b and 302c in FIG. 5, and referred to as "Control Layer A" in Table 4 below) and two outer control layers (farthest from therapeutic region, such as 302a and 302d in FIG. 5, and referred to as "Control Layer B" in Table 4). The constituents of the therapeutic region and the control region are detailed in Table 4.

TABLE 4

| Therapeutic Region | Single layer |
| --- | --- |
| Polymer | Poly(L-lactide-co-glycolic-co-ε-caprolactone) (1760 mg) (Durect Corp, Birmingham) PLA to PGA to PCL ratio of from 90:5:5 to 60:30:10 |
| Releasing Agent | Tween 20 (860 mg) (Sigma-Aldrich Pte Ltd; Singapore) |
| Anesthetic | bupivacaine hydrochloride (3520 mg) (Xi'an Victory Biochemical Technology Co., Ltd.; Shaanxi, People's Republic of China) |
| Anesthetic:Polymer | 2:1 |
| Releasing Agent:Polymer:Anesthetic | 5:10:20 |
| Control Region | |
| Control Layer A | innermost layer on top and bottom |
| Polymer | PLGACL (1056 mg) |
| Releasing Agent | Tween 20 (517 mg) |
| Control Layer B | outermost layer on top and bottom |
| Polymer | PLGACL (1056 mg) |
| Releasing Agent | Tween 20 (103 mg) |

Therapeutic region components. The therapeutic region was prepared by combining the polymer, releasing agent, anesthetic, and 3.15 mg of acetone (Merck; Kenilworth, NJ) in a glass vial and mixing thoroughly. The resulting blend was poured onto a flat plate and compressed multiple times to form a thick film (about 1 mm thick) upon drying.

Control region components. The control region was prepared by combining the polymer, releasing agent, and 4.7 mg of acetone (Merck; Kenilworth, NJ) in a glass vial and mixing thoroughly. The resulting blend was poured onto a flat plate and drawn by a film applicator to form a thin film (<200 μm thickness) upon drying.

For the sample depot, the single layer therapeutic region and the four layers comprising the control region were aligned and compressed by a heat compressor. The thin film was cut to form a 25 mm×15 mm sample with overall film thickness <1.2 mm.

in vitro drug release testing of bupivacaine depot. The purpose of this procedure was to measure the release of bupivacaine from a bioresorbable polymer depot into a receiving fluid of 1×PBS. Each release experiment was conducted in duplicate. The in vitro release procedure consisted of placing a known size of film into an apparatus containing the receiving fluid. The in vitro release apparatus consisted of a 200 mL glass bottle. A receiving fluid in the amount of 100 mL was added to each sample bottle. During the release study, the apparatus was placed in a water bath maintained at 37±2° C. At predetermined intervals, samples of the receiving fluid were removed and analyzed for bupivacaine concentration by UV-Visible Spectrophotometer.

Figure 20:
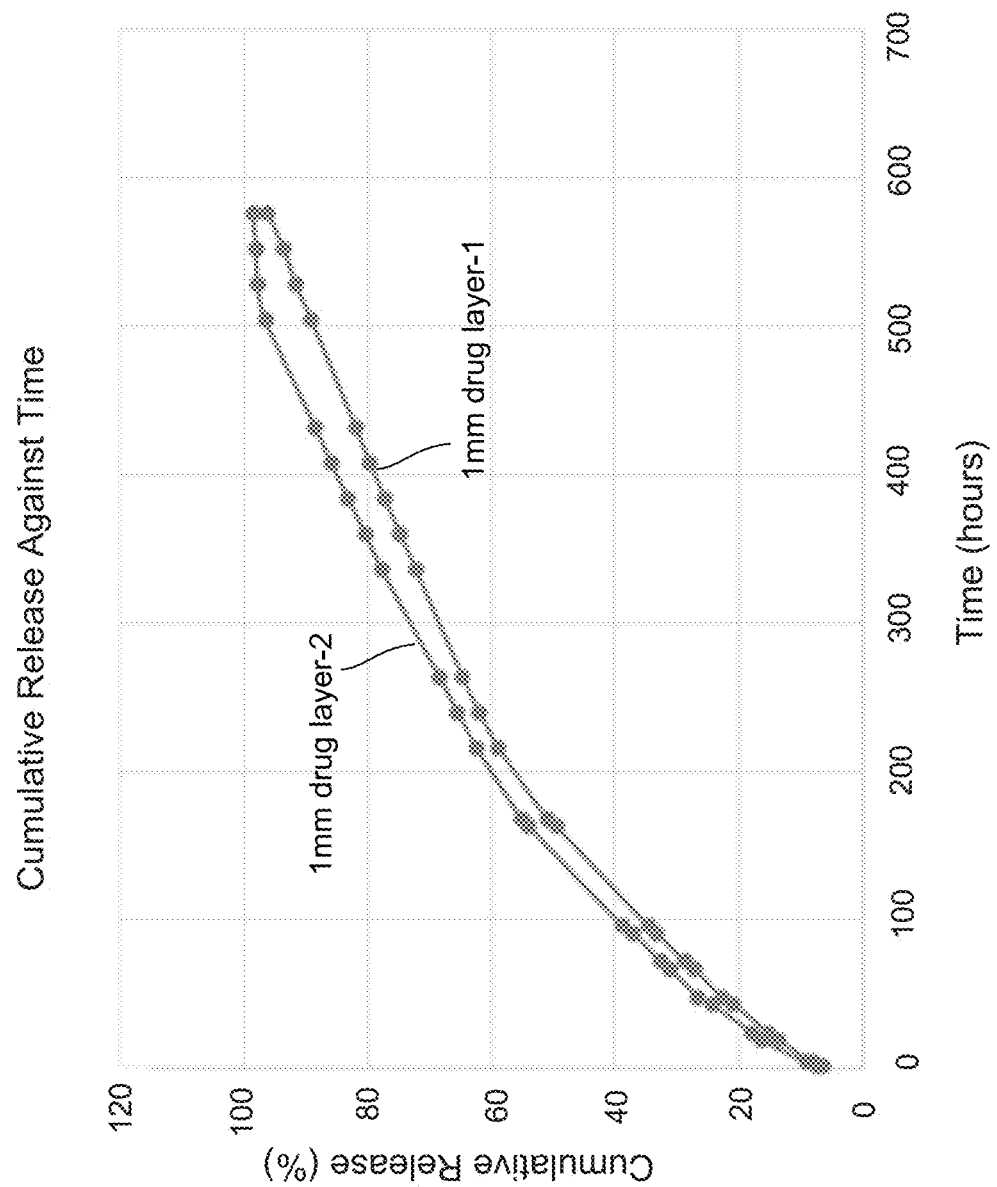
FIG. 20 depicts the in vitro release profile for the depots as described in Example 1, in accordance with the present technology.

FIG. 20 shows the drug release profile for the depots with effectively reduced initial burst effect and demonstrated a desirable consistent controlled release of drug.

Example 2A

Preparation of bioresorbable polymer drug films. Two depots of the present technology comprising the local anesthetic bupivacaine were prepared as described in Example 1, except the depots of the present example comprised two of the depots of Example 1 stacked on top of one another and heat compressed to form a new, thicker sample having an overall film thickness of about 2 mm (for example, see the configuration shown in FIG. 6).

in vitro drug release testing of bupivacaine depot. in vitro drug release testing of the depots was performed as described in Example 1.

Figure 21:
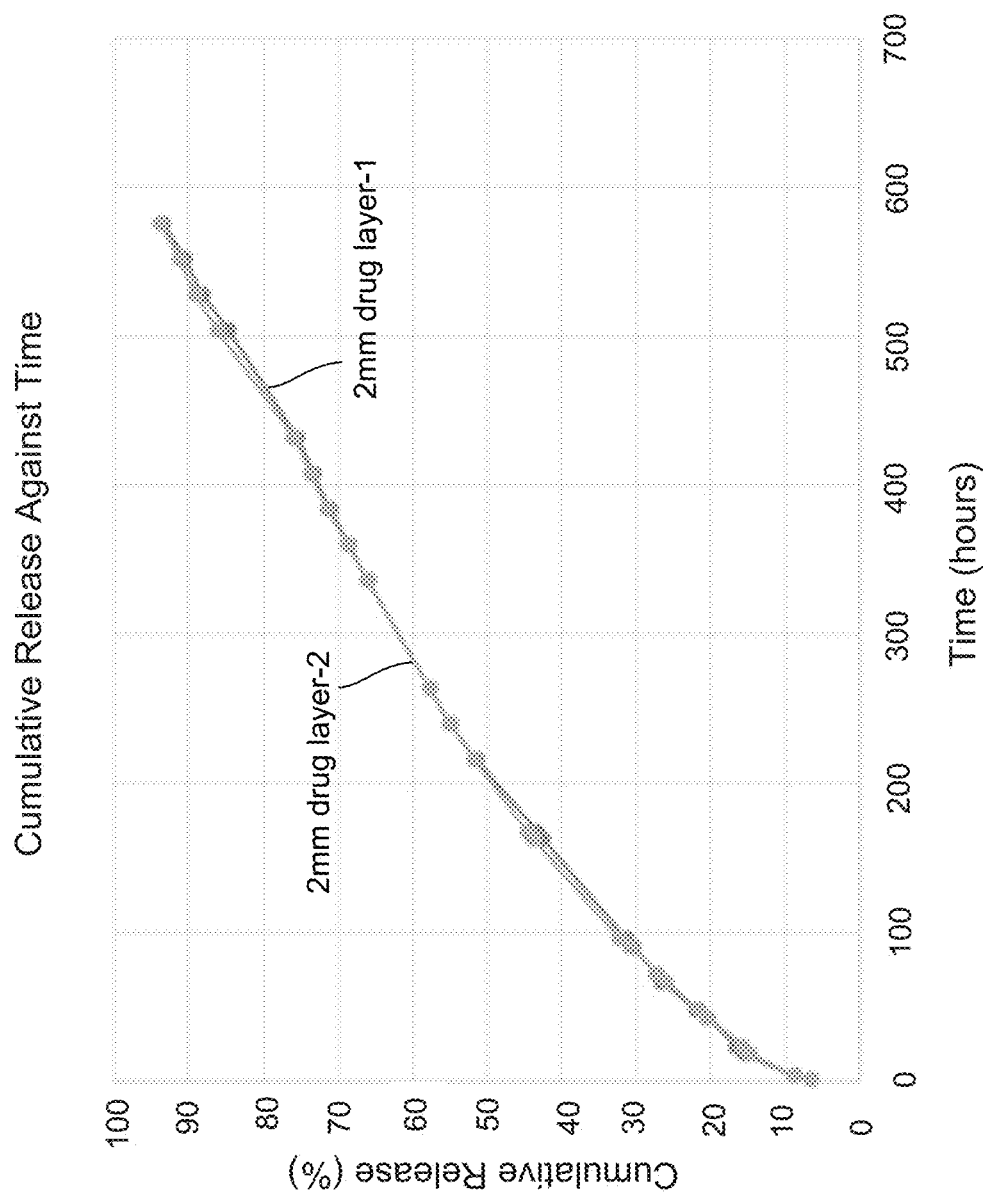
FIG. 21 depicts the in vitro release profile for the depots as described in Example 2A, in accordance with the present technology.

Release profiles. FIG. 21 shows the average cumulative dose profiles of the bupivacaine films. The graph shows controlled release of over 500 hours with the initial 24-hour release of about 20%.

Example 2B

Preparation of bioresorbable polymer drug films. Two depots of the present technology comprising the local anesthetic bupivacaine were prepared as described in Example 1, except the depots of the present example comprised three of the depots of Example 1 stacked on top of one another and heat compressed to form a new, thicker sample having an overall film thickness of about 3 mm (for example, see the configuration shown in FIG. 7).

In vitro drug release testing of bupivacaine depot. in vitro drug release testing of the depots was performed as described in Example 1.

Figure 22:
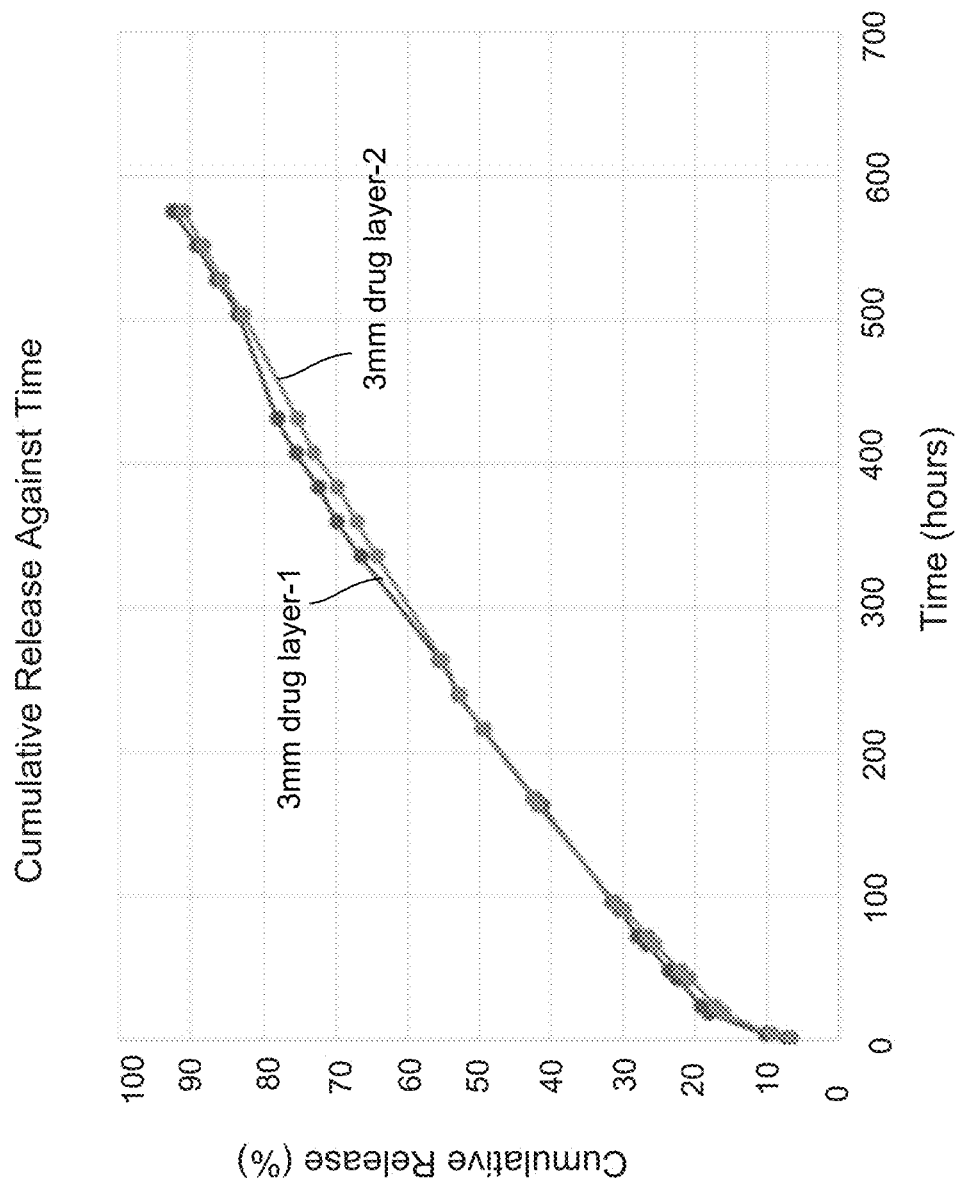
FIG. 22 depicts the in vitro release profile for the depots as described in Example 2B, in accordance with the present technology.

Release profiles. FIG. 22 shows the average cumulative dose profiles of the bupivacaine films. The graph shows controlled release of over 500 hours with the initial 24-hour release of about 20%.

Example 3

Preparation of bioresorbable polymer/drug films. Four depots of the present technology comprising the local anesthetic bupivacaine were prepared as described below.

Each of the sample depots consisted of a heat compressed, multi-layer film formed of an inner depot similar to that shown in FIG. 5 encapsulated by a different control region (described below). The inner depot of each sample depot consisted of a therapeutic region (formed of 10 heat-compressed therapeutic layers) sandwiched between two inner control layers (closest to the therapeutic region, such as 302b and 302c in FIG. 5, and referred to as Control Layer A in Table 5 below) and two outer control layers (farthest from therapeutic region, such as 302a and 302d in FIG. 5), and referred to as Control Layer B in Table 5). The constituents of the therapeutic region and the control region are detailed in Table 5.

TABLE 5

| Therapeutic Region | 10 heat-compressed microlayers |
|---|---|
| Polymer | Poly(L-lactide-co-ε-caprolactone)(PLCL) (Corbion; Lenexa, KS) having a PLA to PCL ratio of from 90:10 to 60:40 (880 mg) |
| Releasing Agent | Tween 20 (440 mg) (Sigma-Aldrich Pte Ltd; Singapore) |
| Anesthetic | bupivacaine hydrochloride (1760 mg) (Xi'an Victory Biochemical Technology Co., Ltd.; Shaanxi, People's Republic of China) |
| | DCM 13.33 g |
| Anesthetic:Polymer | 2:1 |
| | Control Region |
| Control Layer A | |
| Polymer | PLCL (352 mg) |
| Releasing Agent | Tween 20 (172 mg) |
| DCM | 5.3 g |
| Control Layer B | |
| Polymer | PLCL (352 mg) |
| Releasing Agent | Tween 20 (35 mg) |
| DCM | 5.3 g |

Therapeutic region. The therapeutic region constituents (see Table 5 above) were added to a glass vial and mixed thoroughly. The resulting blend was poured onto a flat plate and drawn by a film applicator to form a thin film upon drying (<200 μm thickness).

Control region. The control region constituents (see Table 5 above) were added to a glass vial and mixed thoroughly. The resulting blend was poured onto a flat plate and drawn by a film applicator to form a thin film upon drying (<200 μm thickness).

For each sample film, 10 drug layers (each initially <200 μm thickness) and 4 control layers were aligned (Control B-Control A-10 therapeutic layers-Control A-Control B) and compressed by a heat compressor (Kun Shan Rebig Hydraulic Equipment Co. Ltd.; People's Republic of China). The resulting thin film was cut to form a 20 mm×20 mm triangle sample with an overall film thickness of <0.2 mm. The triangle samples were further aligned, and fully encapsulated, with (a) a Control Layer A on both sides (i.e., two additional control layers), (b) a Control Layer B on both sides (i.e., two additional control layers), (c) two of Control Layer A on both sides (i.e., four additional control layers), (d) two of Control Layer B on both sides (i.e., four additional control layers). The resulting assembly was then compressed by a heat compressor (Kun Shan Rebig Hydraulic Equipment Co. Ltd.; People's Republic of China).

in vitro drug release testing of bupivacaine depot. The purpose of this procedure was to measure the release of bupivacaine, from a bioresorbable polymer depot into a receiving fluid of 1×PBS. Each release experiment was conducted in duplicate. The in vitro release procedure consisted of placing a known size of film into an apparatus containing the receiving fluid. The in vitro release apparatus consisted of either a 20 mL or a 100 mL glass bottle. A receiving fluid in the amount of 12 mL or 50 mL was added to each sample bottle. During the release study, the apparatus was placed in a water bath maintained at 37±2° C. At predetermined intervals, samples of the receiving fluid were removed and analyzed for bupivacaine concentration by a UV-Visible Spectrophotometer.

Figure 23:
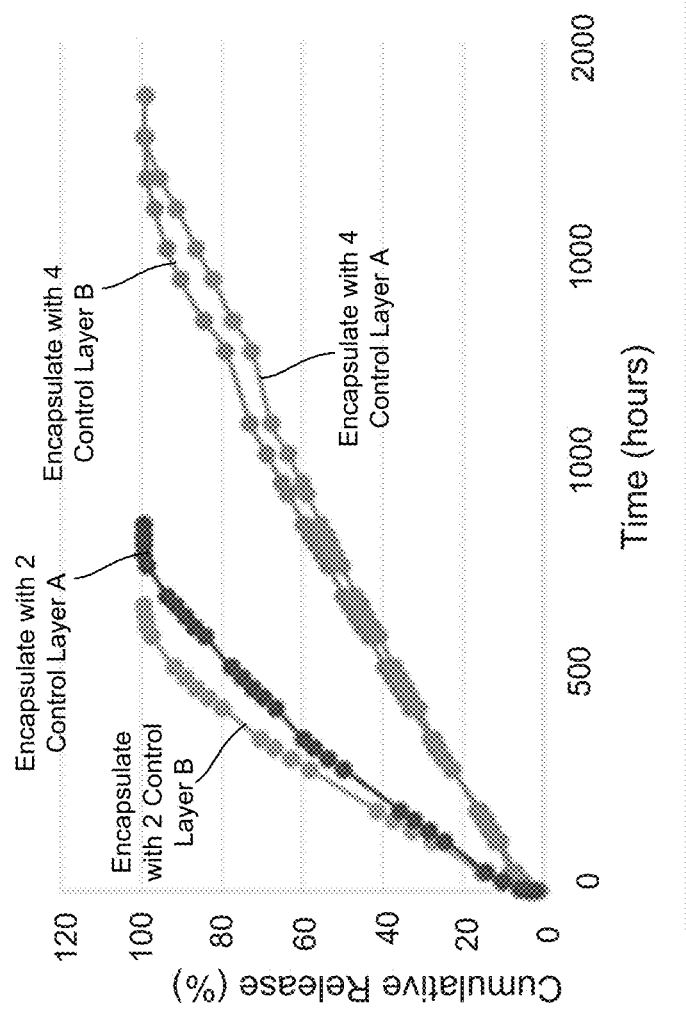
FIG. 23 depicts the in vitro release profile for the depots as described in Example 3, in accordance with the present technology.

Release profiles. FIG. 23 shows the average cumulative dose profiles of the bupivacaine films. The graph shows controlled release of over 1500 hours for some of the configurations.

Example 4

Sample depots of the present technology were implanted subcutaneously in living rabbits (one depot per rabbit). The depots were placed in a subcutaneous pocket.

Each of the sample depots consisted of a heat compressed, multi-layer film having the configuration shown in FIG. 5. The therapeutic region consisted of a single layer and was sandwiched between two inner control layers (closest to the therapeutic layer, such as 302*b* and 302*c* in FIG. 5) and two outer control layers (farthest from therapeutic region, such as 302*a* and 302*d* in FIG. 5).

The present example tested two groups of depots, each utilizing a different polymer. The depots in Group A included Poly (DL-lactide-glycolide-F-caprolactone) in a molar ratio of 60:30:10, and the depots in Group B included Poly (DL-lactide-co-glycolide) in a molar ratio of 50:50. Each group included a depot having a low, medium, or high dose of bupivacaine HCl.

For the depots of Group A, each inner control layer consisted of 3.9 mg, 4.0 mg, or 4.7 mg of the polymer (for Low, Med, and High dose groups, respectively) and 1.9 mg, 2.0 mg, or 2.3 mg of a releasing agent (polysorbate 20) (for Low, Med, and High dose groups, respectively). Each outer control layer consisted of 5.3 mg, 5.5 mg, or 6.3 mg of the polymer (for Low, Med, and High dose groups, respectively) and 1.9 mg, 2.0 mg, or 2.3 mg of a releasing agent (polysorbate 20) (for Low, Med, and High dose groups, respectively).

For the depots of Group A, the therapeutic region consisted of 71.5 mg, 152.6 mg, or 269 mg of the polymer (for Low, Med, and High dose groups, respectively), 34.9 mg, 74.6 mg, or 131.5 mg of a releasing agent (polysorbate 20) (for Low, Med, and High dose groups, respectively), and 142.9 mg, 305.2 mg, or 538.1 mg of a local anesthetic (bupivacaine HCl).

For the depots of Group B, each inner control layer consisted of 4.7 mg, 5.1 mg, or 5.3 mg of the polymer (for Low, Med, and High dose groups, respectively) and 2.3 mg, 2.5 mg, or 2.6 mg of a releasing agent (polysorbate 20) (for Low, Med, and High dose groups, respectively). Each outer control layer consisted of 6.4 mg, 6.9 mg, or 7.3 mg of the polymer (for Low, Med, and High dose groups, respectively), and 0.6 mg, 0.7 mg, or 0.7 mg of a releasing agent (polysorbate 20) (for Low, Med, and High dose groups, respectively).

For the depots of Group B, the therapeutic region consisted of 87.0 mg, 171.1 mg, or 317.7 mg of the polymer (for Low, Med, and High dose groups, respectively), 42.5 mg, 83.6 mg, or 155.2 mg of a releasing agent (polysorbate 20) (for Low, Med, and High dose groups, respectively), and 173.9 mg, 342.2 mg, or 635.4 mg of a local anesthetic (bupivacaine HCl).

Within each of Group A and Group B, the low dose depots were about 20 mm×20 mm×<1 mm (e.g., 0.89 mm and 0.9 mm), the medium dose depots were about 20 mm×20 mm×<2 mm (e.g., 1.8 mm and 1.6 mm), and the high dose depots were about 20 mm×20 mm×<3 mm (e.g., about 2.7 mm and about 2.8 mm).

Blood draws for bupivacaine concentration analysis were collected through Day 28.

Group A

Figure 24A:
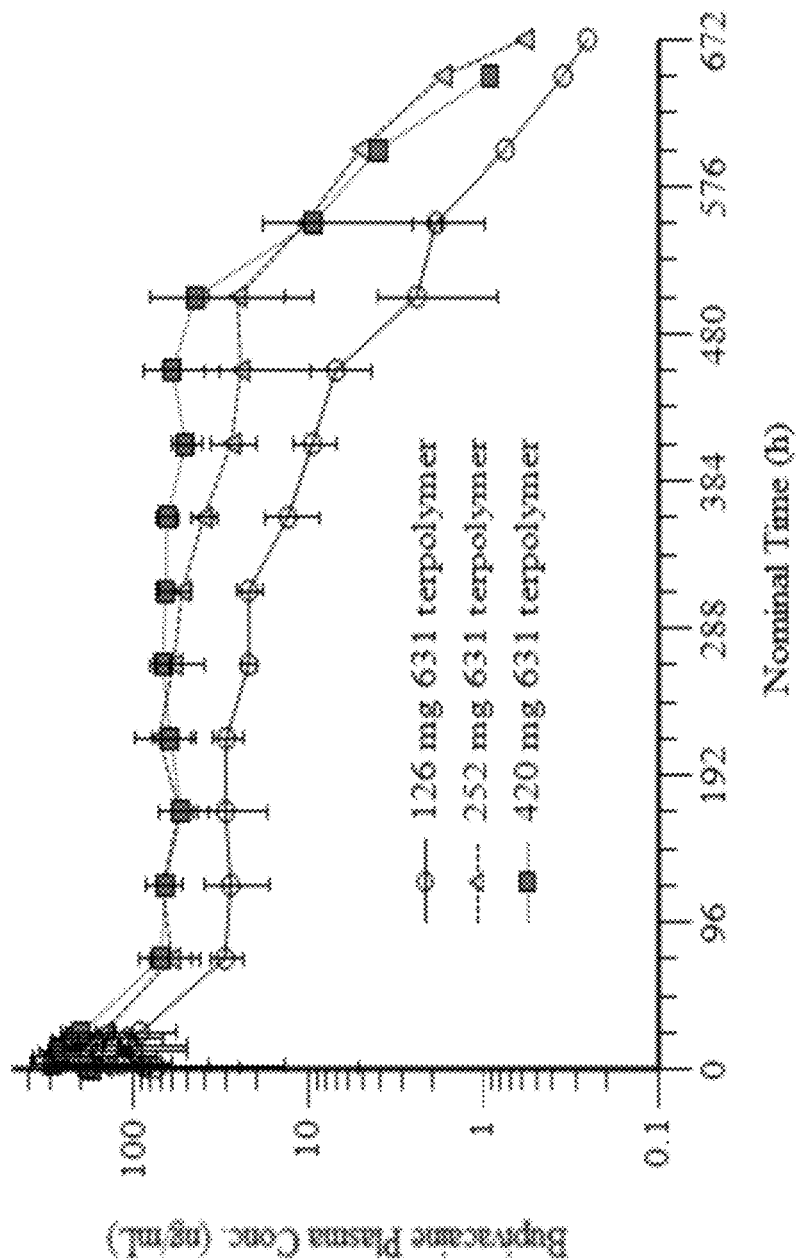
FIG. 24A shows the in vivo blood plasma bupivacaine concentration over time for a rabbit implanted with the depots as described in Example 4, in accordance with the present technology.

The Group A depots were administered to 3 rabbits/dose group and PK samples were collected to day 28. The semi-log plot of the group mean data for each dose is shown in FIG. 24A. The product, regardless of dose, exhibits peak exposure within the first 72 hours and then a plateau of exposure that is determined by the dose (the higher the dose the longer the plateau) followed by more rapid terminal clearance. The release of bupivacaine is rapid with a consistent similar profile for each rabbit with moderate variability over the first 72 hours.

Figure 24B:
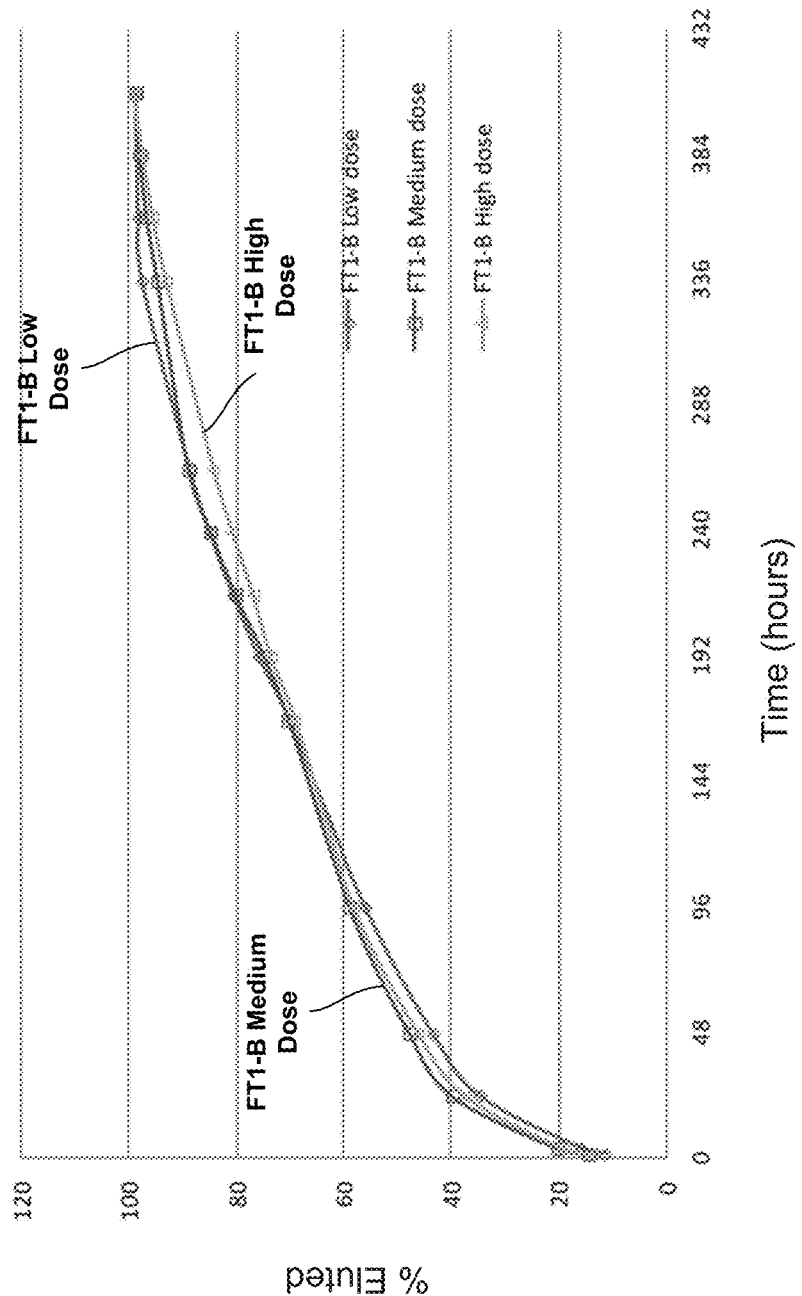
FIG. 24B depicts the in vitro release profile over time for the sample depots as described in Example 4, in accordance with the present technology.

The in vitro pharmacokinetic ("PK") profile for Group A is shown in FIG. 24B. The half-life of the initial distribution phase through the first 72-96 hours was generally consistent through the three dose strengths (implant sizes) and $T_{max}$ occurred within the first 24 hours for all rabbits, with a median $T_{max}$ between 4-8 hours. The peak exposure ($C_{max}$) for the high dose exhibited a low CV % of 17.6%. This data would indicate a controlled initial rapid release of bupivacaine during the period of greatest discomfort post TKA surgery. The exposure profile was stable from 72 hours through at least 436 hours. The terminal phase half-life started to exhibit the more innate half-life of bupivacaine, particularly in the high dose where the terminal phase $t_{1/2}$ was 17.4 hours. This would suggest that the depot had almost completely released the drug by Day 21.

The high dose, Group A depot was consistent in average exposure from Day 3 to Day 18, while the mid and low dose depots were consistent from Day 3 to Day 14. There was not a significant difference in exposure between the Mid and High dose groups from Day 3-14, while the Low dose was approximately half the exposure level during this time period.

Group B

Figure 24C:
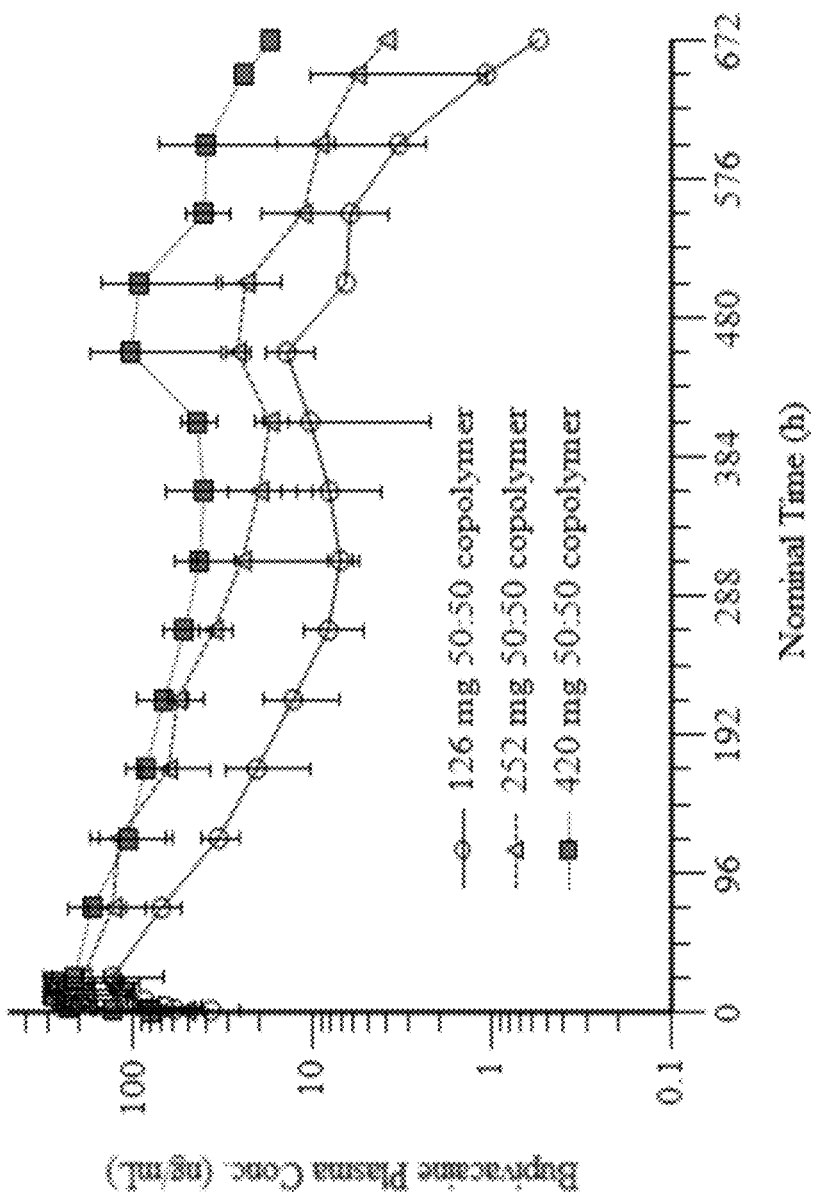
FIG. 24C shows the in vivo blood plasma bupivacaine concentration over time for a rabbit implanted with the depots as described in Example 4, in accordance with the present technology.

Formulation 50:50 copolymer was administered to 3 rabbits/dose group and PK samples were collected to hour 672 (Day 28). The semi-log plot of the group mean data for each dose is presented in FIG. 24C. The product, regardless of dose, exhibits peak exposure within the first 72 hours and then a gradual decline in exposure followed by a secondary faster release coupled with a secondary peak in exposure at approximately Day 19-21. After the secondary peak, bupivacaine exposure declined with different rates dependent on dose (lower the dose the faster the clearance). FIG. 24C highlights the group mean (SD) and individual rabbits for Low Dose (126 mg) in Panel A, Mid Dose (252 mg) in Panel B and High Dose (420 mg) in Panel C through the first 96 hours. The release of bupivacaine is rapid with a consistent and similar profile for each rabbit with moderate variability over the first 72 hours.

Figure 24D:
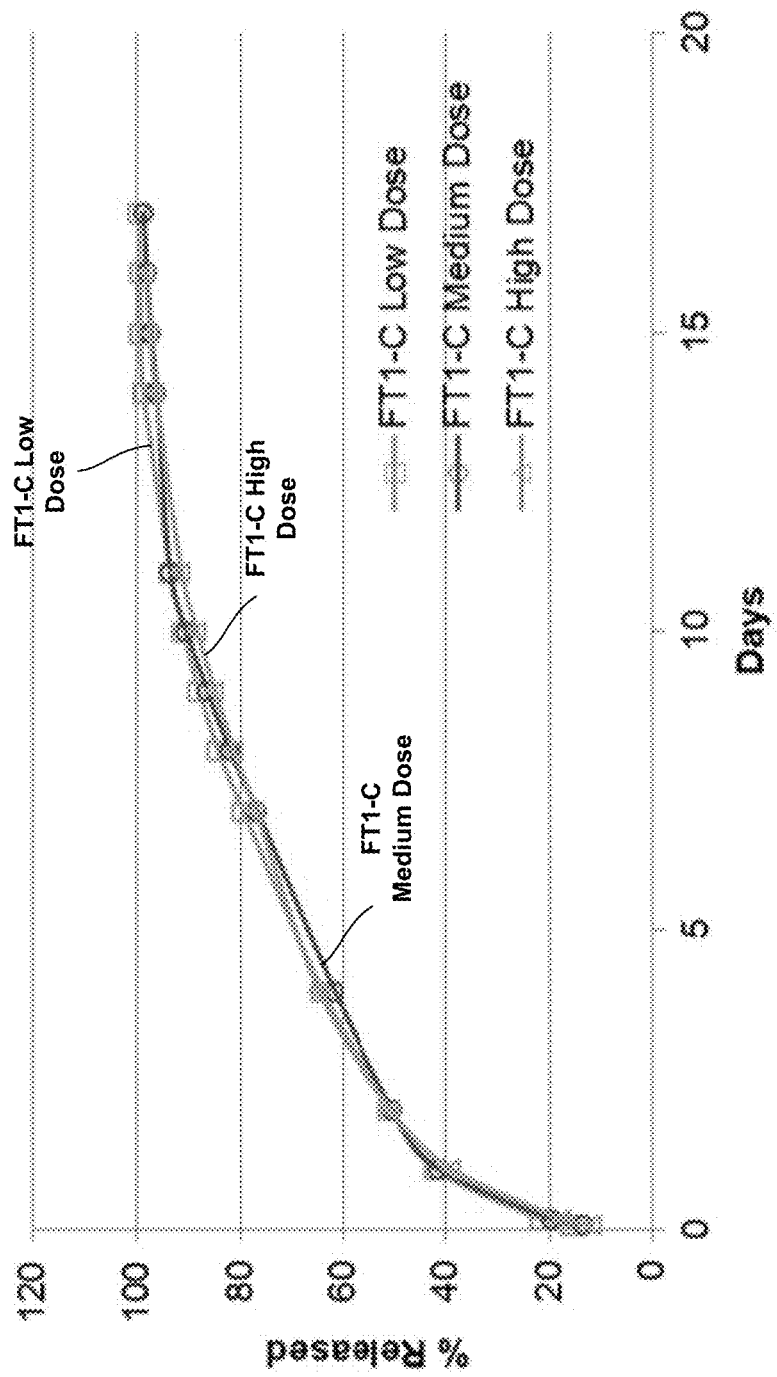
FIG. 24D depicts the in vitro release profile over time of the sample depots as described in Example 4, in accordance with the present technology.

The in vitro pharmacokinetic profile is shown in FIG. 24D. The 50:50 copolymer did not exhibit an initial distribution half-life like the 631 terpolymer, however $T_{max}$ occurred within the first 24 h for all rabbits, with a median $T_{max}$ that was slightly further out in time, between 16-20 hours. The peak exposure ($C_{max}$) exhibited a very low CV % of 5.99%. This data would indicate a controlled initial rapid release of bupivacaine during the acute postoperative pain period (i.e., period of greatest discomfort post TKA surgery) followed by a more gradual decline in release rate through the subacute postoperative pain period, which is consistent with the presumed steady decline in pain during that same period. This release profile having the steady decline in release rate during the acute postoperative pain period is in contrast with the release rate of the 631 polymer formulation, where the release rate states substantially constant throughout the postoperative pain period.

All three dose levels slowly decreased exposure over the Day 3 to Day 18 time period.

Example 5

Two sample depots of the present technology were implanted in the intraarticular space of a knee joint of a living canine. The surgeon performed a medial and lateral parapatellar arthrotomy to insert one sample depot in the medial gutter and one sample depot in the lateral gutter. The depots were anchored in place by 4-0 PDS II suture. Two canines were the subject of the present study.

Each of the sample depots consisted of a heat compressed, multi-layer film having the configuration shown in FIG. 5. The therapeutic region consisted of a single layer and was sandwiched between two inner control layers (closest to the therapeutic layer, such as 302b and 302c in FIG. 5) and two outer control layers (farthest from therapeutic region, such as 302a and 302d in FIG. 5). Each inner control layer consisted of 5.7 mg of a bioresorbable polymer (60:30:10 terpolymer Poly (DL-lactide-glycolide-F-caprolactone)) and 2.8 mg of a releasing agent (polysorbate 20). Each outer control layer consisted of 7.7 mg of a bioresorbable polymer (60:30:10 terpolymer Poly (DL-lactide-glycolide-F-caprolactone)) and 0.8 mg of a releasing agent (polysorbate 20).

The therapeutic region comprised a single layer consisting of 118 mg of a bioresorbable polymer (60:30:10 terpolymer Poly (DL-lactide-glycolide-F-caprolactone)), 57.6 mg of a releasing agent (polysorbate 20), and 235.9 mg of a local anesthetic (bupivacaine HCl).

Each of the depots was about 15 mm×about 25 mm×about 1 mm.

Following implantation, the canines were evaluated at predetermined intervals to determine the post-operative pharmacokinetic (PK) profile of bupivacaine in synovial fluid and blood plasma. For PK values of bupivacaine in the blood plasma (i.e., representing systemic bupivacaine levels), blood was drawn at scheduled intervals after implantation of the depots. The PK results for the plasma fluid samples are shown at FIG. 25.

Figure 25:
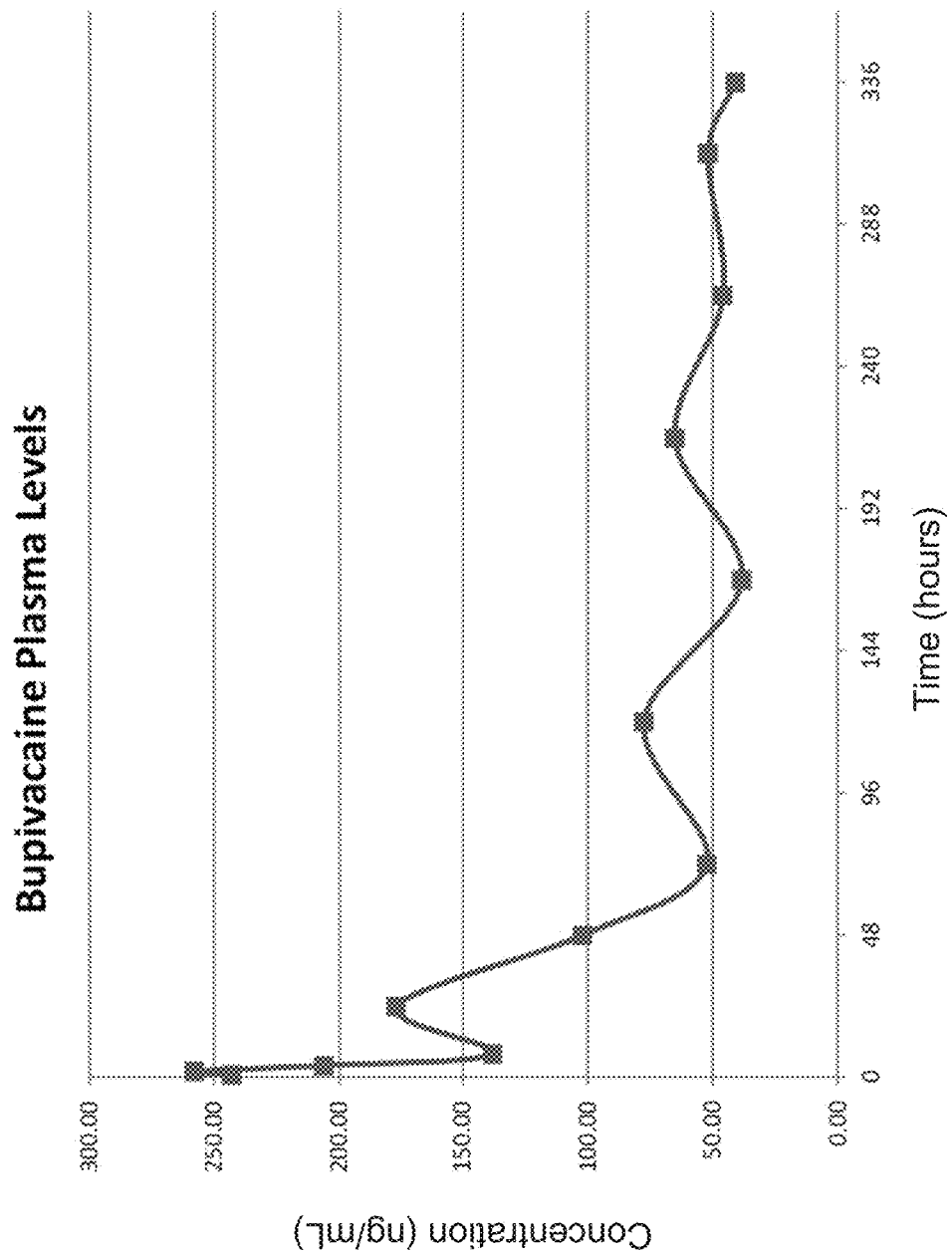
FIG. 25 shows the in vivo blood plasma bupivacaine concentration over time for a canine implanted with the depots as described in Example 5, in accordance with the present technology.

As shown in FIG. 25, the depot 100 released an initial, controlled burst over about the first three days, followed by a tapering release for the remaining 11 days.

Example 6

Three sample depots of the present technology were implanted in the intraarticular space of a knee joint of a living sheep. The surgeon performed a medial and lateral parapatellar arthrotomy to insert one sample depot in the medial gutter and two sample depots in the lateral gutter. The lateral gutter depots were sutured side-by-side prior to implantation to keep the depots in place relative to each other in the gutter. The depots were then anchored in place to the capsular tissue by 4-0 PDS II suture.

Each of the sample depots consisted of a heat compressed, multi-layer film having the configuration shown in FIG. 5. The therapeutic region consisted of a single layer and was sandwiched between two inner control layers (closest to the therapeutic layer, such as 302b and 302c in FIG. 5) and two outer control layers (farthest from therapeutic region, such as 302a and 302d in FIG. 5). Each inner control layer consisted of 5.3 mg of a bioresorbable polymer (Poly (DL-lactide-co-glycolide) in a molar ratio of 50:50)) and 2.6 mg of a releasing agent (polysorbate 20). Each outer control layer consisted of 7.2 mg of a bioresorbable polymer (Poly (DL-lactide-co-glycolide) in a molar ratio of 50:50)) and 0.7 mg of a releasing agent (polysorbate 20).

The therapeutic region comprised a single layer consisting of 118.1 mg of a bioresorbable polymer (Poly (DL-lactide-co-glycolide) in a molar ratio of 50:50), 57.7 mg of a releasing agent (polysorbate 20), and 236.3 mg of a local anesthetic (bupivacaine HCl).

Each of the depots was about 15 mm×about 25 mm×about 1 mm.

Following implantation, the sheep was evaluated at 1, 4, 8, 15, and 30 days to determine the post-operative pharmacokinetic (PK) profile of bupivacaine in synovial fluid and blood plasma.

Figure 26A:
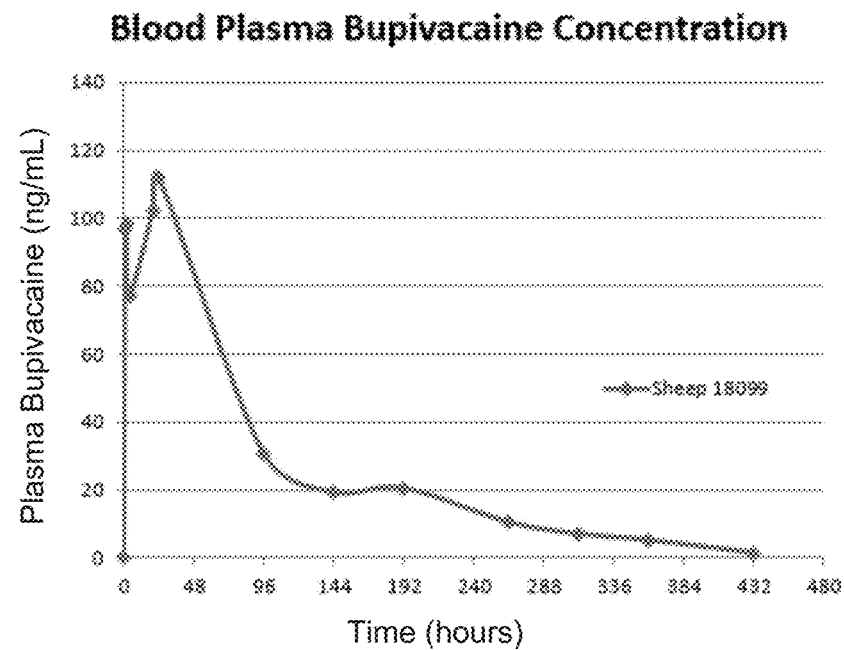
FIG. 26A shows the in vivo blood plasma bupivacaine concentration over time for a sheep implanted with the depots as described in Example 6, in accordance with the present technology.

For PK values of bupivacaine in the blood plasma (i.e., representing systemic bupivacaine levels), 1 mL of blood was drawn 1, 2, 4, 8, 12, 16, 20, 24 and 48 hours after implantation of the depots, then every 48 hours (at the same time as was drawn on previous days, +/−1 hr) in all animals until day 28 prior to sacrifice. The PK results for the plasma fluid samples are shown in FIG. 26A. As shown, the systemic plasma bupivacaine concentration showed an initial, controlled burst over the first 2-4 days, followed by a tapering release for the remaining period.

Figure 26B:
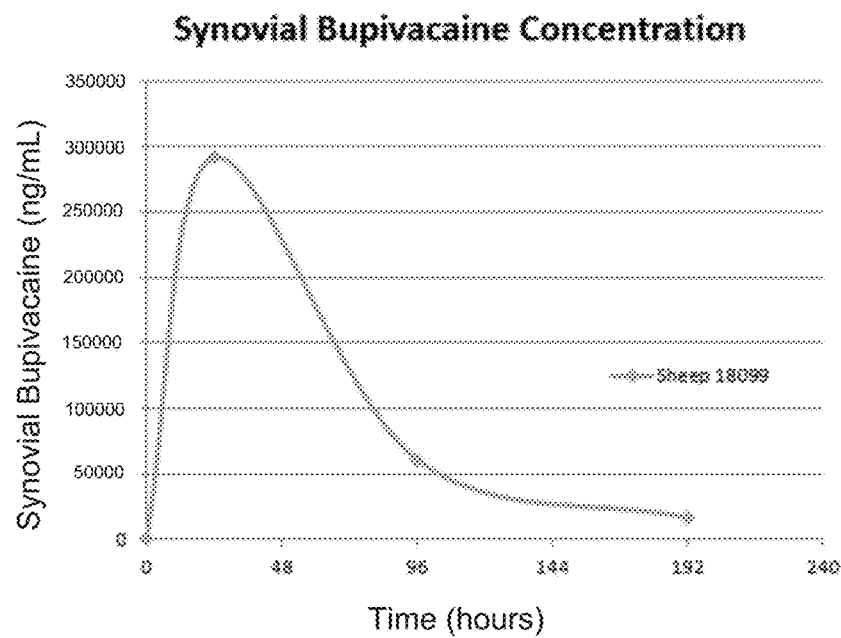
FIG. 26B shows the in vivo synovial bupivacaine concentration over time for a sheep implanted with the depots as described in Example 6, in accordance with the present technology.

For PK values of bupivacaine in the synovial fluid (i.e., representing local bupivacaine levels), a minimum of 0.5 mL of synovial fluid was aspirated from the joint at 0 hours (i.e., just prior to surgery), 24 hours, 96 hours, and 192 hours. The PK results for the synovial fluid samples are shown in FIG. 26B. As shown, the local synovial concentration showed an initial, controlled burst over the first 2-4 days, followed by a tapering release for the remaining period.

Figure 26C:
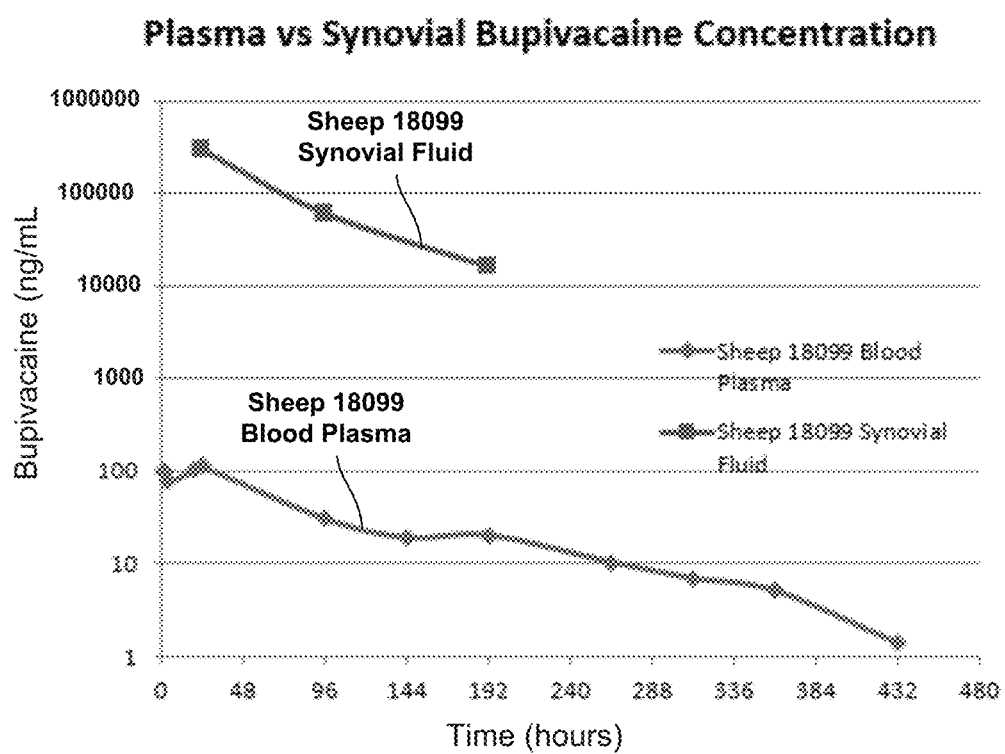
FIG. 26C is a plot depicting the blood plasma bupivacaine concentration versus the synovial bupivacaine concentration over time for a sheep implanted with the depots as described in Example 6, in accordance with the present technology.

FIG. 26C is a plot depicting the blood plasma bupivacaine concentration versus the synovial bupivacaine concentration over time. As demonstrated in FIG. 26C, the PK values are illustrative of a release profile achieved in prior in vitro and in vivo studies, wherein the initial, controlled burst over the first 2-4 days provides a substantial dosage of bupivacaine during the acute postoperative pain period and the tapering release that follows provides a therapeutic dosage during the subacute postoperative pain period. As shown, local bupivacaine levels were an order of magnitude greater than systemic bupivacaine levels. Achieving a high local concentration of bupivacaine without correspondingly high systemic levels allows for optimized analgesia without the risk of systemic toxicity.

IV. SELECTED SYSTEMS AND METHODS FOR TREATING POSTOPERATIVE PAIN ASSOCIATED WITH ORTHOPEDIC SURGERY

The depots 100 of the present technology may be used to treat a variety of orthopedic injuries or diseases depending upon the nature of the therapeutic agent delivered as described above. The therapeutic agent may be delivered to specific areas of the patient's body depending upon the medical condition being treated. The depots 100 of the present technology may be positioned in vivo proximate to the target tissue (i.e., bone, soft tissue, etc.) in the patient's body to provide a controlled, sustained release of a therapeutic agent for the treatment of a particular condition. This implantation may be associated with a surgery or intervention for acutely treating the particular condition, whereby the depot enables chronic, sustained pharmacological treatment following completion of the surgery or intervention. The depot may be a standalone element, or may be coupled to or integrated as part of an implantable device or prosthesis associated with the intervention or surgery.

The amount of the therapeutic agent that will be effective in a patient in need thereof will depend on the specific nature of the condition, and can be determined by standard clinical techniques known in the art. In addition, in vitro or in vivo assays may optionally be employed to help identify optimal dosage ranges. The specific dose level for any particular individual will depend upon a variety of factors including the activity of the drug, the age, body weight, general physical and mental health, genetic factors, environmental influences, sex, diet, time of administration, location of administration, rate of excretion, and the severity of the particular problem being treated.

Some aspects of the present technology include a system comprising a plurality of depots (each of which could be any of the depots described herein) provided for implantation by a clinical practitioner. In this system, each depot may be configured for controlled release of therapeutic agent to tissue proximate to the implantation site of the depot. The depots in the system may be identical or may vary in several respects (e.g., form factor, therapeutic agent, release profile, etc.). For example, the system may be comprised of a depot having a release profile that provides for an immediate release of therapeutic agent and other depots comprised of a depot having a release profile that provides for a delayed release of therapeutic agent.

Many depots of the present technology are configured to be implanted at a surgical site to treat postoperative pain at or near the site. As used herein, the term "pain" includes nociception and the sensation of pain, both of which can be assessed objectively and subjectively, using pain scores and other methods well-known in the art, such as opioid usage. In various embodiments, pain may include allodynia (e.g., increased response to a normally non-noxious stimulus) or hyperalgesia (e.g., increased response to a normally noxious or unpleasant stimulus), which can in turn be thermal or mechanical (tactile) in nature. In some embodiments, pain is characterized by thermal sensitivity, mechanical sensitivity and/or resting pain. In other embodiments, pain comprises mechanically-induced pain or resting pain. In still other embodiments, the pain comprises resting pain. The pain can be primary or secondary pain, as is well-known in the art. Exemplary types of pain reducible, preventable or treatable by the methods and compositions disclosed herein include, without limitation, include post-operative pain, for example, from the back in the lumbar regions (lower back pain) or cervical region (neck pain), leg pain, radicular pain (experienced in the lower back and leg from lumbar surgery in the neck and arm from cervical surgery), or abdominal pain from abdominal surgery, and neuropathic pain of the arm, neck, back, lower back, leg, and related pain distributions resulting from disk or spine surgery. Neuropathic pain may include pain arising from surgery to the nerve root, dorsal root ganglion, or peripheral nerve.

In various embodiments, the pain results from "post-surgical pain" or "post-operative pain" or "surgery-induced pain", which are used herein interchangeably, and refer to pain arising in the recovery period of seconds, minutes, hours, days or weeks following a surgical procedure (e.g., hernia repair, orthopedic or spine surgery, etc.). Surgical procedures include any procedure that penetrates beneath the skin and causes pain and/or inflammation to the patient. Surgical procedure also includes arthroscopic surgery, an excision of a mass, spinal fusion, thoracic, cervical, or lumbar surgery, pelvic surgery or a combination thereof.

Figure 27A:
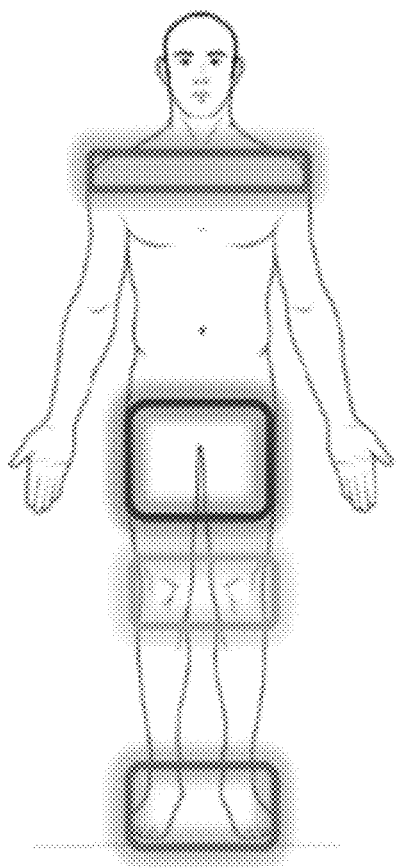
FIGS. 27A and 27B illustrate common locations within a patient that may be sites where surgery is conducted and locations where the depot can be administered.
Figure 27B:
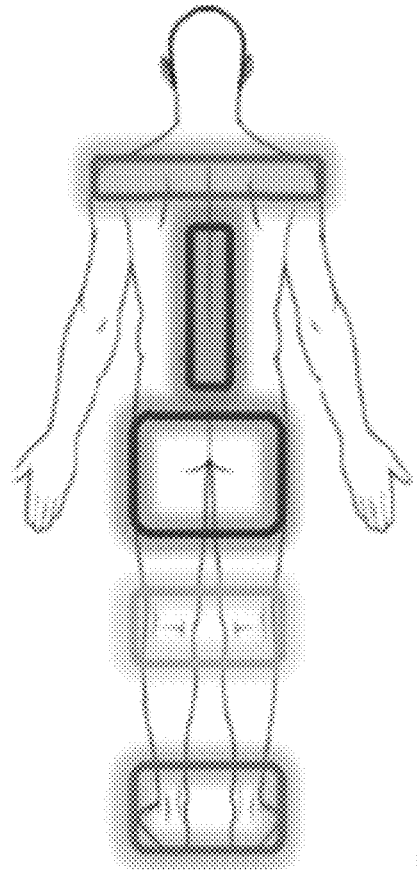

FIGS. 27A and 27B illustrate common locations within a patient that may be sites where surgery is conducted and locations where the depots of the present technology can be administered. It will be recognized that the locations illustrated in FIGS. 27A and 27B are merely exemplary of the many different locations within a patient where a surgery may take place. For example, surgery may be required at a patient's knees, hips, upper extremities, lower extremities, neck, spine, shoulders, abdomen and pelvic region. FIGS. 28A-28C illustrate a table showing common surgical procedures for which the depots 100 of the present technology may be utilized for treating postoperative pain.

Many embodiments of the present technology include one or more depots, having the same or different configuration and/or dosing, that are configured to be positioned at or near a surgical site of a knee joint to treat pain associated with a total knee replacement surgery. As previously described, the depots of the present technology may be solid, self-supporting, flexible thin films that is structurally capable of being handled by a clinician during the normal course of a surgery without breaking into multiple pieces and/or losing its general shape. This way, the clinician may position one or more of the depots at various locations at or near the intracapsular and/or extracapsular space of the knee joint, as necessary to address a particular patient's needs and/or to target particular nerves innervating the knee.

FIGS. 29A-29C, for example, are front, lateral, and medial views of a human knee, showing the location of the nerves innervating the extra- and intracapsular portion of a knee joint. In some embodiments, the depots may be implanted adjacent to one or more nerves (such as the nerves shown in FIGS. 29A-29C) innervating the knee.

Figure 30A:
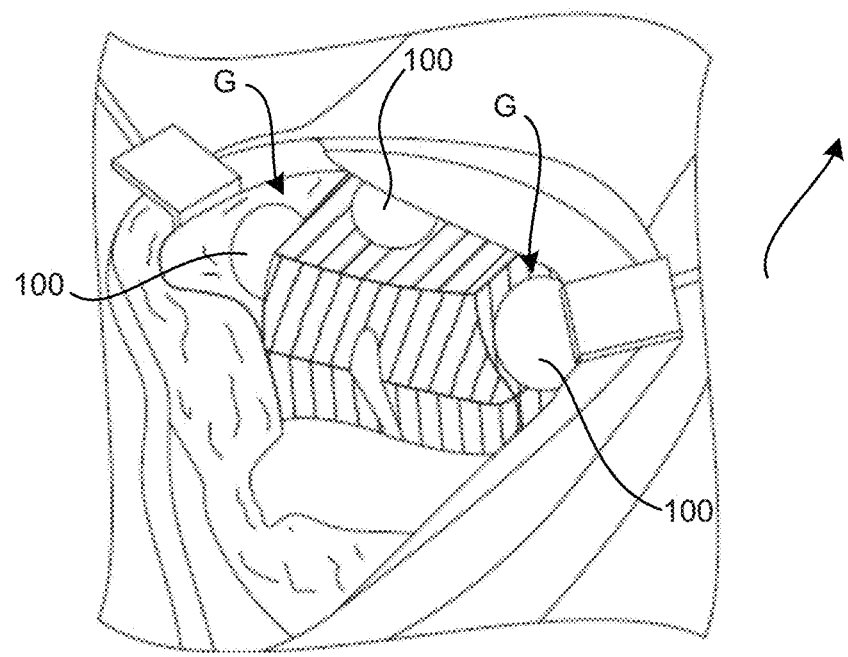
FIG. 30A is a splayed view of a human knee exposing the intracapsular space and identifying potential locations for positioning one or more depots.
Figure 30B:
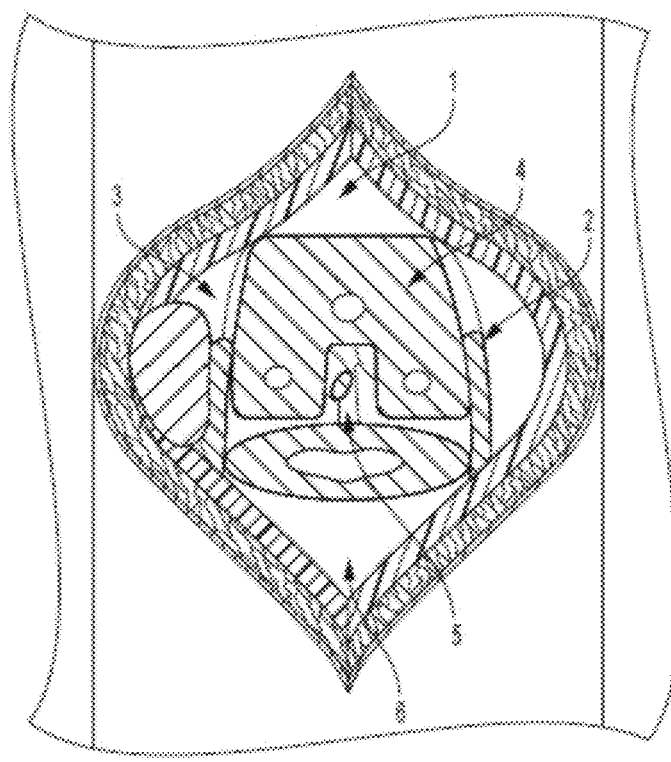
FIG. 30B is a splayed view of a human knee exposing the intracapsular space and showing several depots positioned within for treating postoperative pain.

In some instances, it may be beneficial to position one or more of the depots within the joint capsule. For example, FIG. 30A is a splayed view of a human knee exposing the intracapsular space and identifying potential locations for positioning one or more depots, and FIG. 30B is a splayed view of a human knee exposing the intracapsular space and showing several depots 100 positioned within for treating postoperative pain. As shown in FIGS. 30A and 30B, in some instances, one or more depots may be positioned at or near the suprapatellar pouch SPP, specifically under the periosteum and attached to the quadriceps tendon. Additional areas for placement of one or more depots 100 may include generally the medial and lateral gutters MG, LG (including optional fixation to tissue at the medial or lateral side of the respective gutter), on the femur F, on the tibia T (e.g., posterior attachment to the tibial plateau, at or near the anterior tibia to anesthetize infrapatellar branches of the saphenous nerve). In some embodiments, one or more depots may be positioned adjacent to at least one of a posterior capsule PC of the knee, a superior region of the patella P, and/or the arthrotomy incision into the knee capsule. In some embodiments, one or more depots 100 may be positioned at or near the saphenous nerve, the adductor canal, and/or the femoral nerve. In some embodiments, one or more of the depots may be configured to be positioned at or near an infrapatellar branch of the saphenous nerve, one or more genicular nerves of the knee, a superior region of the patella P. It may be desirable to position the depot within the knee capsule but away from any articulating portions of the knee joint itself.

Figure 31A:
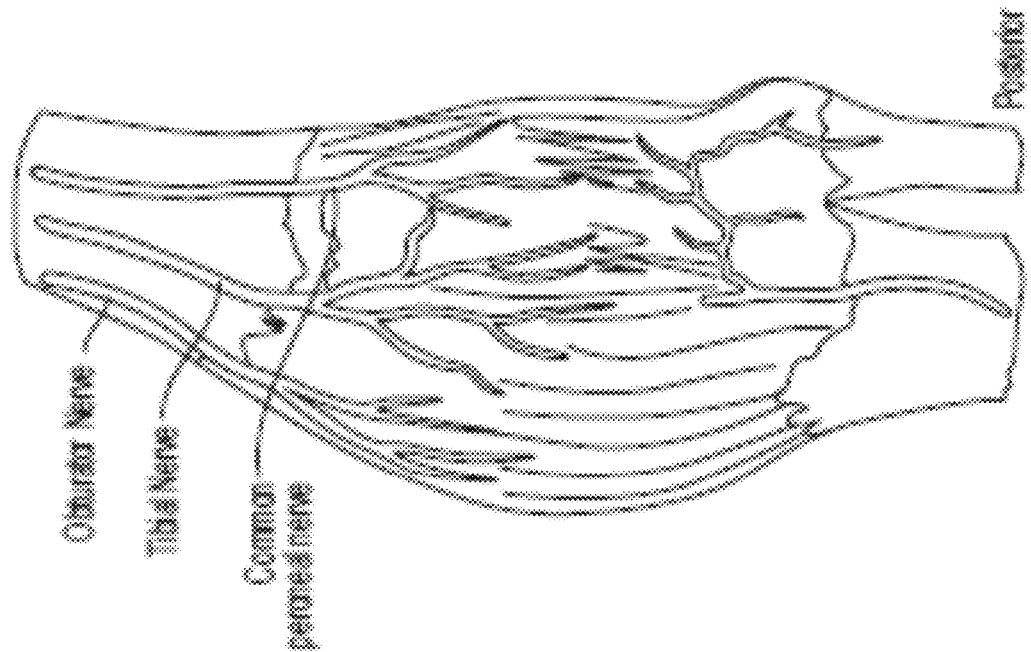
FIGS. 31A and 31B show anterior and posterior, extracapsular views of a human knee, showing the location of the nerves innervating the knee at an extracapsular location.
Figure 31B:
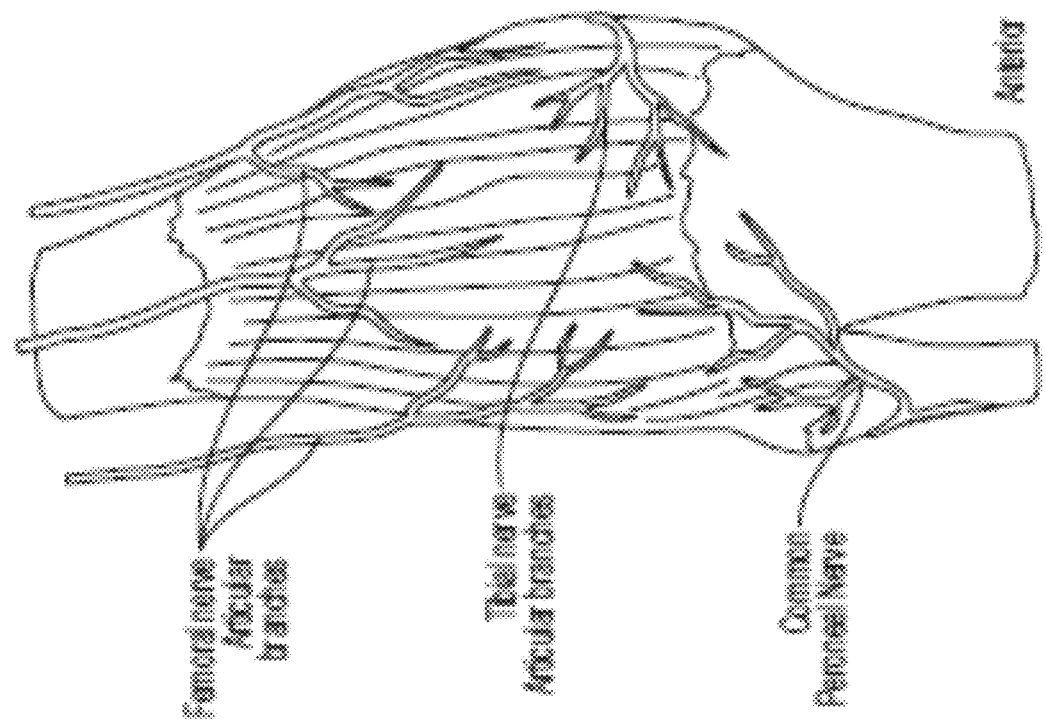
Figure 32:
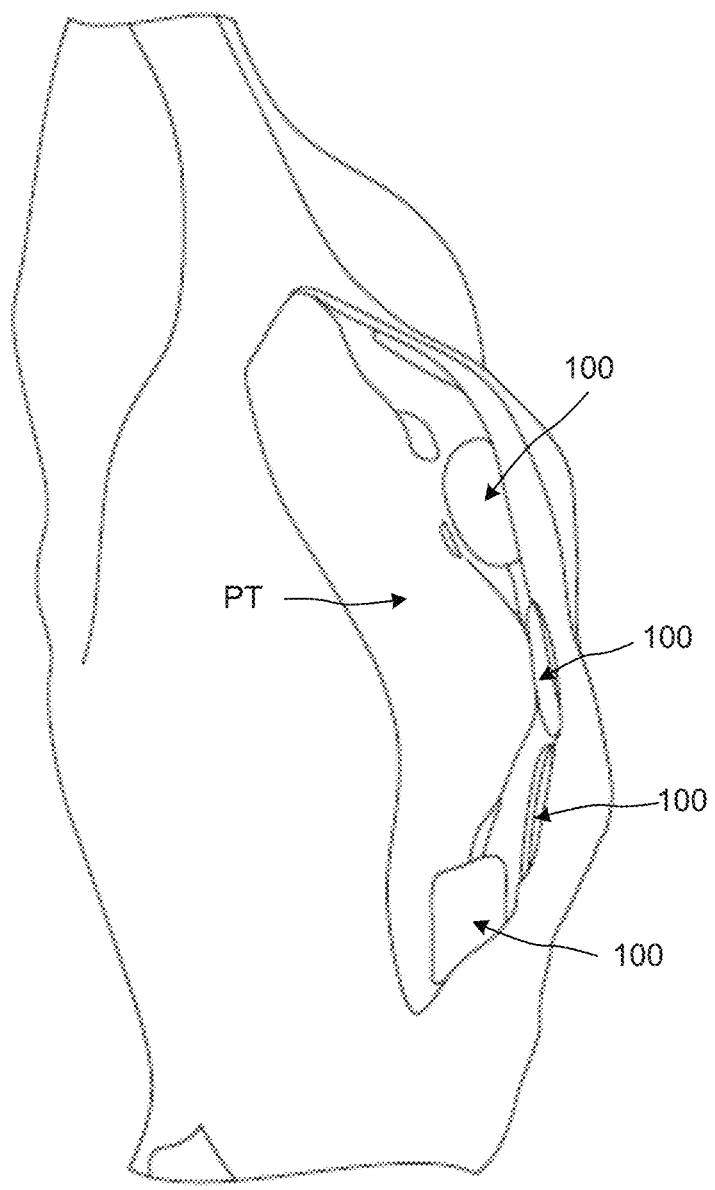
FIG. 32 is an anterior view of a partially-splayed human knee, showing an extracapsular space and showing several depots of the present technology positioned at the extracapsular space for treating postoperative pain.

Instead of or in addition to the placement of depots within the intracapsular space, one or more depots may be placed at an extracapsular position. FIGS. 31A and 31B, for example, show anterior and posterior views, respectively, of the nerves as positioned at an extracapsular location. In some embodiments, the depots may be implanted adjacent to one or more extracapsular nerves (such as the nerves shown in FIGS. 31A and 31). As shown in FIG. 32, in some embodiments one or more depots 100 may be positioned along or adjacent the subcutaneous skin incision.

In some embodiments, the system includes a first depot (or plurality of depots) and a second depot (or plurality of depots), all of which are configured to be implanted at or near the knee joint. The first depot(s) may have the same or different release profile, rate of release, therapeutic agent (such as non-anesthetic analgesics, NSAIDs, antibiotics, etc.), duration of release, size, shape, configuration, total payload, etc. as the second depot(s).

So as not to interfere or overlap with a peripheral nerve block administered perioperatively to the patient, one or more of the depots may optionally include a delay release capability for 6 to 24 hours following implantation. In some embodiments, one or more depots placed in the adductor canal and knee capsule may be configured to have a delay in the release of therapeutic agent that may exceed 24 hours.

The depots 100 disclosed herein may be used to treat postoperative pain associated with other knee surgeries. For example, one or more depots may be used to treat postoperative pain associated with an ACL repair surgery, a medial collateral ligament ("MCL") surgery, and/or a posterior cruciate ligament ("PCL") surgery. For ACL repair, one or more depots may be positioned to delivery analgesic the femoral and/or sciatic nerves, while for PCL repair surgery, one or more depots may be positioned parasacral to deliver analgesic to the sciatic nerve. The one or more depots may be used to treat postoperative pain associated with a partial knee replacement surgery, total knee replacement surgery, and/or a revision surgery of a knee replacement surgery. In such procedures, one or more depots can be placed contiguous to the joint or repair site to provide a local block, or else may suitably positioned to provide a regional block by delivering an analgesic to one or more of the femoral nerve or the sciatic nerve, for example via placement in the adductor canal.

In addition to the knee-related surgeries described above, embodiments of the depots disclosed herein can be used to treat postoperative pain associated with other orthopedic surgeries as described in more detail below and as summarized in part in FIGS. 28A-28C. Examples include surgical procedures involving the ankle, hip, shoulder, wrist, hand, spine, legs, or arms. For at least some of these surgical procedures, analgesic can be provided to deliver a local block or a regional block to treat postoperative pain. For a local block, one or more depots can be attached under direct vision in open surgery, for example during joint arthroplasty, open reduction and internal fixation (ORIF) surgery, ligament reconstruction, etc. In such procedures involving a joint, one or more depots can be positioned at the joint capsule (e.g., at or near the intracapsular and/or extracapsular space of the joint) or adjacent soft tissues spaced apart from articulating surfaces to avoid the depot interfering with joint movement or being damaged by contact with articulating surfaces. In cases involving fracture repair or ligament repair, one or more depots can be positioned at or adjacent to the repair site to provide a local block. For a regional block, one or more depots can be deposited at a treatment site adjacent to the target nerve via ultrasound guidance using a blunt trocar catheter or other suitable instrument. In at least some embodiments, it can be beneficial to combine delivery of analgesic or other therapeutic agents via the depot(s) with delivery of NSAIDs, a long-acting narcotic delivered pre-operatively, and/or acetaminophen. The sustained, controlled, release of an analgesic via the one or more depots may work in concert with these other therapeutic agents to provide a reduction in postoperative pain associated with orthopedic and other surgical procedures.

In one example, one or more depots as described herein can be used to treat postoperative pain associated with foot and ankle surgeries such as ankle arthroplasty (including ankle revision, ankle replacement, and total ankle replacement), ankle fusion, ligament reconstruction, corrective osteotomies (e.g., bunionectomy, pes planus surgery), or open reduction and internal fixation (ORIF) of ankle or foot fractures. In treating postoperative pain associated with such surgeries, one or more depots can be configured and positioned adjacent to the joint or repair site to provide a local block. Additionally or alternatively, one or more depots can be placed parasacral or at another suitable location to target one or more of the subgluteal sciatic nerve, popliteal sciatic nerve, deep peroneal nerve, or the superficial peroneal nerve. In some embodiments, depots positioned to treat postoperative pain associated with ankle or foot surgeries can have a release profile configured to deliver therapeutically beneficial levels of analgesic for a period of between 3-7 days.

In another example, one or more depots as described herein can be used to treat postoperative pain associated with hip surgeries such as hip arthroplasty (including hip revision, partial hip replacement, and total hip replacement) or open reduction and internal fixation (ORIF) of hip fractures. In treating postoperative pain associated with such surgeries, one or more depots can be configured and positioned adjacent to the joint or repair site to provide a local block. Additionally or alternatively, a regional block can be provided by placing depots in the psoas compartment, lumbar paravertebral space, fascia iliaca, or other suitable location to target one or more of the lumbar plexus, sacral plexus, femoral nerve, sciatic nerve, superior gluteal nerve, or obturator nerve. In some embodiments, it may be beneficial to secure the one or more depot(s) (e.g., using a fixation mechanism as described herein) to maintain an anterior position of the depot, thereby preventing or reducing exposure of analgesic to motor nerves (e.g., sciatic or femoral nerves). In some embodiments, depots positioned to treat postoperative pain associated with hip surgeries can have a release profile configured to deliver therapeutically beneficial levels of analgesic for a period of 5-7 or 7-10 days depending on the particular surgical procedure.

Post-operative pain associated with shoulder and upper-arm surgeries can likewise be treated using one or more depots as disclosed herein. Examples of such surgeries include shoulder arthroplasty (including shoulder revision, partial shoulder replacement, and total shoulder replacement), upper-arm fracture repair (scapular, humerus), ligament/tendon repair (e.g., rotator cuff, labrum, biceps, etc.), or open reduction and internal fixation (ORIF) of fractures of the shoulder or upper arm. In treating postoperative pain associated with such surgeries, one or more depots can be configured and positioned adjacent to the joint or repair site to provide a local block. Additionally or alternatively, one or more depots can be configured and positioned to target the brachial plexus by placing one or more depots in the cervical paravertebral space, interscalene, or supraclavicular space. In some embodiments, interscalene placement of the depots can avoid exposure of analgesic to native cartilage, thereby reducing the risk of chondrotoxicity. In some embodiments, depots positioned to treat postoperative pain associated with shoulder or upper-arm related surgeries can have a release profile configured to deliver therapeutically beneficial levels of analgesic for a period of 3-7 days.

In another example, one or more depots as described herein can be used to treat postoperative pain associated with elbow surgeries such as elbow arthroplasty (including elbow revision, partial elbow replacement, and total elbow replacement), ligament reconstruction, or open reduction and internal fixation (ORIF) of fractures of the elbow. In treating postoperative pain associated with such surgeries, one or more depots can be positioned adjacent to the joint or repair site to provide a local block. Additionally or alternatively, one or more depots can be configured and positioned to target the brachial plexus nerves, for example by being placed at or near the cervical paravertebral space, infraclavicular, or axillary position, or other suitable location. In some embodiments, depots positioned to treat postoperative pain associated with elbow surgeries can have a release profile configured to deliver therapeutically beneficial levels of analgesic for a period of 3-7 days.

Post-operative pain associated with wrist and hand surgeries can also be treated using one or more depots as described herein. Examples of wrist and hand surgeries include wrist arthroplasty (including wrist revision, partial wrist replacement, and total wrist replacement), wrist fusion, and open reduction and internal fixation (ORIF) of fractures of the wrist. In treating postoperative pain associated with such surgeries, one or more depots can be configured and positioned adjacent to the wrist joint or repair site to provide a local block. Additionally or alternatively, one or more depots can be configured and positioned to target the target the ulnar, median, radial, and cutaneous forearm nerves, for example via placement at the antecubital fossa, cervical paravertebral space, infraclavicular, or axillary position. In some embodiments, depots positioned to treat postoperative pain associated with wrist and hand surgeries can have a release profile configured to deliver therapeutically beneficial levels of analgesic for a period of 3-7 days.

The depots disclosed herein may likewise be used to treat postoperative pain from other orthopedic surgeries. For example, post-operative pain associated with spinal fusion can be treated via placement of one or more depots subcutaneously or in the paravertebral space. In treatment of post-operative pain associated with fibular fracture repair, one or more depots can be configured and placed to target the sciatic nerve and/or the popliteal sciatic nerve, for example being placed parasacral. Various other placements and configurations are possible to provide therapeutic relief from post-operative pain associated with orthopedic surgical procedures.

V. SELECTED SYSTEMS AND METHODS FOR TREATING POSTOPERATIVE PAIN ASSOCIATED WITH NON-ORTHOPEDIC SURGERY

The depots 100 of the present technology may be used to treat a variety of medical conditions depending upon the nature of the therapeutic agent delivered as described above. The therapeutic agent may be delivered to specific areas of the patient's body depending upon the medical condition being treated. The depots 100 of the present technology may be positioned in vivo proximate to the target tissue in the patient's body to provide a controlled, sustained release of a therapeutic agent for the treatment of a particular condition. This implantation may be associated with a surgery or intervention for acutely treating the particular condition, whereby the depot enables chronic, sustained pharmacological treatment following completion of the surgery or intervention. The depot 100 may be a standalone element, or may be coupled to or integrated as part of an implantable device or prosthesis associated with the intervention or surgery.

The amount of the therapeutic agent that will be effective in a patient in need thereof will depend on the specific nature of the condition, and can be determined by standard clinical techniques known in the art. In addition, in vitro or in vivo assays may optionally be employed to help identify optimal dosage ranges. The specific dose level for any particular individual will depend upon a variety of factors including the activity of the drug, the age, body weight, general physical and mental health, genetic factors, environmental influences, sex, diet, time of administration, location of administration, rate of excretion, and the severity of the particular problem being treated.

Some aspects of the present technology include a system comprising a plurality of depots (each of which could be any of the depots described herein) provided for implantation by a clinical practitioner. In this system, each depot may be configured for controlled release of therapeutic agent to tissue proximate to the implantation site of the depot. The depots in the system may be identical or may vary in several respects (e.g., form factor, therapeutic agent, release profile, etc.). For example, the system may be comprised of a depot having a release profile that provides for an immediate release of therapeutic agent and other depots comprised of a depot having a release profile that provides for a delayed release of therapeutic agent.

Many depots of the present technology are configured to be implanted at a surgical site to treat postoperative pain at or near the site. As used herein, the term "pain" includes nociception and the sensation of pain, both of which can be assessed objectively and subjectively, using pain scores and other methods well-known in the art, such as opioid usage. In various embodiments, pain may include allodynia (e.g., increased response to a normally non-noxious stimulus) or hyperalgesia (e.g., increased response to a normally noxious or unpleasant stimulus), which can in turn be thermal or mechanical (tactile) in nature. In some embodiments, pain is characterized by thermal sensitivity, mechanical sensitivity and/or resting pain. In other embodiments, pain comprises mechanically-induced pain or resting pain. In still other embodiments, the pain comprises resting pain. The pain can be primary or secondary pain, as is well-known in the art. Exemplary types of pain reducible, preventable or treatable by the methods and compositions disclosed herein include, without limitation, include post-operative pain and neuropathic pain of the arm, neck, back, lower back, leg, and related pain distributions. Neuropathic pain may include pain arising from surgery to the nerve root, dorsal root ganglion, or peripheral nerve.

In various embodiments, the pain results from "post-surgical pain" or "post-operative pain" or "surgery-induced pain," which are used herein interchangeably, and refer to pain arising in the recovery period of seconds, minutes, hours, days or weeks following a surgical procedure. Surgical procedures include any procedure that penetrates beneath the skin and causes pain and/or inflammation to the patient. Surgical procedure also includes arthroscopic surgery, an excision of a mass, spinal fusion, thoracic, cervical, or lumbar surgery, pelvic surgery, chest-related surgery, breast-related surgery, gynecological or obstetric surgery, general, abdominal, or urological surgery, ear, nose, and throat (ENT) surgery, oral and maxillofacial surgery, oncological surgery, cosmetic surgery, or a combination thereof. FIGS. 28A-28C illustrate a table showing common surgical procedures for which the depots 100 of the present technology may be utilized for treating postoperative pain.

Many embodiments of the present technology include one or more depots, having the same or different configuration and/or dosing, that are configured to be positioned at or near a surgical site to treat pain associated with recovering from a surgical procedure. As previously described, the depots of the present technology may be solid, self-supporting, flexible thin films that is structurally capable of being handled by a clinician during the normal course of a surgery without breaking into multiple pieces and/or losing its general shape.

This way, the clinician may position one or more of the depots at various locations at or near the treatment site, as necessary to address a particular patient's needs and/or to target particular nerves innervating the surgical site.

In some embodiments, the system includes a first depot (or plurality of depots) and a second depot (or plurality of depots), all of which are configured to be implanted at or near the treatment site. The first depot(s) may have the same or different release profile, rate of release, therapeutic agent contained (such as non-anesthetic analgesics, NSAIDs, antibiotics, etc.), duration of release, size, shape, configuration, total payload, etc. as the second depot(s).

So as not to interfere or overlap with a peripheral nerve block administered perioperatively to the patient, one or more of the depots may optionally include a delay release capability for 6 to 24 hours following implantation. In some embodiments, one or more depots placed at the treatment site may be configured to have a delay in the release of therapeutic agent that may exceed 24 hours.

The depots disclosed herein may be used to treat postoperative pain associated with a wide variety of surgeries. For example, as summarized in FIGS. 28A-28C, the depots may be used to treat postoperative pain for chest-related surgery, breast-related surgery, gynecological or obstetric surgery, general, abdominal, or urological surgery, ear, nose, and throat (ENT) surgery, oral and maxillofacial surgery, oncological surgery, or cosmetic surgery). For particular surgeries or classes of surgeries, one or more depots can be positioned at a treatment site to treat postoperative pain. The treatment site may be at or near the surgical site, or in some embodiments may be separated from the surgical site and proximate to a target nerve or nerve bundle that innervates the surgical site.

In one example, one or more depots as described herein can be used to treat postoperative pain associated with chest-related surgeries such as a thoracotomy, esophageal surgery, cardiac surgery, lung resection, thoracic surgery, or other such procedure. In treating postoperative pain associated with such surgeries, one or more depots can be configured and positioned to target the intercostal nerves, for example by being placed at or near the thoracic paravertebral space or other suitable location. Analgesics delivered to the intercostal nerves can reduce pain in a patient's chest area, thereby relieving postoperative pain associated with the above-noted chest-related surgical procedures.

In another example, one or more depots disclosed herein can be used to treat postoperative pain associated with breast-related surgeries such as a mastectomy, breast augmentation, breast reduction, breast reconstruction procedure, or other such procedure. To treat postoperative pain from such procedures, one or more depots can be positioned and configured to deliver analgesics or other therapeutic agents to the intercostal nerves, for example via placement at or near the patient's infraclavicular space or other suitable location. Additionally or alternatively, one or more depots can be positioned and configured to deliver analgesics or other therapeutic agents to the lateral pectoral nerve and/or the medial pectoral nerve, for example via placement between the serratus anterior muscle and the latissimus dorsi muscle or other suitable location. As noted above, analgesics delivered to the intercostal nerves can reduce pain in a patient's chest area, while analgesics delivered to the lateral and/or medial pectoral nerves can reduce pain in the pectoralis major and pectoralis minor, thereby reducing postoperative pain associated with the above-noted chest-related surgical procedures.

As another example, one or more depots can be used to treat postoperative pain associated with general, abdominal, and/or urological procedures. Examples of such procedures include proctocolectomy, pancreatectomy, appendectomy, hemorrhoidectomy, cholecystectomy, kidney transplant, nephrectomy, radical prostatectomy, nephrectomy, gastrectomy, small bowel resection, splenectomy, incisional hernia repair, inguinal hernia repair, sigmoidectomy, liver resection, enterostomy, rectum resection, kidney stone removal, and cystectomy procedures. For such operations, postoperative pain can be treated by placing one or more depots to target nerves at the transverse abdominis plane (TAP). Analgesics delivered to the TAP can anesthetize the nerves that supply the anterior abdominal wall, thereby reducing postoperative pain in this region. In some embodiments, one or more depots are disposed between the internal oblique and transverse abdominis muscles. In some embodiments, one or more depots can be disposed at or adjacent to the abdominal wall, for example being secured in place via fixation mechanisms as described in more detail below.

In some embodiments, one or more depots are used to treat postoperative pain associated with gynecological and obstetric surgeries, for example a myomectomy, Caesarian section, hysterectomy, oophorectomy, pelvic floor reconstruction, or other such surgical procedure. For such procedures, the depot(s) can be configured and positioned to deliver analgesics or other therapeutic agents to one or more of the nerves innervating the pelvic and/or genital area, for example the pudendal nerve, intercostal nerve, or other suitable nerve.

In some embodiments, one or more depots can be used to treat postoperative pain associated with ear, nose, and threat (ENT) surgical procedures, for example tonsillectomy, submucosal resection, rhinoplasty, sinus surgery, inner ear surgery, parotidectomy, submandibular gland surgery, or other such operation. Similarly, one or more depots can be used to treat postoperative pain associated with oral and maxillofacial surgeries, for example dentoalveolar surgery, dental implant surgery, orthognathic surgery, temporomandibular joint (TMJ) surgery, dental reconstruction surgeries, or other such operations. For ENT surgical procedures and oral and maxillofacial surgical procedures, the depot(s) can be configured and positioned to deliver analgesics or other therapeutic agents to one or more of the nerves innervating regions affected by the surgical procedure, for example the mandibular nerve, the mylohyoid nerve, lingual nerve, inferior alveolar nerve, buccal nerve, auriculotemporal nerve, anterior ethmoidal nerve, or other suitable nerve.

One or more depots 100 can also be used to treat postoperative pain for other surgical procedures, for example oncological surgeries (e.g., tumor resection), cosmetic surgeries (e.g., liposuction), or other surgical procedure resulting in postoperative pain. For treatment of postoperative pain associated with any particular surgery, the number of depots and the characteristics of individual depots can be selected to deliver the desired therapeutic benefits. For example, the dimensions of the depot(s), the amount of therapeutic agent per depot, the release profile, and other characteristics can be tuned to provide the desired treatment of postoperative pain. For example, while a patient recovering from a knee-replacement surgery may benefit from delivery of analgesics for at least 14 days, a patient recovering from a tonsillectomy may not require the same level or duration of analgesic drug delivery. As such, depots delivered to a patient for treatment of postoperative pain following a tonsillectomy may require fewer depots, or depots having a smaller payload of therapeutic agent, or depot(s)

having a steeper release profile, etc. Additionally, the number and characteristics of the depot(s) selected for implantation can be tailored to accommodate the target anatomical region for placement in the patient's body.

VI. CONCLUSION

Although many of the embodiments are described above with respect to systems, devices, and methods for treating postoperative pain, the technology is applicable to other applications and/or other approaches. For example, the depots of the present technology may be used to treat postoperative pain associated with a veterinary procedure and/or surgery. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 2-32.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. For example, reference to "a therapeutic agent" includes one, two, three or more therapeutic agents.

The headings above are not meant to limit the disclosure in any way. Embodiments under any one heading may be used in conjunction with embodiments under any other heading.

We claim:

1. A depot for treating postoperative pain, the depot comprising:
    a therapeutic region including a biodegradable polymer, an analgesic, and a releasing agent, the therapeutic region having a first surface, a second surface opposite the first surface, and an exposed sidewall between the first and second surfaces;
    a first control region covering the first surface of the therapeutic region and having a thickness no greater than 1/50 of a thickness of the therapeutic region, the first control region comprising a biodegradable polymer; and
    a second control region covering the second surface of the therapeutic region and having a thickness no greater than 1/50 of the thickness of the therapeutic region, the second control region comprising a biodegradable polymer,
    wherein the analgesic constitutes at least 50% of a total weight of the depot, and
    wherein, when the depot is implanted at a treatment site, the depot is configured to release the analgesic at the treatment site for a release duration of no less than 14 days, wherein the depot is configured to release the analgesic at a first rate for an initial period of the release duration and at a second rate for a subsequent period of the release duration, the second rate being slower than the first rate.

2. The depot of claim 1, wherein, when implanted, the depot is configured to release 20% to 50% of the analgesic in the first 3 days to 5 days of the release duration, and at least 80% of the remaining analgesic in the remaining days of the release duration.

3. The depot of claim 1, wherein a surface area of the exposed sidewall of the therapeutic region is less than a combined exposed surface area of the first and second control regions.

4. The depot of claim 1, wherein the releasing agent is hydrophilic.

5. The depot of claim 1, wherein the releasing agent is a polysorbate.

6. The depot of claim 1, wherein the analgesic comprises bupivacaine, lidocaine, ropivacaine, or a pharmaceutically acceptable salt thereof.

7. The depot of claim 1, wherein the first and second control regions do not include any analgesic before the depot is implanted at the treatment site.

8. The depot of claim 1, wherein the biodegradable polymers of the therapeutic region, first control region, and second control region are the same polymer.

9. A depot for sustained, controlled release of a therapeutic agent, the depot comprising:
- a therapeutic region including a biodegradable polymer, the therapeutic agent, and a releasing agent, the therapeutic region having a first surface, a second surface opposite the first surface, and an exposed sidewall between the first and second surfaces;
- a first control region covering the first surface of the therapeutic region and having a thickness no greater than 1/50 of a thickness of the therapeutic region, the first control region comprising a biodegradable polymer; and
- a second control region covering the second surface of the therapeutic region and having a thickness no greater than 1/50 of the thickness of the therapeutic region, the second control region comprising a biodegradable polymer,
- wherein the therapeutic agent constitutes at least 50% of a total weight of the depot, and
- wherein, when the depot is implanted at a treatment site, the depot is configured to release the therapeutic agent at the treatment site for a release duration of no less than 14 days, wherein the depot is configured to release the therapeutic agent at a first rate for an initial period of the release duration and at a second rate for a subsequent period of the release duration, the second rate being slower than the first rate.

10. The depot of claim 9, wherein the therapeutic agent is configured to treat pain.

11. The depot of claim 10, wherein the pain comprises postoperative pain.

12. The depot of claim 9, wherein a surface area of the exposed sidewall of the therapeutic region is less than a combined exposed surface area of the first and second control regions.

13. The depot of claim 9, wherein the first and second control regions do not include any therapeutic agent before the depot is implanted at the treatment site.

14. The depot of claim 9, wherein the release duration is no less than 21 days.

15. The depot of claim 9, wherein, while implanted, the depot is configured to release up to 50% of the therapeutic agent in the first 8 days of the release duration.

16. The depot of claim 9, wherein, while implanted, the depot is configured to release 20% to 50% of the therapeutic agent in the first 3 days to 5 days of the release duration, and at least 80% of the remaining therapeutic agent in the remaining days of the release duration.

17. A method for treating postoperative pain associated with a surgical procedure, the method comprising:
- implanting a depot at a treatment site in a patient, wherein the depot comprises:
  - a therapeutic region including a biodegradable polymer, n analgesic, and a releasing agent, wherein the analgesic constitutes at least 50% of a total weight of the depot, and
  - a pair of control regions disposed at two sides of the therapeutic region, each control region including a biodegradable polymer, wherein each control region has a thickness no greater than 1/50 of a thickness of the therapeutic region; and
- releasing the analgesic at the treatment site for a release duration of at least 14 days, wherein the analgesic is released at a first rate for an initial period of the release duration and at a second rate for a subsequent period of the release duration, the second rate being slower than the first rate.

18. The method of claim 17, wherein the initial period of the release duration corresponds to an acute pain period after the surgical procedure, and the subsequent period of the release duration corresponds to a subacute pain period after the surgical procedure.

19. The method of claim 17, wherein the surgical procedure comprises a knee surgery.

20. The method of claim 19, wherein the knee surgery comprises a total knee arthroplasty.

21. The method of claim 19, wherein the depot is implanted within an intracapsular space of a knee joint of the patient.

22. The method of claim 17, wherein the surgical procedure comprises a hip surgery, a shoulder surgery, a hernia repair surgery, a bunionectomy, a breast surgery, or an abdominal surgery.

23. The method of claim 17, wherein 20% to 50% of the analgesic is released in the first 3 days to 5 days of the release duration, and at least 80% of the remaining analgesic is released in the remaining days of the release duration.

24. The method of claim 17, wherein up to 50% of the analgesic is released in the first 8 days of the release duration.

25. The method of claim 17, wherein the release duration is at least 21 days.

26. The method of claim 17, wherein:
- the analgesic comprises bupivacaine, lidocaine, ropivacaine, or a pharmaceutically acceptable salt thereof,
- the biodegradable polymers of the therapeutic region and the control regions each comprise poly(DL-lactide-co-glycolide), and
- the releasing agent comprises a polysorbate.

27. The method of claim 17, wherein implanting the depot comprises positioning the depot proximate to one or more target nerves.

28. The depot of claim 1, wherein the biodegradable polymers of the therapeutic region, the first control region, and the second control region each are poly(lactide-co-glycolide).

29. The depot of claim 28, wherein the analgesic is bupivacaine hydrochloride, and the releasing agent is a polysorbate.

30. The depot of claim 9, wherein the biodegradable polymers of the therapeutic region, the first control region, and the second control region each are poly(lactide-co-glycolide).

31. The depot of claim 30, wherein the analgesic is bupivacaine hydrochloride, and the releasing agent is a polysorbate.

* * * * *

UNITED STATES PATENT AND TRADEMARK OFFICE
CERTIFICATE OF CORRECTION

| | | |
|---|---|---|
| PATENT NO. | : 11,969,500 B2 | Page 1 of 1 |
| APPLICATION NO. | : 17/454320 | |
| DATED | : April 30, 2024 | |
| INVENTOR(S) | : Naga et al. | |

It is certified that error appears in the above-identified patent and that said Letters Patent is hereby corrected as shown below:

In the Claims

In Column 81, in Claim 17, Line 57, delete "n analgesic," and insert -- an analgesic, --, therefor.

Signed and Sealed this
Eleventh Day of June, 2024

Katherine Kelly Vidal
*Director of the United States Patent and Trademark Office*